US012258419B2

(12) United States Patent
Tian et al.

(10) Patent No.: US 12,258,419 B2
(45) Date of Patent: Mar. 25, 2025

(54) ANTI-FXI/FXIA ANTIBODY AND USE THEREOF

(71) Applicants: SICHUAN KELUN-BIOTECH BIOPHARMACEUTICAL CO., LTD., Chengdu (CN); KLUS PHARMA INC., Cranbury, NJ (US)

(72) Inventors: Haijun Tian, Cranbury, NJ (US); Dengnian Liu, Chengdu (CN); Sujun Deng, Cranbury, NJ (US); Marc Peter Ciucci, Cranbury, NJ (US); Cheng Wang, Chengdu (CN); Yong Zheng, Chengdu (CN); Liang Xiao, Chengdu (CN); Tongtong Xue, Chengdu (CN); Jingyi Wang, Chengdu (CN)

(73) Assignees: Sichuan Kelun-Biotech Biopharmaceutical Co., Ltd., Chengdu (CN); Klus Pharma Inc., Cranbury, NJ (US)

( * ) Notice: Subject to any disclaimer, the term of this patent is extended or adjusted under 35 U.S.C. 154(b) by 778 days.

(21) Appl. No.: 17/310,957

(22) PCT Filed: Apr. 6, 2020

(86) PCT No.: PCT/CN2020/083413
§ 371 (c)(1),
(2) Date: Sep. 1, 2021

(87) PCT Pub. No.: WO2020/211674
PCT Pub. Date: Oct. 22, 2020

(65) Prior Publication Data
US 2022/0162338 A1 May 26, 2022

(30) Foreign Application Priority Data
Apr. 16, 2019 (CN) .......................... 201910303627.7

(51) Int. Cl.
*C07K 16/36* (2006.01)
*A61K 39/395* (2006.01)
*A61K 45/06* (2006.01)
*G01N 33/86* (2006.01)

(52) U.S. Cl.
CPC .......... *C07K 16/36* (2013.01); *A61K 39/3955* (2013.01); *A61K 45/06* (2013.01); *G01N 33/86* (2013.01); *C07K 2317/20* (2013.01); *C07K 2317/24* (2013.01); *C07K 2317/31* (2013.01); *C07K 2317/76* (2013.01); *C07K 2317/92* (2013.01); *G01N 2333/96452* (2013.01)

(58) Field of Classification Search
CPC ..................... C07K 16/36; G01N 2333/96452
See application file for complete search history.

(56) References Cited

U.S. PATENT DOCUMENTS

| | | |
|---|---|---|
| 3,817,837 A | 6/1974 | Rubenstein |
| 3,850,752 A | 11/1974 | Schuurs |
| 3,939,350 A | 2/1976 | Kronick |
| 3,996,345 A | 12/1976 | Ullman |
| 4,275,149 A | 6/1981 | Litman |
| 4,277,437 A | 7/1981 | Maggio |
| 4,366,241 A | 12/1982 | Tom et al. |
| 4,816,567 A | 3/1989 | Cabilly |
| 5,225,539 A | 7/1993 | Winter |
| 5,530,101 A | 6/1996 | Queen |
| 5,585,089 A | 12/1996 | Queen |
| 5,693,762 A | 12/1997 | Queen |
| 6,180,370 B1 | 1/2001 | Queen et al. |
| 8,388,959 B2 | 3/2013 | Gruber et al. |
| 2015/0030596 A1 | 1/2015 | Cheong et al. |

FOREIGN PATENT DOCUMENTS

| | | |
|---|---|---|
| CN | 104341529 A | 2/2015 |
| CN | 108409863 A | 8/2018 |
| EP | 3581587 A1 | 12/2019 |
| WO | 200243478 A2 | 6/2002 |
| WO | 2013167669 A1 | 11/2013 |
| WO | 2015141862 A1 | 9/2015 |

(Continued)

OTHER PUBLICATIONS

Tucker, Erik I., et al. "Apple Domain-Specific Anti-Factor XI Antibodies Inhibit Venous-Type Thrombosis with Improved Hemostatic Safety Profiles Compared to Enoxaparin in Primates." Blood 118.21 (2011): 1173. (Year: 2011).*

(Continued)

*Primary Examiner* — Julie Wu
*Assistant Examiner* — Bryan William Heck
(74) *Attorney, Agent, or Firm* — MORRISON & FOERSTER LLP

(57) ABSTRACT

The present invention relates to the field of therapeutic monoclonal antibodies, and specifically provides an anti-FXI/FXIa antibody or an antigen-binding fragment thereof, nucleic acid molecules encoding same, and methods for preparing same. The anti-FXI/FXIa antibody or antigen-binding fragment thereof described in the present invention has specificity and high affinity to FXI/FXIa, and can effectively inhibit the activity of FXI/FXIa. Therefore, the present invention further provides a pharmaceutical composition comprising the antibody or antigen-binding fragment thereof, and a use thereof in the preparation of a drug which is used for the prevention and/or treatment of diseases or disorders related to coagulation or thromboembolism.

27 Claims, 9 Drawing Sheets
Specification includes a Sequence Listing.

(56) References Cited

FOREIGN PATENT DOCUMENTS

| WO | WO-2016207858 A1 * | 12/2016 | ......... A61K 39/3955 |
|---|---|---|---|
| WO | 2017127468 A1 | 7/2017 | |
| WO | 2017162791 A1 | 9/2017 | |
| WO | 2018116255 A1 | 6/2018 | |
| WO | 2018116267 A2 | 6/2018 | |
| WO | 2018145533 A1 | 8/2018 | |
| WO | 2020008022 A1 | 1/2020 | |
| WO | 2020211674 A1 | 10/2020 | |

OTHER PUBLICATIONS

Schaefer, Martina, et al. "Allosteric inhibition as a new mode of action for BAY 1213790, a neutralizing antibody targeting the activated form of coagulation factor XI." Journal of molecular biology 431.24 (2019): 4817-4833. (Year: 2019).*
International Search Report and Written Opinion of the International Searching Authority, dated Jul. 9, 2020, for PCT Application No. PCT/CN2020/083413, 8 pages. English Translation.
Zilberman-Rudenko, J. et al. (Mar. 2016). "Coagulation Factor XI Promotes Distal Platelet Activation and Single Platelet Consumption in the Bloodstream Under Shear Flow," Arterioscler Thromb. Vasc. Biol. 36(3):510-517.
Alfthan, K. et al. (Jul. 1995). "Properties of a Single-Chain Antibody Containing Different Linker Peptides," Protein Eng. 8(7):725-731.
Altschul, S.F. et al. (Feb. 1994). "Issues in Searching Molecular Sequence Databases," Nature Genet. 6:119-129.
Ausubel, F.M. et al. (1995). Short Protocols in Molecular Biology, Greene Publishing and Wiley Interscience, New York, New York, (Table of Contents), 22 pages.
Bird, R.E. et al. (Oct. 21, 1988). "Single-Chain Antigen-Binding Proteins," Science 242(4877):423-426.
Brennan, M. et al. (Jul. 5, 1985). "Preparation of Bispecific Antibodies by Chemical Recombination of Monoclonal Immunoglobulin G1 Fragments," Science 229:81-83.
Brodeur, B.R. et al. (1987). "Mouse-Human Myeloma Partners for the Production Monoclonal Antibody Production of Heterohybridomas," Chapter 4 in Techniques and Applications, Marcel Dekker, Inc., New York, pp. 51-63.
Brummell, D.A. et al. (1993). "Probing the Combining Site of an Anti-Carbohydrate Antibody by Saturation-Mutagenesis: Role of the Heavy-Chain CDR3 Residues," Biochemistry 32(4):1180-1187.
Brüggemann, M. et al. (1993). "Designer Mice: The Production of Human Antibody Repertoires in Transgenic Animals," Year in Immuno. 7:33-40.
Burks, E.A. et al. (1997). "In Vitro Scanning Saturation Mutagenesis of an Antibody Binding Pocket," PNAS 94 (2):412-417.
Carter, P. et al. (Feb. 1992). "High Level *Escherichia coli* Expression and Production of a Bivalent Humanized Antibody Fragment," Bio/Technology 10:163-167.
Choi, i. et al. (2001). "Recombinant Chimeric OKT3 scFv IgM Antibodies Mediate Immune Suppression While Reducing T Cell Activation in vitro," Eur. J. Immunol. 31:94-106.
Chothia, C. et al. (Aug. 20, 1987). "Canonical Structures for the Hypervariable Regions of Immunoglobulins," J. Mol. Biol. 196(4):901-917.
Chothia, C. et al. (Dec. 21/28, 1989). "Conformations of Immunoglobulin Hypervariable Regions," Nature 342 (6252):877-883.
Clackson, T. et al. (Aug. 15, 1991). "Making Antibody Fragments Using Phage Display Libraries," Nature 352:624-628.
Clark, M. (2000). "Antibody Humanization: a Case of the 'Emperor's New Clothes'?" Immunology Today 21 (8):397-402.
Davies, D.R. et al. (1990). "Antibody-Antigen Complexes," Annual Rev. Biochem. 59:439-473.
Duchosal, M.A. et al. (Jan. 16, 1992). "Immunization Of Hu-PBL-SCID Mice and The Rescue Of Human Monoclonal Fab Fragments Through Combinatorial Libraries," Nature 355:258-262.

Goding, J.W. (1983). Monoclonal Antibodies: Principles and Practice, pp. 56-103.
Higgins, D.G. et al. (1989). "Fast and Sensitive Multiple Sequence Alignments on a Microcomputer," CABIOS Communications 5(2):151-153.
Holliger, P. et al. (Jul. 1993). "'Diabodies'": Small Bivalent and Bispecific Antibody Fragments, Proceedings of the National Academy of Sciences USA 90:6444-6448.
Holliger, P. et al. (Sep. 2005) "Engineered Antibody Fragments and The Rise Of Single Domains," Nat. Biotechnol. 23(9):1126-1136.
Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.
Hu, S.-Z. et al. (Jul. 1, 1996). "Minibody: A Novel Engineered Anti-Carcinoembryonic Antigen Antibody Fragment (Single-Chain Fv-CH3) Which Exhibits Rapid, High-Level Targeting Of Xenografts," Cancer Res. 56:3055-3061.
Hudson, P.J. (Oct. 1999). "Recombinant Antibody Constructs in Cancer Therapy," Curr. Opin. Immunol. 11 (5):548-557.
Huston, J.S. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
Jakobovits, A. et al. (Mar. 18, 1993). "Germ-Line Transmission And Expression Of A Human-Derived Yeast Artificial Chromosome," Nature 362(6417):255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90 (6):2551-2555.
Jones, P.T. et al. (May 29, 1986). "Replacing the Complementarity-Determining Regions in a Human Antibody With Those From a Mouse," Nature 321:522-525.
Kabat, E.A. (1991). Sequences of Proteins of Immunological Interest, 5th Edition, U.S. Department of Health and Human Services, NIH Publication No. 91-3242, p. 689.
Kabat, E.A. et al. (1991). Sequences of Proteins of Immunological Interest, 5th ed., Public Health Service, National Institutes of Health, Bethesda, MD. TOC, 21 pages.
Kawabata, S.-I. et al. (1988). "Highly Sensitive Petide-4-Methylcounmaryl-7-Amide Substrates for Blood-Clotting Proteases and Trypsin," Eur. J. Biochem. 172:17-25.
Kipriyanov, S.M. et al. (1999). "Bispecific Tandem Diabody for Tumor Therapy with Improved Antigen Binding and Pharmacokinetics," J Mol Biol 293(1):41-56.
Kobayashi, H. et al. (1999). "Tryptophan H33 Plays an Important Role in Pyrimidine (6-4) Pyrimidone Photoproduct Binding by a High-Affinity Antibody," Protein Engineering 12:879-884.
Kohler, G. et al. (Aug. 7, 1975) "Continuous Cultures Of Fused Cells Secreting Antibody Of Predefined Specificity," Nature 256:495-497.
Kozbor, D. et al. (Dec. 1984). "A Human Hybrid Myeloma for Production of Human Monoclonal Antibodies," J. Immunol. 133(6):3001-3005.
Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.
Little, M. et al. (2000). "Of Mice and Men: Hybridoma and Recombinant Antibodies," Immunol. Today 21(8):364-370.
Lo, B.C.K. (2004). "Antibody Humanization By CDR Grafting," in Methods in Molecular Biology, vol. 248: Antibody Engineering: Methods and Protocols, ed. B.K.C. Lo, Humana Press Inc., Totowa, NJ, pp. 135-159.
Lonberg, N. et al. (Apr. 28, 1994). "Antigen-Specific Human Antibodies From Mice Comprising Four Distinct Genetic Modifications," Nature 368:856-859.
Malmqvist M. (Jan. 14, 1993). "Biospecific Interaction Analysis Using Biosensor Technology," Nature 361:186-187.
Marks, J.D. et al. (1991). "By-Passing Immunization: Human Antibodies From V-Genen Libraries Displayed on Phage," J. Mol. Biol. 222:581-597.

(56) References Cited

OTHER PUBLICATIONS

Martin, A.C.R. et al. (Dec. 1989). "Modeling Antibody Hypervariable Loops: A Combined Algorithm," PNAS USA 86(23):9268-9272.
Meyers, E. et al. (1988). "Optimal Alignments in Linear Space," Comput. Appl. Biosci., 4(1):11-17.
Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Munson, P.J. et al. (1980). "LIGAND: A Versatile Computerized Approach for Characterization of Ligand-Binding Systems," Anal. Biochem. 107:220-239.
Needleman, S. B. et al. (1970). "A General Method Applicable to the Search for Similarities in the Amino Acid sequence of Two Proteins," J. Mol. Biol. 48:443-453.
Paul, W.E. ed. (1989). Fundamental Immunology: Second Edition, Raven Press, New York, pp. 332-337.
Pinto, D.J.P. et al. (Dec. 14, 2017, e-pub. Oct. 17, 2017). "Discovery of a Parenteral Small Molecule Coagulation Factor XIa Inhibitor Clinical Candidate (BMS-962212)," J Med Chem., 75 pages.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Poljak, R.J. (Dec. 15, 1994). "Production and Structure of Diabodies," Structure 2(12):1121-1123.
Presta, L.G. (1992). "Antibody Engineering," Current Opinion in Structural Biology 2:593-596.
Riechmann, L. et al. (Mar. 24, 1988). "Reshaping Human Antibodies for Therapy," Nature 332:323-327.
Roovers, R.C. et al. (2007). "Efficient inhibition of EGFR signalling and of tumour growth by antagonistic anti-EGFR Nanobodies," Cancer Immunol. Immunother. 56: 303-317.
Rudikoff, S. et al. (Mar. 1982). "Single Amino Acid Substitution Altering Antigen-Binding Specificity," Proc. Natl. Acad. Sci. USA 79:1979-1983.
Sambrook, J. et al. (1989). Molecular Cloning: A Laboratory Manual, 3rd Ed. 29 pages.
Smith, T.F. et al. (1981). "Comparison of Biosequences," Advances in Appl. Math. 2:482-489.
Vaughan, T.J. et al. (Mar. 1996). "Human Antibodies with Sub-Nanomolar Affinities Isolated from a Large Non-Immunized Phage Display Library," Nature Biotechnology 14(3):309-314.
Ward, E.S. et al. (Oct. 12, 1989). "Binding Activities Of A Repertoire Of Single Immunoglobulin Variable Domains Secreted From *Escherichia coli*," Nature 341(6242): 544-546.
Wilkinson, D. (Apr. 16, 2000). "Ultimate Abs," The Scientist, 11 pages.

* cited by examiner

SEQUENCE LISTING

<160> NUMBER OF SEQ ID NOS: 49

<210> SEQ ID NO 1
<211> LENGTH: 118
<212> TYPE: PRT
<213> ORGANISM: Artificial Sequence
<220> FEATURE:
<223> OTHER INFORMATION: Murine antibody 36G9.10 heavy chain variable
      region

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ser Ala Val Tyr Tyr Cys
                85                  90                  95

Ala Gln Asp Tyr Asp Gly Phe Ala Met Asp Tyr Trp Gly Gln Gly Thr
            100                 105                 110

Ser Val Thr Val Ser Ser
        115

<210> SEQ ID NO 2
<211> LENGTH: 106
<212> TYPE: PRT
<213> ORGANISM: Artificial Sequence
<220> FEATURE:
<223> OTHER INFORMATION: Murine antibody 36G9.10 light chain variable
      region

<400> SEQUENCE: 2

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Thr Trp Phe Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ser Ala Thr Tyr Tyr Cys Leu Gln Tyr Asp Tyr Leu Leu Thr
                85                  90                  95

Phe Gly Gly Gly Thr Lys Leu Glu Ile Lys
            100                 105

<210> SEQ ID NO 3
<211> LENGTH: 8
<212> TYPE: PRT
<213> ORGANISM: Artificial Sequence
<220> FEATURE:
<223> OTHER INFORMATION: IMGT 36G9.10 CDR-H1

<400> SEQUENCE: 3

Gly Phe Asn Ile Lys Asp Thr Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: IMGT 36G9.10 CDR-H2

<400> SEQUENCE: 4

Ile Asp Pro Ala Asn Asp Asn Thr
1               5

<210> SEQ ID NO 5
<211> LENGTH: 11
<212> TYPE: PRT
<213> ORGANISM: Artificial Sequence
<220> FEATURE:
<223> OTHER INFORMATION: IMGT 36G9.10 CDR-H3

<400> SEQUENCE: 5

Ala Gln Asp Tyr Asp Gly Phe Ala Met Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: IMGT 36G9.10 CDR-L1

<400> SEQUENCE: 6

Gln Asp Ile Asn Lys Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: IMGT 36G9.10 CDR-L2

<400> SEQUENCE: 7

Tyr Thr Ser
1

<210> SEQ ID NO 8
<211> LENGTH: 8
<212> TYPE: PRT
<213> ORGANISM: Artificial Sequence
<220> FEATURE:
<223> OTHER INFORMATION: IMGT 36G9.10 CDR-L3

<400> SEQUENCE: 8

Leu Gln Tyr Asp Tyr Leu Leu Thr
1               5

<210> SEQ ID NO 9
<211> LENGTH: 10
<212> TYPE: PRT
<213> ORGANISM: Artificial Sequence
<220> FEATURE:
<223> OTHER INFORMATION: AbM 36G9.10 CDR-H1

<400> SEQUENCE: 9

Gly Phe Asn Ile Lys Asp Thr Tyr Ile His

```
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: AbM 36G9.10 CDR-H2

<400> SEQUENCE: 10

```
Arg Ile Asp Pro Ala Asn Asp Asn Thr Lys
1               5                   10
```

<210> SEQ ID NO 11
<211> LENGTH: 9
<212> TYPE: PRT
<213> ORGANISM: Artificial Sequence
<220> FEATURE:
<223> OTHER INFORMATION: AbM 36G9.10 CDR-H3

<400> SEQUENCE: 11

```
Asp Tyr Asp Gly Phe Ala Met Asp Tyr
1               5
```

<210> SEQ ID NO 12
<211> LENGTH: 11
<212> TYPE: PRT
<213> ORGANISM: Artificial Sequence
<220> FEATURE:
<223> OTHER INFORMATION: AbM 36G9.10 CDR-L1

<400> SEQUENCE: 12

```
Lys Ala Ser Gln Asp Ile Asn Lys Tyr Ile Thr
1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: AbM 36G9.10 CDR-L2

<400> SEQUENCE: 13

```
Tyr Thr Ser Thr Leu Gln Pro
1               5
```

<210> SEQ ID NO 14
<211> LENGTH: 8
<212> TYPE: PRT
<213> ORGANISM: Artificial Sequence
<220> FEATURE:
<223> OTHER INFORMATION: AbM 36G9.10 CDR-L3

<400> SEQUENCE: 14

```
Leu Gln Tyr Asp Tyr Leu Leu Thr
1               5
```

<210> SEQ ID NO 15
<211> LENGTH: 118
<212> TYPE: PRT
<213> ORGANISM: Artificial Sequence
<220> FEATURE:
<223> OTHER INFORMATION: Humanized antibody 36G9.10hz73/36G9.10hz74
      heavy chain variable region

<400> SEQUENCE: 15

Glu Val Gln Leu Val Gln Ser Gly Ala Glu Val Lys Lys Pro Gly Ala

```
                1               5                  10                  15
            Thr Val Lys Ile Ser Cys Lys Ala Ser Gly Phe Asn Ile Lys Asp Thr
                            20                  25                  30

Tyr Ile His Trp Val Gln Gln Ala Pro Gly Lys Gly Leu Glu Trp Met
                        35                  40                  45

Gly Arg Ile Asp Pro Ala Asn Asp Asn Thr Ile Tyr Ala Glu Lys Phe
                    50                  55                  60

Gln Gly Arg Val Thr Ile Thr Ala Asp Thr Ser Thr Asn Thr Ala Tyr
             65                  70                  75                  80

Met Glu Leu Ser Ser Leu Arg Ser Glu Asp Thr Ala Val Tyr Tyr Cys
                            85                  90                  95

Ala Gln Asp Tyr Asp Gly Phe Ala Met Asp Tyr Trp Gly Gln Gly Thr
                        100                 105                 110

Leu Val Thr Val Ser Ser
                    115

<210> SEQ ID NO 16
<211> LENGTH: 118
<212> TYPE: PRT
<213> ORGANISM: Artificial Sequence
<220> FEATURE:
<223> OTHER INFORMATION: Humanized antibody 36G9.10hz43 heavy chain
      variable region

<400> SEQUENCE: 16

Gln Val Gln Leu Val Gln Ser Gly Ala Glu Val Lys Lys Pro Gly Ala
             1               5                  10                  15

Ser Val Lys Val Ser Cys Lys Ala Ser Gly Phe Asn Ile Lys Asp Thr
                            20                  25                  30

Tyr Ile His Trp Val Arg Gln Ala Pro Gly Gln Gly Leu Glu Trp Ile
                        35                  40                  45

Gly Arg Ile Asp Pro Ala Asn Asp Asn Thr Asn Tyr Ala Gln Lys Phe
                    50                  55                  60

Gln Gly Arg Val Thr Met Thr Ala Asp Thr Ser Ile Asn Thr Ala Tyr
             65                  70                  75                  80

Met Glu Leu Ser Arg Leu Arg Ser Asp Asp Thr Ala Val Tyr Tyr Cys
                            85                  90                  95

Ala Gln Asp Tyr Asp Gly Phe Ala Met Asp Tyr Trp Gly Gln Gly Thr
                        100                 105                 110

Leu Val Thr Val Ser Ser
                    115

<210> SEQ ID NO 17
<211> LENGTH: 118
<212> TYPE: PRT
<213> ORGANISM: Artificial Sequence
<220> FEATURE:
<223> OTHER INFORMATION: Humanized antibody 36G9.10hz92/36G9.10hz93
      heavy chain variable region

<400> SEQUENCE: 17

Glu Val Gln Leu Val Gln Ser Gly Ala Glu Val Lys Lys Pro Gly Ala
             1               5                  10                  15

Thr Val Lys Ile Ser Cys Lys Ala Ser Gly Phe Asn Ile Lys Asp Thr
                            20                  25                  30

Tyr Ile His Trp Val Gln Gln Ala Pro Gly Lys Gly Leu Glu Trp Ile
                        35                  40                  45

Gly Arg Ile Asp Pro Ala Asn Asp Asn Thr Lys Tyr Asp Pro Lys Phe
```

```
                    50                  55                  60
Gln Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Gln Asp Tyr Asp Gly Phe Ala Met Asp Tyr Trp Gly Gln Gly Thr
            100                 105                 110

Leu Val Thr Val Ser Ser
        115

<210> SEQ ID NO 18
<211> LENGTH: 106
<212> TYPE: PRT
<213> ORGANISM: Artificial Sequence
<220> FEATURE:
<223> OTHER INFORMATION: Humanized antibody
      36G9.10hz43/36G9.10hz73/36G9.10hz93 light chain variable region

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Lys Tyr
                20                  25                  30

Ile Thr Trp Phe Gln Gln Lys Pro Gly Lys Ala Pro Lys Leu Leu Ile
             35                  40                  45

His Tyr Thr Ser Thr Leu Gln Pro Gly Val Pro Ser Arg Phe Ser Gly
         50                  55                  60

Ser Gly Ser Gly Arg Asp Tyr Thr Leu Thr Ile Ser Ser Leu Gln Pro
 65                  70                  75                  80

Glu Asp Phe Ala Thr Tyr Tyr Cys Leu Gln Tyr Asp Tyr Leu Leu Thr
                 85                  90                  95

Phe Gly Gly Gly Thr Lys Val Glu Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Humanized antibody 36G9.10hz92 light chain
      variable region

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Lys Tyr
                20                  25                  30

Ile Thr Trp Phe Gln Gln Lys Pro Gly Lys Ala Pro Lys Leu Leu Ile
             35                  40                  45

His Tyr Thr Ser Thr Leu Gln Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Tyr Leu Leu Thr
                 85                  90                  95

Phe Gly Gly Gly Thr Lys Val Glu Ile Lys
            100                 105
```

```
<210> SEQ ID NO 20
<211> LENGTH: 106
<212> TYPE: PRT
<213> ORGANISM: Artificial Sequence
<220> FEATURE:
<223> OTHER INFORMATION: Humanized antibody 36G9.10hz74 light chain
      variable region

<400> SEQUENCE: 20

Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Thr Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Tyr Leu Leu Thr
                85                  90                  95

Phe Gly Gly Gly Thr Lys Val Glu Ile Lys
            100                 105

<210> SEQ ID NO 21
<211> LENGTH: 330
<212> TYPE: PRT
<213> ORGANISM: Artificial Sequence
<220> FEATURE:
<223> OTHER INFORMATION: Human IgG1 heavy chain constant region (N297A
      mutant)

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 107
<212> TYPE: PRT
<213> ORGANISM: Artificial Sequence
<220> FEATURE:
<223> OTHER INFORMATION: Human kappa light chain constant region

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 23
<211> LENGTH: 354
<212> TYPE: DNA
<213> ORGANISM: Artificial Sequence
<220> FEATURE:
<223> OTHER INFORMATION: Humanized antibody 36G9.10hz73 heavy chain
      variable region nucleotide sequence

<400> SEQUENCE: 23
gaagtgcagc tggttcagtc tggcgccgaa gtgaagaaac tggcgctac cgtgaagatc      60 tcctgcaagg cctccggctt caacatcaag gacacctaca tccactgggt gcagcaggcc    120
cctggcaaag gattggagtg gatgggcaga atcgacccg ccaacgacaa caccatctac    180
gccgagaagt tccagggcag agtgaccatc accgccgaca cctctaccaa caccgcctac    240
atggaactgt ccagcctgag atctgaggac accgccgtgt actactgcgc ccaggattac    300
gatggcttcg ccatggatta ttggggccag ggcacactgg tcaccgtgtc atct          354
```

<210> SEQ ID NO 24
<211> LENGTH: 318
<212> TYPE: DNA
<213> ORGANISM: Artificial Sequence
<220> FEATURE:
<223> OTHER INFORMATION: Humanized antibody 36G9.10hz73 light chain
      variable region nucleotide sequence

<400> SEQUENCE: 24

| | | | | | |
|---|---|---|---|---|---|
| gacatccaga | tgacccagtc | tccatcctct | ctgtccgcct | ctgtgggcga | cagagtgacc | 60 |
| atcacatgca | aggccagcca | ggacatcaac | aagtacatca | cctggttcca | gcagaagccc | 120 |
| ggcaaggctc | ctaagctgct | gatccactac | acctccacac | tgcagcctgg | cgtgccctct | 180 |
| agattttccg | gctctggctc | tggccgggac | tataccctga | caatcagctc | tctgcagccc | 240 |
| gaggacttcg | ccacctacta | ctgcctgcag | tacgactacc | tgctgacctt | tggcggaggc | 300 |
| accaaggtgg | aaatcaag | | | | | 318 |

<210> SEQ ID NO 25
<211> LENGTH: 1344
<212> TYPE: DNA
<213> ORGANISM: Artificial Sequence
<220> FEATURE:
<223> OTHER INFORMATION: Humanized antibody 36G9.10hz73 heavy chain full
      length nucleotide sequence

<400> SEQUENCE: 25

| | | | | | |
|---|---|---|---|---|---|
| gaagtgcagc | tggttcagtc | tggcgccgaa | gtgaagaaac | tggcgcgtac | cgtgaagatc | 60 |
| tcctgcaagg | cctccggctt | caacatcaag | gacacctaca | tccactgggt | gcagcaggcc | 120 |
| cctggcaaag | gattggagtg | gatgggcaga | atcgaccccg | ccaacgacaa | caccatctac | 180 |
| gccgagaagt | tccagggcag | agtgaccatc | accgccgaca | cctctaccaa | caccgcctac | 240 |
| atggaactgt | ccagcctgag | atctgaggac | accgccgtgt | actactgcgc | caggattac | 300 |
| gatggcttcg | ccatggatta | ttggggccag | ggcacactgg | tcaccgtgtc | atctgctagc | 360 |
| accaagggac | cagcgttttt | ccctctggct | ccatcctcca | agagcacctc | tggtggaaca | 420 |
| gctgctctgg | gctgcctggt | caaggactac | tttcctgagc | ctgtgaccgt | gtcctggaac | 480 |
| tctggcgctc | tgacatctgg | cgtgcacacc | tttccagctg | tgctgcagtc | ctctggcctg | 540 |
| tactctctgt | cctccgtcgt | gaccgtgcct | tctagctctc | tgggcaccca | gacctacatc | 600 |
| tgcaatgtga | accacaagcc | ttccaacacc | aaggtggaca | agaaggtgga | acccaagtcc | 660 |
| tgcgacaaga | cccacacctg | tcctccatgt | cctgctccag | aactgctcgg | cggaccttcc | 720 |
| gtgttcctgt | tcctccaaa | gcctaaggac | accctgatga | tctctcggac | ccctgaagtg | 780 |
| acctgcgtgg | tggtggatgt | gtctcacgag | gacccagaaa | tgaagttcaa | ttggtacgtg | 840 |
| gacggcgtgg | aagtgcacaa | cgccaagacc | aagcctagag | aggaacagta | cgcctccacc | 900 |
| tacagagtgg | tgtccgtgct | gaccgtgctg | caccaggatt | ggctgaacgg | caaagagtac | 960 |
| aagtgcaagg | tgtccaacaa | ggccctgcct | gctcctatcg | aaaagaccat | ctccaaggcc | 1020 |
| aagggccagc | ctagagaacc | ccaggtttac | accttgcctc | catctcggga | cgagctgacc | 1080 |
| aagaaccagg | tgtccctgac | ctgtctcgtg | aagggcttct | accctccga | tatcgccgtg | 1140 |
| gaatgggagt | ctaatggcca | gcctgagaac | aactacaaga | caccccctcc | tgtgctggac | 1200 |
| tccgacggct | cattcttcct | gtactccaag | ctgacagtgg | acaagtccag | atggcagcag | 1260 |
| ggcaacgtgt | tctcctgctc | cgtgatgcac | gaggccctgc | acaatcacta | cacacagaag | 1320 |

| tccctgtctc tgtcccctgg caag | 1344 |

<210> SEQ ID NO 26
<211> LENGTH: 639
<212> TYPE: DNA
<213> ORGANISM: Artificial Sequence
<220> FEATURE:
<223> OTHER INFORMATION: Humanized antibody 36G9.10hz73 light chain full
length nucleotide sequence

<400> SEQUENCE: 26

| gacatccaga tgacccagtc tccatcctct ctgtccgcct ctgtgggcga cagagtgacc | 60 |
| atcacatgca aggccagcca ggacatcaac aagtacatca cctggttcca gcagaagccc | 120 |
| ggcaaggctc ctaagctgct gatccactac acctccacac tgcagcctgg cgtgccctct | 180 |
| agattttccg gctctggctc tggccgggac tatacccctg caatcagctc tctgcagccc | 240 |
| gaggacttcg ccacctacta ctgcctgcag tacgactacc tgctgacctt ggcggaggc | 300 |
| accaaggtgg aaatcaagcg tacggtggct gcaccatctg tcttcatctt cccgccatct | 360 |
| gatgagcagt tgaaatctgg aactgcctct gttgtgtgcc tgctgaataa cttctatccc | 420 |
| cgcgaggcca agtacagtg gaaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaaccgc ggagagtgt | 639 |

<210> SEQ ID NO 27
<211> LENGTH: 354
<212> TYPE: DNA
<213> ORGANISM: Artificial Sequence
<220> FEATURE:
<223> OTHER INFORMATION: Murine antibody 36G9.10 heavy chain variable
region nucleotide sequence

<400> SEQUENCE: 27

| gaggttcagc tgcagcagtc tggggcagag cttgtgaagc caggggcctc agtcaagttg | 60 |
| tcctgcacag cttctggctt caacattaaa gacacctata cactgggt gaaacagagg | 120 |
| cctgaacagg gcctggagtg gattggaagg attgatcctg cgaatgataa tactaaatat | 180 |
| gacccgaagt tccagggcaa ggccactata acagcagaca catcctccaa cacagcctac | 240 |
| ctgcagctca gcagcctgac atctgaggac tctgccgtct attactgtgc tcaagattac | 300 |
| gacgggtttg ctatggacta ctggggtcaa ggaacctcag tcaccgtctc ctca | 354 |

<210> SEQ ID NO 28
<211> LENGTH: 318
<212> TYPE: DNA
<213> ORGANISM: Artificial Sequence
<220> FEATURE:
<223> OTHER INFORMATION: Murine antibody 36G9.10 light chain variable
region nucleotide sequence

<400> SEQUENCE: 28

| gacatccaga tgacccagtc tccatcctca ctgtctgcat ctctgggagg caaagtcacc | 60 |
| atcacttgca aggcaagcca agacattaac aagtatataa cttggttcca acacaagcct | 120 |
| ggaaaaggtc ctaggctgct catacattac acatctacat acagccagg catcccatca | 180 |
| cggttcagtg aagtgggtc tgggagagat tattccttca gcatcagcaa tctggagcct | 240 |
| gaagatagtg caacttatta ttgtcttcag tatgattatc ttctgacgtt cggtggaggc | 300 | accaagctgg aaatcaaa  318

```
<210> SEQ ID NO 29
<211> LENGTH: 120
<212> TYPE: PRT
<213> ORGANISM: Artificial Sequence
<220> FEATURE:
<223> OTHER INFORMATION: Murine antibody 7B2 heavy chain variable region

<400> SEQUENCE: 29
```

Glu Val Gln Leu Gln Gln Ser Gly Ala Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Arg Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Lys Asp Arg Tyr Asp Ile Ser Leu Ser Met Asp Tyr Trp Gly Gln
            100                 105                 110

Gly Thr Ser Val Thr Val Ser Ser
        115                 120

```
<210> SEQ ID NO 30
<211> LENGTH: 107
<212> TYPE: PRT
<213> ORGANISM: Artificial Sequence
<220> FEATURE:
<223> OTHER INFORMATION: Murine antibody 7B2 light chain variable region

<400> SEQUENCE: 30
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Ile Ile Ser Asn Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105

```
<210> SEQ ID NO 31
<211> LENGTH: 120
<212> TYPE: PRT
<213> ORGANISM: Artificial Sequence
<220> FEATURE:
<223> OTHER INFORMATION: Humanized antibody 7B2hz11 heavy chain variable
      region sequence

<400> SEQUENCE: 31
```

Glu Val Gln Leu Val Gln Ser Gly Ala Glu Val Lys Lys Pro Gly Ala

```
                1               5                      10                      15
            Thr Val Lys Ile Ser Cys Lys Ala Ser Gly Tyr Ser Phe Thr Ser Tyr
                            20                      25                      30

Trp Met His Trp Val Gln Gln Ala Pro Gly Lys Gly Leu Glu Trp Met
                            35                      40                      45

Gly Ala Ile Tyr Pro Gly Asn Ser Asp Thr Ile Tyr Ala Glu Lys Phe
                            50                      55                      60

Gln Gly Arg Val Thr Ile Thr Ala Asp Thr Ser Thr Asp Thr Ala Tyr
             65                      70                      75                      80

Met Glu Leu Ser Ser Leu Arg Ser Glu Asp Thr Ala Val Tyr Tyr Cys
                            85                      90                      95

Thr Lys Asp Arg Tyr Asp Ile Ser Leu Ser Met Asp Tyr Trp Gly Gln
                            100                     105                     110

Gly Thr Leu Val Thr Val Ser Ser
                            115                     120

<210> SEQ ID NO 32
<211> LENGTH: 107
<212> TYPE: PRT
<213> ORGANISM: Artificial Sequence
<220> FEATURE:
<223> OTHER INFORMATION: Humanized antibody 7B2hz11 light chain variable
      region sequence

<400> SEQUENCE: 32

Asp Ile Gln Met Thr Gln Ser Pro Ser Ser Leu Ser Ala Ser Val Gly
             1               5                      10                      15

Asp Arg Val Thr Ile Thr Cys Arg Ala Ser Gln Asp Ile Ser Asn Tyr
                            20                      25                      30

Leu Asn Trp Tyr Gln Gln Lys Pro Gly Lys Ala Pro Lys Leu Leu Ile
                            35                      40                      45

Tyr Tyr Thr Ser Arg Leu His Ser Gly Val Pro Ser Arg Phe Ser Gly
                            50                      55                      60

Ser Gly Ser Gly Thr Asp Phe Thr Leu Thr Ile Ser Ser Leu Gln Pro
             65                      70                      75                      80

Glu Asp Phe Ala Thr Tyr Phe Cys Gln Gln Asn Thr Leu Pro Arg
                            85                      90                      95

Thr Phe Gly Gly Gly Thr Lys Val Glu Ile Lys
                            100                     105

<210> SEQ ID NO 33
<211> LENGTH: 8
<212> TYPE: PRT
<213> ORGANISM: Artificial Sequence
<220> FEATURE:
<223> OTHER INFORMATION: IMGT 7B2 CDR-H1

<400> SEQUENCE: 33

Gly Tyr Ser Phe Thr Ser Tyr Trp
             1               5

<210> SEQ ID NO 34
<211> LENGTH: 8
<212> TYPE: PRT
<213> ORGANISM: Artificial Sequence
<220> FEATURE:
<223> OTHER INFORMATION: IMGT 7B2 CDR-H2

<400> SEQUENCE: 34

Ile Tyr Pro Gly Asn Ser Asp Thr
```

```
<210> SEQ ID NO 35
<211> LENGTH: 13
<212> TYPE: PRT
<213> ORGANISM: Artificial Sequence
<220> FEATURE:
<223> OTHER INFORMATION: IMGT 7B2 CDR-H3

<400> SEQUENCE: 35

Thr Lys Asp Arg Tyr Asp Ile Ser Leu Ser Met Asp Tyr
1               5                   10

<210> SEQ ID NO 36
<211> LENGTH: 6
<212> TYPE: PRT
<213> ORGANISM: Artificial Sequence
<220> FEATURE:
<223> OTHER INFORMATION: IMGT 7B2 CDR-L1

<400> SEQUENCE: 36

Gln Asp Ile Ser Asn Tyr
1               5

<210> SEQ ID NO 37
<211> LENGTH: 3
<212> TYPE: PRT
<213> ORGANISM: Artificial Sequence
<220> FEATURE:
<223> OTHER INFORMATION: IMGT 7B2 CDR-L2

<400> SEQUENCE: 37

Tyr Thr Ser
1

<210> SEQ ID NO 38
<211> LENGTH: 9
<212> TYPE: PRT
<213> ORGANISM: Artificial Sequence
<220> FEATURE:
<223> OTHER INFORMATION: IMGT 7B2 CDR-L3

<400> SEQUENCE: 38

Gln Gln Gly Asn Thr Leu Pro Arg Thr
1               5

<210> SEQ ID NO 39
<211> LENGTH: 10
<212> TYPE: PRT
<213> ORGANISM: Artificial Sequence
<220> FEATURE:
<223> OTHER INFORMATION: AbM 7B2 CDR-H1

<400> SEQUENCE: 39

Gly Tyr Ser Phe Thr Ser Tyr Trp Met His
1               5                   10

<210> SEQ ID NO 40
<211> LENGTH: 10
<212> TYPE: PRT
<213> ORGANISM: Artificial Sequence
<220> FEATURE:
<223> OTHER INFORMATION: AbM 7B2 CDR-H2

<400> SEQUENCE: 40

Ala Ile Tyr Pro Gly Asn Ser Asp Thr Arg
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: AbM 7B2 CDR-H3

<400> SEQUENCE: 41

Asp Arg Tyr Asp Ile Ser Leu Ser Met Asp Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: AbM 7B2 CDR-L1

<400> SEQUENCE: 42

Arg Ala Ser Gln Asp Ile Ser Asn Tyr Leu Asn
1               5                   10

<210> SEQ ID NO 43
<211> LENGTH: 7
<212> TYPE: PRT
<213> ORGANISM: Artificial Sequence
<220> FEATURE:
<223> OTHER INFORMATION: AbM 7B2 CDR-L2

<400> SEQUENCE: 43

Tyr Thr Ser Arg Leu His Ser
1               5

<210> SEQ ID NO 44
<211> LENGTH: 9
<212> TYPE: PRT
<213> ORGANISM: Artificial Sequence
<220> FEATURE:
<223> OTHER INFORMATION: AbM 7B2 CDR-L3

<400> SEQUENCE: 44

Gln Gln Gly Asn Thr Leu Pro Arg Thr
1               5

<210> SEQ ID NO 45
<211> LENGTH: 10
<212> TYPE: PRT
<213> ORGANISM: Artificial Sequence
<220> FEATURE:
<223> OTHER INFORMATION: AbM 36G9.10hz73/36G9.10hz74 CDR-H2

<400> SEQUENCE: 45

Arg Ile Asp Pro Ala Asn Asp Asn Thr Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: AbM 36G9.10hz43 CDR-H2

<400> SEQUENCE: 46

Arg Ile Asp Pro Ala Asn Asp Asn Thr Asn
1               5                   10

```
<210> SEQ ID NO 47
<211> LENGTH: 10
<212> TYPE: PRT
<213> ORGANISM: Artificial Sequence
<220> FEATURE:
<223> OTHER INFORMATION: AbM 7B2hz11 CDR-H2

<400> SEQUENCE: 47

Ala Ile Tyr Pro Gly Asn Ser Asp Thr Ile
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Linker

<400> SEQUENCE: 48

Gly Gly Gly Gly Ser
1               5

<210> SEQ ID NO 49
<211> LENGTH: 20
<212> TYPE: PRT
<213> ORGANISM: Artificial Sequence
<220> FEATURE:
<223> OTHER INFORMATION: Linker

<400> SEQUENCE: 49

Gly Gly Gly Gly Ser Gly Gly Gly Gly Ser Gly Gly Gly Gly Ser Gly
1               5                   10                  15

Gly Gly Gly Ser
            20
```

ANTI-FXI/FXIA ANTIBODY AND USE THEREOF

CROSS REFERENCE TO RELATED APPLICATIONS

This application is a national stage application under 35 U.S.C. § 371 of International Application No. PCT/CN2020/083413, filed internationally on Apr. 6, 2020, which claims priority to Chinese Application No. 201910303627.7, filed on Apr. 16, 2019, the contents of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952000400SEQLIST.TXT, date recorded: Aug. 16, 2021, size: 28,834 bytes).

TECHNICAL FIELD

The present invention relates to the field of therapeutic monoclonal antibodies. More specifically, the present invention relates to an antibody against FXI and/or FXIa, and a use of the antibody for the prevention and/or treatment of a disease or disorder associated with coagulation or thromboembolism.

BACKGROUND ART

Thrombosis or embolism involves diseases of various organs of the whole body, mainly heart, brain and peripheral vascular diseases. It has the characteristics of high incidence, high disability and lethality, and is the first cause of death caused by cardiovascular diseases. At present, the prevention and treatment drugs for thrombotic diseases mainly include three types, i.e., anticoagulant, antiplatelet and thrombolytic drugs. Anticoagulant drugs are mainly used to prevent and treat venous thromboembolism caused by various reasons and they can also be used for prevention of stroke in patients with atrial fibrillation and for anticoagulant therapy in patients with acute coronary syndrome. There is a large market demand for anticoagulant drugs, and there are drugs available for clinical use. However, the current clinically used anticoagulant drugs mainly inhibit the common pathway of the coagulation cascade, that's why bleeding is the main complication. Traditional anticoagulant drugs, such as warfarin, heparin, low molecular weight heparin, and new drugs that have been on the market in recent years, such as FXa inhibitors (rivaroxaban, apixaban, etc.) and thrombin inhibitors (dabigatran etexilate, hirudin, etc.), all have good effects on reducing thrombosis, but they all face a common deficiency, that is, they may cause bleeding complications. Therefore, there is an urgent clinical need for anticoagulant drugs with low bleeding risk.

Coagulation factor XI (FXI) participates in the endogenous coagulation cascade, and its active form is coagulation factor XIa (FXIa). FXI protein is a dimer formed by two homologous monomers with a molecular weight of about 80 kDa through disulfide bond. The FXI monomer is composed of four apple domains and one catalytic domain, and catalyzed by coagulation factor XIIa (FXIIa) to form FXIa with exposed binding site for FIX, which will bind to FIX and then promotes the conversion of FIX into active FIXa, thereby activating the downstream coagulation cascade. The coagulation factor XI has a concentration of about 25-30 nM in mammalian plasma and is a glycoprotein in the form of zymogen, and almost all FXI forms a complex with high molecular weight kininogen (HK) and circulates in the blood. The impact of HK on FXI functions is still unclear so far. HK may assist FXI to bind to surfaces of platelets or endothelial cells, and HK has also been observed to inhibit the activation of FXI. The activation process of FXI comprises, under the action of different proteases, each monomer is cleaved between Arg369-Ile370 to produce a protein, which consists of a heavy chain of about 50 kDa comprising an apple domain and a light chain of about 30 kDa comprising a catalytic domain, and the heavy chain and the light chain are connected by the disulfide bond formed between Cys362-Cys482. Activated FXI, i.e., FXIa, usually refers to a case where each monomer of the dimer FXI is cleaved at Arg369, but only one monomer is activated. FXIa cleaves FIX with the participation of $Ca^{2+}$, turning it into activated FIX (FIXa), which then converts coagulation factor X into its active form Xa. Xa can then mediate coagulation factor II/thrombin activation. Thrombin, as the terminal protease in the coagulation cascade, can further promote the production of FXIa by directly activating FXI through a feedback mechanism. Both coagulation factors XIIa and FXIa (self-activation) in the coagulation cascade can convert FXI to FXIa.

In addition, activated FIX (FIXa) can directly bind to platelets, promote the formation of platelet aggregates in the blood, and form distal microvascular occlusion. Therefore, FIX/FIXa promotes thrombosis through a variety of ways. And animal experiments and clinical observations show that the lack of FIX/FIXa has only a minimal risk of bleeding. Therefore, FIX/FIXa is an ideal target for preventing and treating diseases/disorders associated with coagulation or thromboembolism. (Zilberman-Rudenko J. et. al. Coagulation factor XI promotes distal platelet activation and single platelet consumption in the bloodstream under shear flow. Arterioscler Thromb Vasc Biol. 2016 March; 36(3): 510-517). The factors that regulate the coagulation function through the intervention of FXI and/or FXIa molecules include, but are not limited to: forming FXI and/or FXIa dimers; blocking the contact between the molecule which can activate FXI (e.g., coagulation factors XIIa, FXIa) and FXI, thereby inhibiting or blocking the activation of FXI; inhibiting or blocking the formation of complexes between FXI and HK; closing the catalytic domain of FXI and/or FXIa, or inducing a conformational change in the catalytic domain, thereby inactivating FXI and/or FXIa, thereby inhibiting or preventing the activation of the intrinsic coagulation pathway; inhibiting or blocking the binding of FXI and/or FXIa to its substrate.

At present, Bayer's FXIa antibody drug BAY-1213790 is in phase II clinical trials for venous embolism indication. BAY-1213790 comes from a phage display library and binds to the FXIa catalytic domain. In addition, Aronora's AB-023 (14E11) is in clinical phase I for venous thrombosis indication, and in clinical phase II for end-stage renal disease (ESRD) indication.

Currently, there is not a FXIa-targeting antibody drug on the market. Therefore, it is urgent and necessary to develop an anti-FXI and/or FXIa antibody with higher specificity, lower toxic and side effects, better clinical efficacy, and more convenient administration methods, and this will provide patients with more medication options.

CONTENTS OF THE PRESENT INVENTION

In the present application, the inventors first developed a murine antibody with excellent properties, which can specifically recognize FXI and/or FXIa. On this basis, the inventors had paid a lot of creative work to carry out in-depth research and modification of the murine antibody, thereby developing a humanized antibody thereof.

The antibody of the present invention (especially the humanized antibody) is extremely advantageous, which not only retains (or even improves) the functions and properties of the parent murine antibody, for example, to bind FXI and/or FXIa with high affinity and specificity, thereby having the potential to be used for the prevention and treatment of coagulation or thromboembolic disorders, but also has a very high degree of humanization and can be safely administered to human subjects without triggering an immunogenic response. Therefore, the antibody of the present invention has great clinical value.

Antibodies of the Present Invention

In one aspect, the present invention provides an antibody or antigen-binding fragment thereof capable of specifically binding to FXI and/or FXIa, wherein the antibody or antigen-binding fragment thereof comprises the following:
  (a) three heavy chain CDRs as follows: CDR-H1, CDR-H2 and CDR-H3 contained in the heavy chain variable region (VH) as shown in any one of SEQ ID NOs: 1, 15, 16, 17, 29, 31; and/or
  three light chain CDRs as follows: CDR-L1, CDR-L2 and CDR-L3 contained in the light chain variable region (VL) as shown in any one of SEQ ID NOs: 2, 18, 19, 20, 30, 32;
  or,
  (b) three heavy chain CDRs as follows: the CDR-H1 described in (a) or a variant comprising an amino acid mutation as compared thereto, the CDR-H2 described in (a) or a variant comprising an amino acid mutation as compared thereto, the CDR-H3 described in (a) or a variant comprising an amino acid mutation as compared thereto; and/or
  three light chain CDRs as follows: the CDR-L1 described in (a) or a variant comprising an amino acid mutation as compared thereto, the CDR-L2 described in (a) or a variant comprising an amino acid mutation as compared thereto, the CDR-L3 described in (a) or a variant comprising an amino acid mutation as compared thereto;
  wherein at least one CDR of the three heavy chain CDRs and/or three light chain CDRs described in (b) contains an amino acid mutation as compared to the corresponding CDR in (a), and the amino acid mutation is a substitution, deletion or addition of one or several amino acids (e.g., a substitution, deletion or addition of 1, 2, or 3 amino acids).

In certain preferred embodiments, the substitution is a conservative substitution.

In certain preferred embodiments, the CDRs of the antibody or antigen-binding fragment thereof are defined according to the Kabat, IMGT, Chothia or AbM numbering system.

In certain preferred embodiments, the antibody or antigen-binding fragment thereof further comprises framework regions (FRs) of immunoglobulin derived from a human or murine.

In certain preferred embodiments, the antibody or antigen-binding fragment thereof binds to a human FXI and/or human FXIa.

In certain embodiments, the antibody or antigen-binding fragment thereof comprises:
  (a) three heavy chain CDRs as follows: CDR-H1, CDR-H2 and CDR-H3 contained in the heavy chain variable region (VH) as shown in any one of SEQ ID NOs: 1, 15, 16, 17; and/or
  three light chain CDRs as follows: CDR-L1, CDR-L2 and CDR-L3 contained in the light chain variable region (VL) as shown in any one of SEQ ID NOs: 2, 18, 19, 20;
  or,
  (b) three heavy chain CDRs as follows: the CDR-H1 described in (a) or a variant comprising an amino acid mutation as compared thereto, the CDR-H2 described in (a) or a variant comprising an amino acid mutation as compared thereto, the CDR-H3 described in (a) or a variant comprising an amino acid mutation as compared thereto; and/or
  three light chain CDRs as follows: the CDR-L1 described in (a) or a variant comprising an amino acid mutation as compared thereto, the CDR-L2 described in (a) or a variant comprising an amino acid mutation as compared thereto, the CDR-L3 described in (a) or a variant comprising an amino acid mutation as compared thereto;
  wherein at least one CDR of the three heavy chain CDRs and/or three light chain CDRs described in (b) contains an amino acid mutation as compared to the corresponding CDR in (a), and the amino acid mutation is a substitution, deletion or addition of one or several amino acids (e.g., a substitution, deletion or addition of 1, 2, or 3 amino acids); in certain preferred embodiments, the substitution is a conservative substitution.

In certain embodiments, the antibody or antigen-binding fragment thereof comprises:
  (a) three heavy chain CDRs as follows: CDR-H1, CDR-H2 and CDR-H3 contained in the heavy chain variable region (VH) as shown in any one of SEQ ID NOs: 29, 31; and/or
  three light chain CDRs as follows: CDR-L1, CDR-L2 and CDR-L3 contained in the light chain variable region (VL) as shown in any one of SEQ ID NOs: 30, 32;
  or,
  (b) three heavy chain CDRs as follows: the CDR-H1 described in (a) or a variant comprising an amino acid mutation as compared thereto, the CDR-H2 described in (a) or a variant comprising an amino acid mutation as compared thereto, the CDR-H3 described in (a) or a variant comprising an amino acid mutation as compared thereto; and/or
  three light chain CDRs as follows: the CDR-L1 described in (a) or a variant comprising an amino acid mutation as compared thereto, the CDR-L2 described in (a) or a variant comprising an amino acid mutation as compared thereto, the CDR-L3 described in (a) or a variant comprising an amino acid mutation as compared thereto;
  wherein at least one CDR of the three heavy chain CDRs and/or three light chain CDRs described in (b) contains an amino acid mutation as compared to the corresponding CDR in (a), and the amino acid mutation is a substitution, deletion or addition of one or several amino acids (e.g., a substitution, deletion or addition of 1, 2, or 3 amino acids); in certain preferred embodiments, the substitution is a conservative substitution.

In certain embodiments, the antibody or antigen-binding fragment thereof comprises: a heavy chain variable region (VH) and/or a light chain variable region (VL).

In certain embodiments, the antibody or antigen-binding fragment thereof according to the present invention comprises a heavy chain variable region (VH) and/or a light chain variable region (VL) as follows, wherein the CDRs are defined by the IMGT numbering system:
- (a) a heavy chain variable region (VH) comprising three CDRs as follows: CDR-H1 with the sequence of SEQ ID NO: 3, CDR-H2 with the sequence of SEQ ID NO: 4, and CDR-H3 with the sequence of SEQ ID NO: 5; and/or,
  a light chain variable region (VL) comprising three CDRs as follows: CDR-L1 with the sequence of SEQ ID NO: 6, CDR-L2 with the sequence of SEQ ID NO: 7, and CDR-L3 with the sequence of SEQ ID NO: 8;
  or
- (b) a heavy chain variable region (VH) comprising three CDRs as follows: CDR-H1 with the sequence of SEQ ID NO: 33, CDR-H2 with the sequence of SEQ ID NO: 34, and CDR-H3 with the sequence of SEQ ID NO: 35; and/or,
  a light chain variable region (VL) comprising three CDRs as follows: CDR-L1 with the sequence of SEQ ID NO: 36, CDR-L2 with the sequence of SEQ ID NO: 37, and CDR-L3 with the sequence of SEQ ID NO: 38.

In certain embodiments, the antibody or antigen-binding fragment thereof according to the present invention comprises a heavy chain variable region (VH) and/or a light chain variable region (VL), wherein at least one CDR of the heavy chain variable region (VH) and/or light chain variable region (VL) comprises an amino acid mutation as compared with the heavy chain variable region and/or light chain variable region described in (a) or (b) under IMGT definition, and the amino acid mutation is a substitution, deletion or addition of one or several amino acids or any combination thereof (e.g., a substitution, deletion or addition of 1, 2 or 3 amino acids or any combination thereof); preferably, the substitution is a conservative substitution.

In certain embodiments, the antibody or antigen-binding fragment thereof according to the present invention comprises a heavy chain variable region (VH) and/or a light chain variable region (VL) as follows, wherein the CDRs are defined by the AbM numbering system:
- (a) a heavy chain variable region (VH) comprising three CDRs as follows: CDR-H1 with the sequence of SEQ ID NO: 9, CDR-H2 with the sequence of SEQ ID NO: 10, 45 or 46, and CDR-H3 with the sequence of SEQ ID NO: 11; and/or,
  a light chain variable region (VL) comprising three CDRs as follows: CDR-L1 with the sequence of SEQ ID NO: 12, CDR-L2 with the sequence of SEQ ID NO: 13, and CDR-L3 with the sequence of SEQ ID NO: 14;
  or
- (b) a heavy chain variable region (VH) comprising three CDRs as follows: CDR-H1 with the sequence of SEQ ID NO: 39, CDR-H2 with the sequence of SEQ ID NO: 40 or 47, and CDR-H3 with the sequence of SEQ ID NO: 41; and/or,
  a light chain variable region (VL) comprising three CDRs as follows: CDR-L1 with the sequence of SEQ ID NO: 42, CDR-L2 with the sequence of SEQ ID NO: 43, and CDR-L3 with the sequence of SEQ ID NO: 44.

In certain embodiments, the antibody or antigen-binding fragment thereof according to the present invention comprises a heavy chain variable region (VH) and/or a light chain variable region (VL), wherein at least one CDR of the heavy chain variable region (VH) and/or light chain variable region (VL) comprises an amino acid mutation as compared with the heavy chain variable region and/or light chain variable region described in (a) or (b) under AbM definition, and the amino acid mutation is a substitution, deletion or addition of one or several amino acids or any combination thereof (e.g., a substitution, deletion or addition of 1, 2 or 3 amino acids or any combination thereof); preferably, the substitution is a conservative substitution.

In certain embodiments, the antibody or antigen-binding fragment thereof according to the present invention comprises a heavy chain variable region (VH) and/or a light chain variable region (VL), wherein at least one CDR of the heavy chain variable region (VH) and/or light chain variable region (VL) comprises an amino acid mutation as compared with the heavy chain variable region and/or light chain variable region described in (a) or (b) under the IMGT or AbM definition, and the amino acid mutation is a substitution, deletion or addition of one or several amino acids or any combination thereof (e.g., a substitution, deletion or addition of 1, 2 or 3 amino acids or any combination thereof); preferably, the substitution is a conservative substitution.

In certain preferred embodiments, the antibody or antigen-binding fragment thereof according to the present invention has a VH comprising heavy chain variable region (VH) framework regions (FRs) derived from murine immunoglobulin, and/or the antibody or antigen-binding fragment thereof has a VL comprising light chain variable region (VL) framework regions (FRs) derived from murine immunoglobulin. Therefore, in certain preferred embodiments, the antibody or antigen-binding fragment thereof according to the present invention is derived from murine.

In certain preferred embodiments, the antibody or antigen-binding fragment thereof according to the present invention has a VH comprising heavy chain variable region (VH) framework regions (FRs) derived from human immunoglobulin, and/or the antibody or antigen-binding fragment thereof has a VL comprising light chain variable region (VL) framework regions (FRs) derived from human immunoglobulin. Therefore, in certain preferred embodiments, the antibody or antigen-binding fragment thereof according to the present invention is humanized. In such embodiments, the heavy chain variable region FRs and/or light chain variable region FRs of the antibody or antigen-binding fragment thereof according to the present invention may comprise one or more non-human (e.g., murine) amino acid residues, for example, the heavy chain framework region FRs and/or the light chain framework region FRs may comprise one or more amino acid back mutations, and these back mutations comprise corresponding murine amino acid residues.

In certain preferred embodiments, the antibody or antigen-binding fragment thereof according to the present invention comprises:
- (a) a human immunoglobulin heavy chain framework region or a variant thereof, wherein the variant has a conservative substitution of up to 20 amino acids (e.g., a conservative substitution of up to 15, up to 10, or up to 5 amino acids; for example, a conservative substitution of 1, 2, 3, 4 or 5 amino acids) as compared with a germline antibody gene sequence from which it is derived; and/or
- (b) a human immunoglobulin light chain framework region or a variant thereof, wherein the variant has a conservative substitution of up to 20 amino acids (e.g., a conservative substitution of up to 15, up to 10, or up to 5 amino acids; for example, a conservative substitution of 1, 2, 3, 4 or 5 amino acids) as compared with a germline antibody gene sequence from which it is derived.

In certain preferred embodiments, the antibody or antigen-binding fragment thereof according to the present invention has a humanization degree of at least 75%, at least 80%, at least 85%, at least 90%, at least 91%, at least 92%, at least 93%. %, at least 94%, at least 95%, at least 96%, at least 97%, at least 98%, at least 99%, or 100%.

In certain embodiments, the antibody or antigen-binding fragment thereof according to the present invention comprises:
(a) a heavy chain variable region (VH), which comprises an amino acid sequence selected from the following:
(i) the sequence as shown in any one of SEQ ID NOs: 1, 15, 16, 17;
(ii) a sequence having a substitution, deletion or addition of one or several amino acids or any combination thereof (e.g., a substitution, deletion or addition of 1, 2, 3, 4 or 5 amino acids or any combination thereof) as compared with the sequence shown in any one of SEQ ID NOs: 1, 15, 16, 17; or
(iii) a sequence having an identity of at least 75%, at least 80%, at least 85%, at least 90%, at least 91%, at least 92%, at least 93%, at least 94%, at least 95%, at least 96%, at least 97%, at least 98%, at least 99%, or 100% to the sequence shown in any one of SEQ ID NOs: 1, 15, 16, 17;
and/or
(b) a light chain variable region (VL), which comprises an amino acid sequence selected from the following:
(iv) the sequence shown in any one of SEQ ID NOs: 2, 18, 19, 20;
(v) a sequence having a substitution, deletion or addition of one or several amino acids or any combination thereof (e.g., a substitution, deletion or addition of 1, 2, 3, 4 or 5 amino acids or any combination thereof) as compared with the sequence shown in any one of SEQ ID NOs: 2, 18, 19, 20; or
(vi) a sequence having an identity of at least 75%, at least 80%, at least 85%, at least 90%, at least 91%, at least 92%, at least 93%, at least 94%, at least 95%, at least 96%, at least 97%, at least 98%, at least 99%, or 100% to the sequence shown in any one of SEQ ID NOs: 2, 18, 19, 20.

In certain embodiments, the antibody or antigen-binding fragment thereof according to the present invention comprises:
(a) a heavy chain variable region (VH), which comprises an amino acid sequence selected from the following:
(i) the sequence as shown in any one of SEQ ID NOs: 29, 31;
(ii) a sequence having a substitution, deletion or addition of one or several amino acids or any combination thereof (e.g., a substitution, deletion or addition of 1, 2, 3, 4 or 5 amino acids or any combination thereof) as compared with the sequence shown in any one of SEQ ID NOs: 29, 31;
or
(iii) a sequence having an identity of at least 75%, at least 80%, at least 85%, at least 90%, at least 91%, at least 92%, at least 93%, at least 94%, at least 95%, at least 96%, at least 97%, at least 98%, at least 99%, or 100% to the sequence shown in any one of SEQ ID NOs: 29, 31;
and/or
(b) a light chain variable region (VL), which comprises an amino acid sequence selected from the following:
(iv) the sequence shown in any one of SEQ ID NOs: 30, 32;
(v) a sequence having a substitution, deletion or addition of one or several amino acids or any combination thereof (e.g., a substitution, deletion or addition of 1, 2, 3, 4 or 5 amino acids or any combination thereof) as compared with the sequence shown in any one of SEQ ID NOs: 30, 32; or
(vi) a sequence having an identity of at least 75%, at least 80%, at least 85%, at least 90%, at least 91%, at least 92%, at least 93%, at least 94%, at least 95%, at least 96%, at least 97%, at least 98%, at least 99%, or 100% to the sequence shown in any one of SEQ ID NOs: 30, 32.

In certain embodiments, the antibody or antigen-binding fragment thereof according to the present invention has a heavy chain variable region (VH) and/or a light chain variable region (VL) as follows: the VH shown in any one of SEQ ID NOs: 1, 15, 16, 17, and/or the VL shown in any one of SEQ ID NOs: 2, 18, 19, 20.

In certain embodiments, the antibody or antigen-binding fragment thereof according to the present invention has a heavy chain variable region (VH) and/or a light chain variable region (VL) as follows: the VH shown in any one of SEQ ID NOs: 29, 31, and/or the VL shown in any one of SEQ ID NOs: 30, 32.

In certain embodiments, the antibody or antigen-binding fragment thereof according to the present invention comprises the VH shown in SEQ ID NO: 1, and/or the VL shown in SEQ ID NO: 2.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 1 and/or the VL shown in SEQ ID NO: 2.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 1 and/or the VL shown in SEQ ID NO: 2. In a preferred embodiment, the substitution is a conservative substitution.

In certain embodiments, the antibody or antigen-binding fragment thereof according to the present invention comprises the VH shown in SEQ ID NO: 15, and/or the VL shown in SEQ ID NO: 18.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 15 and/or the VL shown in SEQ ID NO: 18.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 15 and/or the VL shown in SEQ ID NO: 18. In a preferred embodiment, the substitution is a conservative substitution.

In certain embodiments, the antibody or antigen-binding fragment thereof according to the present invention comprises the VH shown in SEQ ID NO: 15, and/or the VL shown in SEQ ID NO: 20.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 15 and/or the VL shown in SEQ ID NO: 20.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 15 and/or the VL shown in SEQ ID NO: 20. In a preferred embodiment, the substitution is a conservative substitution.

In certain embodiments, the antibody or antigen-binding fragment thereof according to the present invention comprises the VH shown in SEQ ID NO: 16, and/or the VL shown in SEQ ID NO: 18.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 16 and/or the VL shown in SEQ ID NO: 18.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 16 and/or the VL shown in SEQ ID NO: 18. In a preferred embodiment, the substitution is a conservative substitution.

In certain embodiments, the antibody or antigen-binding fragment thereof according to the present invention comprises the VH shown in SEQ ID NO: 17, and/or the VL shown in SEQ ID NO: 19.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 17 and/or the VL shown in SEQ ID NO: 19.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 17 and/or the VL shown in SEQ ID NO: 19. In a preferred embodiment, the substitution is a conservative substitution.

In certain embodiments, the antibody or antigen-binding fragment thereof according to the present invention comprises the VH shown in SEQ ID NO: 17, and/or the VL shown in SEQ ID NO: 18.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 17 and/or the VL shown in SEQ ID NO: 18.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 17 and/or the VL shown in SEQ ID NO: 18. In a preferred embodiment, the substitution is a conservative substitution.

In certain embodiments, the antibody or antigen-binding fragment thereof according to the present invention comprises the VH shown in SEQ ID NO: 29, and/or the VL shown in SEQ ID NO: 30.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 29 and/or the VL shown in SEQ ID NO: 30.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 29 and/or the VL shown in SEQ ID NO: 30. In a preferred embodiment, the substitution is a conservative substitution.

In certain embodiments, the antibody or antigen-binding fragment thereof according to the present invention comprises the VH shown in SEQ ID NO: 31, and/or the VL shown in SEQ ID NO: 32.

In certain embodiments, the VH and/or VL of the antibody or antigen-binding fragment thereof according to the present invention has an identity of at least 70%, at least 80%, at least 85%, at least 90%, at least 91%, at least 92%, at least 93%, at least 94%, at least 95%, at least 96%, at least 97%, at least 98%, at least 99%, or 100% as compared to the VH shown in SEQ ID NO: 31 and/or the VL shown in SEQ ID NO: 32.

In certain embodiments, the VH and/or VL of the antibody or antigen-binding fragment thereof has a substitution, deletion or addition of one or several amino acids or any combination thereof (e.g., a substitution, deletion or addition of 1, 2, 3, 4 or 5 amino acids, or any combination thereof) as compared to the VH shown in SEQ ID NO: 31 and/or the VL shown in SEQ ID NO: 32. In a preferred embodiment, the substitution is a conservative substitution.

In certain preferred embodiments, the antibody or antigen-binding fragment thereof according to the present invention comprises:
(a) a VH having the sequence shown in SEQ ID NO: 1 and a VL having the sequence shown in SEQ ID NO: 2;
(b) a VH having the sequence shown in SEQ ID NO: 15 and a VL having the sequence shown in SEQ ID NO: 18;
(c) a VH having the sequence shown in SEQ ID NO: 15 and a VL having the sequence shown in SEQ ID NO: 20;

(d) a VH having the sequence shown in SEQ ID NO: 16 and a VL having the sequence shown in SEQ ID NO: 18;

(e) a VH having the sequence shown in SEQ ID NO: 17 and a VL having the sequence shown in SEQ ID NO: 19;

(f) a VH having the sequence shown in SEQ ID NO: 17 and a VL having the sequence shown in SEQ ID NO: 18;

(g) a VH having the sequence shown in SEQ ID NO: 29 and a VL having the sequence shown in SEQ ID NO: 30; or, (h) a VH having the sequence shown in SEQ ID NO: 31 and a VL having the sequence shown in SEQ ID NO: 32.

In certain preferred embodiments, the antibody or antigen-binding fragment thereof according to the present invention comprises a heavy chain variable region (VH) having an identity of at least 70%, at least 80%, at least 85%, at least 90%, at least 91%, at least 92%, at least 93%, at least 94%, at least 95%, at least 96%, at least 97%, at least 98%, at least 99%, or 100% to the VH described in any one of (a) to (h); and/or, the antibody or antigen-binding fragment thereof according to the present invention comprises a light chain variable region (VL) having an identity of at least 70%, at least 80%, at least 85%, at least 90%, at least 91%, at least 92%, at least 93%, at least 94%, at least 95%, at least 96%, at least 97%, at least 98%, at least 99%, or 100% to the VL described in any one of (a) to (h).

In certain preferred embodiments, the antibody or antigen-binding fragment thereof comprises a heavy chain variable region (VH) having a substitution, deletion or addition of one or several amino acids or any combination thereof (e.g., a substitution, deletion or addition of 1, 2, 3, 4 or 5 amino acids or any combination thereof) as compared to the VH in any one of (a) to (h); and/or the antibody or antigen-binding fragment thereof comprises a light chain variable region (VL) having a substitution, deletion or addition of one or several amino acids or any combination thereof (e.g., a substitution, deletion or addition of 1, 2, 3, 4 or 5 amino acids or any combination thereof) as compared to the VL in any one of (a) to (h); preferably, the substitution is a conservative substitution.

In any of the above aspects, the antibody or antigen-binding fragment thereof according to the present invention may further comprise a constant region sequence derived from a mammalian (e.g., murine or human) immunoglobulin or a variant thereof. In certain embodiments, the heavy chain of the antibody or antigen-binding fragment thereof according to the present invention comprises a heavy chain constant region (CH) of a human or murine immunoglobulin or a variant thereof, and the variant has a substitution, deletion or addition of one or several amino acids or any combination thereof (e.g., a substitution, deletion or addition of up to 20, up to 15, up to 10, or up to 5 amino acids, or any combination thereof; for example, a substitution, deletion or addition of 1, 2, 3, 4 or 5 amino acids, or any combination thereof) as compared to a wild type sequence from which it is derived; and/or the light chain of the antibody or antigen-binding fragment thereof according to the present invention comprises a light chain constant region (CL) of a human or murine immunoglobulin or a variant thereof, and the variant has a substitution, deletion or addition of one or several amino acids or any combination thereof (e.g., a substitution, deletion or addition of up to 20, up to 15, up to 10, or up to 5 amino acids, or any combination thereof; for example, a substitution, deletion or addition of 1, 2, 3, 4 or 5 amino acids, or any combination thereof) as compared to a wild type sequence from which it is derived.

In certain preferred embodiments, the heavy chain of the antibody or antigen-binding fragment thereof according to the present invention comprises a heavy chain constant region (CH) of a human immunoglobulin or a variant thereof, and the variant has a conservative substitution of up to 20 amino acids (e.g., a conservative substitution of up to 15, up to 10, or up to 5 amino acids; for example, a conservative substitution of 5, 4, 3, 2 or 1 amino acid) as compared to a wild type sequence from which it is derived; and/or, the light chain of the antibody or antigen-binding fragment thereof according to the present invention comprises a light chain constant region (CL) of a human immunoglobulin or a variant thereof, and the variant has a conservative substitution of up to 20 amino acids (e.g., a conservative substitution of up to 15, up to 10, or up to 5 amino acids; for example, a conservative substitution of 5, 4, 3, 2 or 1 amino acid) as compared to a wild type sequence from which it is derived.

In certain preferred embodiments, the heavy chain of the antibody or antigen-binding fragment thereof according to the present invention comprises a heavy chain constant region (CH) of a murine immunoglobulin or a variant thereof, and the variant has a conservative substitution of up to 20 amino acids (e.g., a conservative substitution of up to 15, up to 10, or up to 5 amino acids; for example, a conservative substitution of 5, 4, 3, 2 or 1 amino acid) as compared to a wild type sequence from which it is derived. In certain embodiments, the light chain of the antibody or antigen-binding fragment thereof according to the present invention comprises a light chain constant region (CL) of a murine immunoglobulin or a variant thereof, and the variant has a conservative substitution of up to 20 amino acids (e.g., a conservative substitution of up to 15, up to 10, or up to 5 amino acids; for example, a conservative substitution of 5, 4, 3, 2 or 1 amino acid) as compared to a wild type sequence from which it is derived.

In some embodiments, the constant region is altered, for example, by an amino acid mutation, to modify the properties of anti-FXI and/or FXIa antibody molecule (e.g., to alter one or more of the following properties: Fc receptor binding, antibody glycosylation, number of cysteine residues, functions on effector cells or complements). Such function alteration may be achieved by replacing at least one amino acid residue in the constant region of the antibody with a different residue, for example, the effector function may be changed (e.g., reduced) by changing the affinity of the antibody to an effector ligand (e.g., FcR or complement C1q). The Fc region of antibody mediates several important effector functions, such as ADCC, phagocytosis, CDC and so on.

In certain embodiments, the antibody or antigen-binding fragment thereof according to the present invention has a heavy chain constant region (Fc), which is selected from, for example, the heavy chain constant regions of IgG1, IgG2, IgG3, IgG4, IgM, IgA1, IgA2, IgD and IgE; preferably selected from, for example, the heavy chain constant regions of IgG1, IgG2, IgG3 and IgG4; more preferably selected from the heavy chain constant region of IgG1 or IgG4 (e.g., human IgG1 or IgG4). In some embodiments, the antibody or antigen-binding fragment thereof according to the present invention has a light chain constant region, which is selected from, for example, κ or λ light chain constant region, preferably κ light chain constant region (e.g., human κ light chain).

In some preferred embodiments, the antibody or antigen-binding fragment thereof comprises a heavy chain constant region selected from: (1) a human IgG1 heavy chain constant region; or (2) a human IgG4 heavy chain constant region.

In certain preferred embodiments, the antibody or antigen-binding fragment thereof according to the present invention comprises:
(a) a heavy chain constant region (CH), which comprises an amino acid sequence selected from the following:
(i) the sequence shown in SEQ ID NO: 21;
(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in SEQ ID NO: 21; or
(iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in SEQ ID NO: 21;
and/or
(b) a light chain constant region (CL), which comprises an amino acid sequence selected from the following:
(iv) the sequence shown in SEQ ID NO: 22;
(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in SEQ ID NO: 22; or
(vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in SEQ ID NO: 22.

In certain preferred embodiments, the substitution described in (ii) or (v) is a conservative substitution.

In certain preferred embodiments, the antibody or antigen-binding fragment thereof according to the present invention comprises a heavy chain constant region (CH) as shown in SEQ ID NO: 21 and a light chain constant region (CL) as shown in SEQ ID NO: 22.

In certain preferred embodiments, the antibody or antigen-binding fragment thereof according to the present invention comprises:
(a) a heavy chain, which comprises an amino acid sequence selected from:
(i) a sequence comprising the VH shown in SEQ ID NO: 15 and the CH shown in SEQ ID NO: 21;
(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (i); or
(iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (i);
and/or
(b) a light chain, which comprises an amino acid sequence selected from:
(iv) a sequence comprising the VL sequence shown in SEQ ID NO: 18 and the CL sequence shown in SEQ ID NO: 22;
(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (iv); or
(vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (iv).

In certain preferred embodiments, the substitution described in (ii) or (v) is a conservative substitution.

In certain preferred embodiments, the antibody or antigen-binding fragment thereof according to the present invention comprises:
(a) a heavy chain, which comprises an amino acid sequence selected from:
(i) a sequence comprising the VH shown in SEQ ID NO: 15 and the CH shown in SEQ ID NO: 21;
(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (i); or
(iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (i);
and/or
(b) a light chain, which comprises an amino acid sequence selected from:
(iv) a sequence comprising the VL sequence shown in SEQ ID NO: 20 and the CL sequence shown in SEQ ID NO: 22;
(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (iv); or
(vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (iv).

In certain preferred embodiments, the substitution described in (ii) or (v) is a conservative substitution.

In certain preferred embodiments, the antibody or antigen-binding fragment thereof according to the present invention comprises:
(a) a heavy chain, which comprises an amino acid sequence selected from:
(i) a sequence comprising the VH shown in SEQ ID NO: 16 and the CH shown in SEQ ID NO: 21;
(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (i); or
(iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (i);

and/or (b) a light chain, which comprises an amino acid sequence selected from:

(iv) a sequence comprising the VL sequence shown in SEQ ID NO: 18 and the CL sequence shown in SEQ ID NO: 22;

(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (iv); or (vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (iv).

In certain preferred embodiments, the substitution described in (ii) or (v) is a conservative substitution.

In certain preferred embodiments, the antibody or antigen-binding fragment thereof according to the present invention comprises:

(a) a heavy chain, which comprises an amino acid sequence selected from:

(i) a sequence comprising the VH shown in SEQ ID NO: 17 and the CH shown in SEQ ID NO: 21;

(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (i); or (iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (i);

and/or (b) a light chain, which comprises an amino acid sequence selected from:

(iv) a sequence comprising the VL sequence shown in SEQ ID NO: 19 and the CL sequence shown in SEQ ID NO: 22;

(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (iv); or (vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (iv).

In certain preferred embodiments, the substitution described in (ii) or (v) is a conservative substitution.

In certain preferred embodiments, the antibody or antigen-binding fragment thereof according to the present invention comprises:

(a) a heavy chain, which comprises an amino acid sequence selected from:

(i) a sequence comprising the VH shown in SEQ ID NO: 17 and the CH shown in SEQ ID NO: 21;

(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (i); or (iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (i);

and/or (b) a light chain, which comprises an amino acid sequence selected from:

(iv) a sequence comprising the VL sequence shown in SEQ ID NO: 18 and the CL sequence shown in SEQ ID NO: 22;

(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (iv); or (vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (iv).

In certain preferred embodiments, the substitution described in (ii) or (v) is a conservative substitution.

In certain preferred embodiments, the substitution described in (ii) or (v) is a conservative substitution.

In certain preferred embodiments, the antibody or antigen-binding fragment thereof according to the present invention comprises:

(a) a heavy chain, which comprises an amino acid sequence selected from:

(i) a sequence comprising the VH shown in SEQ ID NO: 31 and the CH shown in SEQ ID NO: 21;

(ii) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (i); or (iii) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (i);

and/or (b) a light chain, which comprises an amino acid sequence selected from:

(iv) a sequence comprising the VL sequence shown in SEQ ID NO: 32 and the CL sequence shown in SEQ ID NO: 22;

(v) a sequence having a substitution, deletion or addition of one or several amino acids or any combination thereof (e.g., a substitution, deletion or addition of 1, 2, 3, 4 or 5 amino acids, or any combination thereof) as compared with the sequence shown in (iv); or (vi) a sequence having an identity of at least 80%, at least 85%, at least 90%, at least 91%, at least 92%, at least 93%, at least 94%, at least 95%, at least 96%, at least 97%, at least 98%, at least 99%, or 100% to the sequence shown in (iv).

In certain preferred embodiments, the substitution described in (ii) or (v) is a conservative substitution.

In certain preferred embodiments, the antibody of the present invention comprises: a heavy chain comprising the VH shown in SEQ ID NO: 1 and the heavy chain constant region (CH) shown in SEQ ID NO: 21, and, a light chain comprising the VL shown in SEQ ID NO: 2 and the light chain constant region (CL) shown in SEQ ID NO: 22.

In certain preferred embodiments, the antibody of the present invention comprises: a heavy chain comprising the VH shown in SEQ ID NO: 15 and the heavy chain constant region (CH) shown in SEQ ID NO: 21, and, a light chain comprising the VL shown in SEQ ID NO: 18 and the light chain constant region (CL) shown in SEQ ID NO: 22.

In certain preferred embodiments, the antibody of the present invention comprises: a heavy chain comprising the VH shown in SEQ ID NO: 15 and the heavy chain constant region (CH) shown in SEQ ID NO: 21, and, a light chain comprising the VL shown in SEQ ID NO: 20 and the light chain constant region (CL) shown in SEQ ID NO: 22.

In certain preferred embodiments, the antibody of the present invention comprises: a heavy chain comprising the VH shown in SEQ ID NO: 16 and the heavy chain constant region (CH) shown in SEQ ID NO: 21, and, a light chain comprising the VL shown in SEQ ID NO: 18 and the light chain constant region (CL) shown in SEQ ID NO: 22.

In certain preferred embodiments, the antibody of the present invention comprises: a heavy chain comprising the VH shown in SEQ ID NO: 17 and the heavy chain constant region (CH) shown in SEQ ID NO: 21, and, a light chain comprising the VL shown in SEQ ID NO: 19 and the light chain constant region (CL) shown in SEQ ID NO: 22.

In certain preferred embodiments, the antibody of the present invention comprises: a heavy chain comprising the VH shown in SEQ ID NO: 17 and the heavy chain constant region (CH) shown in SEQ ID NO: 21, and, a light chain comprising the VL shown in SEQ ID NO: 18 and the light chain constant region (CL) shown in SEQ ID NO: 22.

In certain preferred embodiments, the antibody of the present invention comprises: a heavy chain comprising the VH shown in SEQ ID NO: 29 and the heavy chain constant region (CH) shown in SEQ ID NO: 21, and, a light chain comprising the VL shown in SEQ ID NO: 30 and the light chain constant region (CL) shown in SEQ ID NO: 22.

In certain preferred embodiments, the antibody of the present invention comprises: a heavy chain comprising the VH shown in SEQ ID NO: 31 and the heavy chain constant region (CH) shown in SEQ ID NO: 21, and, a light chain comprising the VL shown in SEQ ID NO: 32 and the light chain constant region (CL) shown in SEQ ID NO: 22.

In certain preferred embodiments, the antibody of the present invention is a chimeric antibody or humanized antibody. In certain preferred embodiments, the antibody or antigen-binding fragment thereof according to the present invention is selected from scFv, Fab, Fab', (Fab')$_2$, Fv fragment, disulfide-ligated Fv(dsFv), diabody, bispecific antibody, and multispecific antibody.

In certain embodiments, the antibody or antigen-binding fragment thereof has reduced ADCC activity.

In certain embodiments, the antibody or antigen-binding fragment thereof has reduced CDC activity.

In certain embodiments, the antibody or antigen-binding fragment thereof does not have CDC activity.

In certain embodiments, the antibody or antigen-binding fragment thereof does not have ADCC activity.

In certain preferred embodiments, the antibody or antigen-binding fragment thereof has reduced ADCC and reduced CDC activity.

In certain preferred embodiments, the antibody or antigen-binding fragment thereof does not have ADCC nor CDC activity.

In certain preferred embodiments, the antibody or antigen-binding fragment thereof according to the present invention has at least one of the following characteristics:

(a) binding FXI and/or FXIa (e.g., human FXI and/or human FXIa) with a $K_D$ of less than about 100 nM, for example, less than about 10 nM, 1 nM, 0.1 nM or less; preferably, the $K_D$ may be measured by a technique known in the art, for example, measured by biofilm interference technology (BLI) (e.g., ForteBio Octet®);

(b) binding FXI and/or FXIa (e.g., human FXI and/or human FXIa) with an $EC_{50}$ of less than about 500 nM, for example, less than about 100 nM, 10 nM, 1 nM, 0.9 nM, 0.8 nM, 0.7 nM, 0.6 nM, 0.5 nM, 0.4 nM, 0.3 nM, 0.2 nM, 0.1 nM or less; preferably, the $EC_{50}$ can be measured by a technique known in the art, for example, measured by flow cytometry or cell competitive ELISA technique;

(c) the binding of the antibody or antigen-binding fragment thereof to FXI and/or FXIa inhibits or blocks the binding of FXI and/or FXIa to a substrate, thereby prolonging clotting time;

(d) the binding of the antibody or antigen-binding fragment thereof to FXI and/or FXIa inhibits or blocks the catalytic effect of FXI and/or FXIa on a substrate;

(e) the binding of the antibody or antigen-binding fragment thereof to FXI and/or FXIa does not affect exogenous coagulation;

(f) the antibody or antigen-binding fragment thereof has reduced ADCC and/or CDC activity;

(g) the antibody or antigen-binding fragment thereof does not have ADCC and/or CDC activity;

(h) the binding of the antibody or antigen-binding fragment thereof to FXI and/or FXIa inhibits or blocks the formation of the dimers of FXI and/or the dimers of FXIa;

(i) the binding of the antibody or antigen-binding fragment thereof to FXI and/or FXIa inhibits or blocks the formation of a complex between FXI and/or FXIa and HK;

(j) binding to the catalytic domain of FXI and/or FXIa, and/or inducing a conformational change thereof;

(k) inhibiting or blocking the binding of FXI and/or FXIa to a platelet receptor; or (l) any combination of (a) to (k).

In certain preferred embodiments, the antibody or antigen-binding fragment thereof according to the present invention, when bound to FXI, prevents the FXI catalytic domain from presenting an active conformation. In certain preferred embodiments, the antibody or antigen-binding fragment thereof according to the present invention, when bound to FXI, prevents the FXI catalytic domain from presenting an active conformation by inducing a conformational change in the zymogen structure, thereby further inhibiting the binding to FIX.

Derived Antibodies

The antibody or antigen-binding fragment thereof according to the present invention can be derivatized, for example linked to another molecule (for example another polypeptide or protein). Generally, the derivatization (e.g., labeling) of the antibody or antigen-binding fragment thereof will not adversely affect its binding to FXI and/or FXIa (especially human FXI and/or FXIa). Therefore, the antibody or antigen-binding fragment thereof according to the present invention are also intended to include such derivatized forms. For example, the antibody or antigen-binding fragment thereof according to the present invention can be functionally linked (by chemical coupling, gene fusion, non-covalent linkage or other means) to one or more other molecular groups, such as another antibody (e.g., to form a bispecific antibody), detection reagent, pharmaceutical reagent, and/or protein or polypeptide (e.g., avidin or polyhistidine tag) capable of mediating the binding of the antibody or antigen-binding fragment thereof to another molecule.

One type of derivatized antibody (e.g., bispecific antibody) is produced by cross-linking two or more antibodies (of the same type or different types). Methods for obtaining such bispecific antibodies are well-known in the art, and examples thereof include, but are not limited to, chemical cross-linking methods, cell engineering methods (hybrid hybridoma methods), or genetic engineering methods.

Another type of derivatized antibody is a labeled antibody. For example, the antibody or antigen-binding fragment thereof according to the present invention can be linked to a detectable label. The detectable label of the present invention can be any substance that can be detected by fluorescence, spectroscopy, photochemistry, biochemistry, immunology, electrical, optical or chemical means. Such labels are well known in the art, examples thereof include, but are not limited to, enzyme (e.g., horseradish peroxidase, alkaline phosphatase, β-galactosidase, urease, glucose oxidase, etc.), radioactive nuclear (e.g., $^3$H, $^{125}$I, $^{35}$S, $^{14}$C or $^{32}$P), fluorescent dye (e.g., fluorescein isothiocyanate (FITC), fluorescein, tetramethylrhodamine isothiocyanate (TRITC), phycoerythrin (PE), Texas Red, Rhodamine, quantum dots or cyanine dye derivatives (e.g., Cy7, Alexa 750), acridine ester compounds, magnetic beads (e.g., Dynabeads®), calorimetric label such as colloidal gold or colored glass or plastic (e.g., polystyrene, polypropylene, latex, etc.) beads, and biotin for binding an avidin (e.g., streptavidin) modified by the above-mentioned labels. The patents teaching the usage of these labels include, but are not limited to, U.S. Pat. Nos. 3,817,837; 3,850,752; 3,939,350; 3,996,345; 4,277,437; 4,275,149; and 4,366,241 (all incorporated herein by reference). The detectable labels as described above can be detected by methods known in the art. For example, the radioactive label can be detected using photographic film or a scintillation calculator, and the fluorescent label can be detected using a photodetector to detect the emitted light. The enzyme label is generally detected by providing a substrate to the enzyme and detecting a reaction product produced by the action of the enzyme on the substrate, and the calorimetric label is detected by simple visualization of the colored label. In some embodiments, such a label can be suitable for immunological detection (e.g., enzyme-linked immunoassay, radioimmunoassay, fluorescence immunoassay, chemiluminescence immunoassay, etc.). In some embodiments, the detectable label as described above can be linked to the antibody or antigen-binding fragment thereof according to the present invention through a linker of different lengths so as to reduce potential steric hindrance.

In addition, the antibody or antigen-binding fragment thereof according to the present invention can also be derivatized with a chemical group, such as polyethylene glycol (PEG), methyl or ethyl, or a sugar group. These groups can be used to improve the biological properties of the antibody, such as increasing its serum half-life.

As one of the antibody derivatives, the present invention provides a conjugate. In some embodiments, the conjugate comprises any antibody or antigen-binding fragment thereof that specifically binds to FXI and/or FXIa according to the present invention, and a conjugate moiety, and the conjugate moiety is a detectable label, such as the above-mentioned radioisotope, fluorescent substance, luminescent substance, colored substance or enzyme. In certain embodiments, the conjugate moiety is a therapeutic agent; optionally, the therapeutic agent binds to one or more of the antibody or antigen-binding fragment thereof according to the present invention through a linker. Optionally, the therapeutic agent is bound to the antibody or antigen-binding fragment thereof according to the present invention through a linker. The therapeutic agent is selected from any one of the drugs mentioned in the uses, treatment methods, and pharmaceutical compositions in the present disclosure. The linker does not significantly affect the biological activity of the antibody or antigen-binding fragment thereof according to the present invention.

As one of the antibody derivatives, the present invention provides a multispecific antibody comprising the antibody or antigen-binding fragment thereof that specifically binds FXI and/or FXIa according to the present invention, and another antibody or antigen-binding fragment, or antibody mimetics. In some embodiments, the multispecific antibody is a conjugate comprising the antibody or antigen-binding fragment thereof that specifically binds to FXI and/or FXIa according to the present invention and another antibody or antigen-binding fragment thereof, or antibody mimetics.

In certain embodiments, the multispecific antibody is formed by coupling the antibody or antigen-binding fragment thereof that specifically binds to FXI and/or FXIa according to the present invention with another antibody or antigen-binding fragment thereof or antibody mimetics, and wherein, each antibody or antigen-binding fragment thereof or antibody mimetics maintains the original binding specificity. In certain preferred embodiments, the multispecific antibody is a bispecific antibody or a trispecific antibody or a tetraspecific antibody.

Preparation of Antibodies

The antibody of the present invention can be prepared by various methods known in the art, for example, obtained by genetic engineering recombination technology. For example, DNA molecules encoding the heavy chain and light chain genes of the antibody of the present invention are obtained by chemical synthesis or PCR amplification. The resulting DNA molecules are inserted into an expression vector and then transfected into a host cell. Then, the transfected host cell is cultured under specific conditions, and the antibody of the present invention is expressed.

The antigen-binding fragment of the present invention can be obtained by hydrolyzing an intact antibody molecule (see: Morimoto et al., J. Biochem. Biophys. Methods 24: 107-117 (1992) and Brennan et al., Science 229: 81 (1985)). In addition, these antigen-binding fragments can also be directly produced by recombinant host cells (reviewed in Hudson, Curr. Opin. Immunol. 11: 548-557 (1999); Little et al., Immunol. Today, 21: 364-370 (2000)). For example, Fab' fragments can be obtained directly from host cells; Fab' fragments can be chemically coupled to form F(ab')$_2$ fragments (Carter et al., Bio/Technology, 10: 163-167 (1992)). In addition, Fv, Fab or F(ab')$_2$ fragments can also be directly isolated from the culture medium of recombinant host cells. Those of ordinary skill in the art are fully aware of other techniques for preparing these antigen-binding fragments.

Therefore, in another aspect, the present invention provides an isolated nucleic acid molecule, comprising a nucleotide sequence encoding the antibody or antigen-binding fragment thereof, or its heavy chain variable region and/or light chain variable region, or one or more CDRs thereof according to the present invention. According to the codon degeneracy known in the art, in some embodiments, the nucleotide sequence can be replaced based on the codon degeneracy. In certain embodiments, the nucleotide sequence is codon optimized.

In certain preferred embodiments, the isolated nucleic acid molecule comprises: a first nucleic acid and a second nucleic acid encoding the heavy chain variable region and the light chain variable region of the antibody or antigen-binding fragment thereof according to the present invention respectively, or a first nucleic acid encoding the heavy chain variable region and the heavy chain constant region of the antibody or antigen-binding fragment thereof according to the present invention, and a second nucleic acid encoding the light chain variable region and the light chain constant region, or a first nucleic acid and a second nucleic acid encoding the heavy chain and the light chain of the antibody or antigen-binding fragment thereof according to the present invention respectively. In certain preferred embodiments, the antibody of the present invention described above is selected from any one of the following groups: 36G9.10, 36G9.10-hz43, 36G9.10-hz73, 36G9.10-hz74, 36G9.10-hz92, 36G9.10-hz93, 7B2, 7B2-hz11. In certain preferred embodiments, the first nucleic acid and the second nucleic acid comprise nucleic acids having substantially the same sequence as the first nucleic acid and the second nucleic acid described above. For example, the isolated nucleic acid molecule may comprise the nucleotide sequence shown in SEQ ID NO: 23, SEQ ID NO: 24, SEQ ID NO: 27, SEQ ID NO: 28 in the sequence listing or a sequence substantially identical thereto. For example, the sequence substantially identical thereto refers to a sequence having an identity of at least about 85%, 90%, 95%, 99% or higher to the sequence to which it compared, or a sequence having a substitution of one or more nucleotides, or a sequence that does not differ by more than 3, 6, 15, 30 or 45 nucleotides.

In certain preferred embodiments, the present invention provides an isolated nucleic acid molecule comprising a nucleic acid molecule encoding an antibody heavy chain variable region, and/or a nucleic acid molecule encoding an antibody light chain variable region, wherein, the nucleic acid molecule encoding the antibody heavy chain variable region has a nucleotide sequence selected from the group consisting of: (a) the nucleotide sequence shown in SEQ ID NO: 23, or (b) a sequence that is substantially the same as the nucleotide sequence described in (a) (e.g., a sequence having an identity of at least about 85%, 90%, 95%, 99% or more compared with the nucleotide sequence described in (a), or a sequence having a substitution of one or more nucleotides), or (c) a sequence that does not differ from the nucleotide sequence described in (a) by more than 3, 6, 15, 30 or 45 nucleotides; the nucleic acid molecule encoding the antibody light chain variable region has a sequence selected from the group consisting of: (d) the nucleotide sequence shown in SEQ ID NO: 24, or (e) a sequence that is substantially the same as the nucleotide sequence described in (d) (e.g., a sequence having an identity of at least about 85%, 90%, 95%, 99% or more compared with the nucleotide sequence described in (d), or a sequence having a substitution of one or more nucleotides), or (f) a sequence that does not differ from the nucleotide sequence described in (d) by more than 3, 6, 15, 30 or 45 nucleotides.

In certain preferred embodiments, the present invention provides an isolated nucleic acid molecule comprising a nucleic acid molecule encoding an antibody heavy chain variable region, and/or a nucleic acid molecule encoding an antibody light chain variable region, wherein, the nucleic acid molecule encoding the antibody heavy chain variable region has a nucleotide sequence selected from the group consisting of: (a) the nucleotide sequence shown in SEQ ID NO: 27, or (b) a sequence that is substantially the same as the nucleotide sequence described in (a) (e.g., a sequence having an identity of at least about 85%, 90%, 95%, 99% or more compared with the nucleotide sequence described in (a), or a sequence having a substitution of one or more nucleotides), or (c) a sequence that does not differ from the nucleotide sequence described in (a) by more than 3, 6, 15, 30 or 45 nucleotides; the nucleic acid molecule encoding the antibody light chain variable region has a sequence selected from the group consisting of: (d) the nucleotide sequence shown in SEQ ID NO: 28, or (e) a sequence that is substantially the same as the nucleotide sequence described in (d) (e.g., a sequence having an identity of at least about 85%, 90%, 95%, 99% or more compared with the nucleotide sequence described in (d), or a sequence having a substitution of one or more nucleotides), or (f) a sequence that does not differ from the nucleotide sequence described in (d) by more than 3, 6, 15, 30 or 45 nucleotides.

In certain preferred embodiments, the isolated nucleic acid molecule of the present invention comprises the nucleic acid molecule as shown in SEQ ID NO: 23 that encodes the antibody heavy chain variable region, and/or the nucleic acid molecule as shown in SEQ ID NO: 24 that encodes the antibody light chain variable region.

In certain preferred embodiments, the isolated nucleic acid molecule of the present invention comprises the nucleic acid molecule as shown in SEQ ID NO: 27 that encodes the antibody heavy chain variable region, and/or the nucleic acid molecule as shown in SEQ ID NO: 28 that encodes the antibody light chain variable region.

In certain preferred embodiments, the present invention provides an isolated nucleic acid molecule comprising a nucleic acid molecule encoding an antibody heavy chain, and/or a nucleic acid molecule encoding an antibody light chain, wherein, the nucleic acid molecule encoding the antibody heavy chain has a nucleotide sequence selected from the group consisting of: (a) the nucleotide sequence shown in SEQ ID NO: 25, or (b) a sequence that is substantially the same as the nucleotide sequence described in (a) (e.g., a sequence having an identity of at least about 85%, 90%, 95%, 99% or more compared with the nucleotide sequence described in (a), or a sequence having a substitution of one or more nucleotides), or (c) a sequence that does not differ from the nucleotide sequence described in (a) by more than 3, 6, 15, 30 or 45 nucleotides; and/or, the nucleic acid molecule encoding the antibody light chain has a sequence selected from the group consisting of: (d) the nucleotide sequence shown in SEQ ID NO: 26, or (e) a sequence that is substantially the same as the nucleotide sequence described in (d) (e.g., a sequence having an identity of at least about 85%, 90%, 95%, 99% or more compared with the nucleotide sequence described in (d), or a sequence having a substitution of one or more nucleotides), or (f) a sequence that does not differ from the nucleotide sequence described in (d) by more than 3, 6, 15, 30 or 45 nucleotides.

In certain preferred embodiments, the isolated nucleic acid molecule of the present invention comprises the nucleic acid molecule as shown in SEQ ID NO: 25 that encodes the antibody heavy chain, and/or the nucleic acid molecule as shown in SEQ ID NO: 26 that encodes the antibody light chain.

Another aspect of the present invention provides a vector (e.g., a cloning vector or an expression vector), which comprises the isolated nucleic acid molecule of the present invention. In certain preferred embodiments, the vector of the present invention is, for example, a plasmid, cosmid, bacteriophage, lentivirus and the like. In certain preferred embodiments, the vector is capable of expressing the antibody or antigen-binding fragment thereof according to the present invention in a subject (e.g., a mammal, such as a human).

Another aspect of the present invention provides a host cell, which comprises the isolated nucleic acid molecule of the present invention or the vector of the present invention. The host cell may be an eukaryotic cell (e.g., a mammalian cell, an insect cell, a yeast cell) or a prokaryotic cell (e.g., *Escherichia coli*). Suitable eukaryotic cells include, but are not limited to, NSO cell, Vero cell, Hela cell, COS cell, CHO cell, HEK293 cell, BHK cell, and MDCKII cell. Suitable insect cells include, but are not limited to, Sf9 cell. In certain preferred embodiments, the host cell of the present invention is a mammalian cell, such as CHO (e.g., CHO-K1, CHO-S, CHO DXB11, CHO DG44).

Another aspect of the present invention provides a method for preparing the antibody or antigen-binding fragment thereof according to the present invention, which comprises culturing the host cell of the present invention under conditions that allow the expression of the antibody or antigen-binding fragment thereof, and recovering the antibody or antigen-binding fragment thereof from the culture of the cultured host cell.

Uses, Treatment Methods and Pharmaceutical Compositions

Another aspect of the present invention provides a pharmaceutical composition, which comprises the antibody or antigen-binding fragment thereof, isolated nucleic acid molecule, vector, host cell, multispecific antibody or conjugate according to the present invention, and a pharmaceutically acceptable carrier and/or excipient.

In certain preferred embodiments, the pharmaceutical composition of the present invention comprises the antibody or antigen-binding fragment thereof according to the present invention, and a pharmaceutically acceptable carrier and/or excipient.

In certain preferred embodiments, the pharmaceutical composition of the present invention comprises the isolated nucleic acid molecule, vector or host cell according to the present invention, and a pharmaceutically acceptable carrier and/or excipient. In such embodiments, the host cell comprises the isolated nucleic acid molecule or vector as previously described.

In certain preferred embodiments, the pharmaceutical composition may further comprises an additional pharmaceutically active agent. In certain preferred embodiments, the additional pharmaceutically active agent is an antiplatelet drug, an anticoagulant drug or a thrombolytic drug.

In certain preferred embodiments, in the pharmaceutical composition, the antibody or antigen-binding fragment thereof according to the present invention and the additional pharmaceutically active agent are provided as separate components or as components of a single composition. Therefore, the antibody or antigen-binding fragment thereof according to the present invention and the additional pharmaceutically active agent can be administered simultaneously, separately or sequentially.

In certain preferred embodiments, the pharmaceutical composition may further comprise an additional pharmaceutically active agent. The additional pharmaceutically active agent is selected from the group consisting of aspirin, clopidogrel, prasugrel, ticagrelor, abciximab, eptifibatide, vorapaxar, unfractionated heparin, heparin, low molecular weight heparin, warfarin, fondaparinux, edoxaban, betrixaban, rivaroxaban, apixaban, dabigatran etexilate, argatroban, bivalirudin, streptokinase, urokinase, alteplase, prourokinase, or any combination thereof.

In another aspect, the antibody or antigen-binding fragment thereof, isolated nucleic acid molecule, vector, host cell, multispecific antibody or conjugate in the pharmaceutical composition of the present invention is sufficient to produce in a subject at least one of the following biological activities:

(a) binding to the catalytic domain of FXI and/or FXIa, and/or inducing its conformational change;
(b) inhibiting or blocking the binding of FXI and/or FXIa to a substrate;
(c) inhibiting or blocking the binding of FXI and/or FXIa to a platelet receptor;
(d) inhibiting or blocking the binding of FXI to coagulation factor XIIa (FXIIa), thereby inhibiting or blocking the conversion of FXI into active FXIa;
(e) inhibiting or blocking the binding of FXIa to coagulation factor FIX, thereby inhibiting or blocking the conversion of FIX into active FIXa;
(f) inhibiting or blocking the activation of FXI and/or FXIa-mediated endogenous coagulation pathway;
(g) inhibiting or blocking the activity of FXI and/or FXIa in thrombosis;
(h) prolonging FXI and/or FXIa-mediated clotting time;
(i) inhibiting thrombosis;
(j) preventing and/or treating a disease or disorder associated with coagulation or thromboembolism mediated by FXI and/or FXIa; or
(k) any combination of (a) to (j).

In another aspect, the pharmaceutical composition of the present invention further comprises a second antibody or a nucleic acid encoding the second antibody, wherein the second antibody is another antibody that recognizes a different epitope of FXI or FXIa, or is an antibody specifically binding to a receptor or ligand selected from the group consisting of: thrombin, antiplasmin, Factor XII, Factor VIII, Factor VII, Factor X, Factor IX, Factor II, tissue Factor, P-selectin and ligand thereof, L-selectin and ligand thereof, and any combination of the above antibodies.

Another aspect of the present invention provides a use of the antibody or antigen-binding fragment thereof, isolated nucleic acid molecule, vector, host cell, multispecific antibody, conjugate or pharmaceutical composition of the present invention in manufacture of a medicament, and the medicament is used for:

(a) binding to the catalytic domain of FXI and/or FXIa, and/or inducing its conformational change;
(b) inhibiting or blocking the binding of FXI and/or FXIa to a substrate;
(c) inhibiting or blocking the binding of FXI and/or FXIa to a platelet receptor;
(d) inhibit or blocking the binding of FXI to coagulation factor XIIa (FXIIa), thereby inhibiting the conversion of FXI into active FXIa;
(e) inhibiting or blocking the binding of FXIa to coagulation factor FIX, thereby inhibiting the conversion of FIX into active FIXa;
(f) inhibiting or blocking the activation of FXI and/or FXIa-mediated endogenous coagulation pathway;
(g) inhibiting or blocking the activity of FXI and/or FXIa in thrombosis;
(h) prolonging FXI and/or FXIa-mediated clotting time;
(i) inhibiting thrombosis;
(j) preventing and/or treating a disease or disorder associated with coagulation or thromboembolism mediated by FXI and/or FXIa; or
(k) any combination of (a) to (j).

In certain preferred embodiments, when the isolated nucleic acid molecule, vector or host cell of the present invention is used for manufacture of a medicament, the host cell comprises the isolated nucleic acid molecule or vector as described above.

In certain preferred embodiments, when the vector or host cell of the present invention is used for manufacture of a medicament, the medicament is used for prevention and/or treatment of a disease or disorder associated with coagulation or thromboembolism in a subject (e.g., a human).

In certain embodiments, the subject is a mammal. In certain preferred embodiments, the subject is a human.

In certain preferred embodiments, when the vector or host cell of the present invention is used for manufacture of a medicament, the medicament is used for delaying the occurrence of a disease or disorder associated with coagulation or thromboembolism in a subject (e.g., a human).

In certain preferred embodiments, when the vector or host cell of the present invention is used for manufacture of a medicament, the medicament is used for reducing or inhibiting the recurrence of a disease or disorder associated with coagulation or thromboembolism in a subject (e.g., a human).

In certain preferred embodiments, when the vector or host cell of the present invention is used for manufacture of a medicament, the medicament is used in a subject (e.g., a human).

In certain preferred embodiments, the antibody or antigen-binding fragment thereof, isolated nucleic acid molecule, vector, host cell, multispecific antibody, conjugate, or pharmaceutical composition of the present invention involves in a disease or disorder associated with coagulation or thromboembolism that is selected from the group consisting of: thrombosis, thrombotic stroke, atrial fibrillation, stroke prevention associated with atrial fibrillation (SPAF), deep vein thrombosis, venous thromboembolism, acute coronary syndrome (ACS), ischemic stroke, acute limb ischemia, chronic thromboembolism pulmonary hypertension, systemic embolism, myocardial infarction (MI), acute myocardial infarction (AMI), stable angina pectoris, unstable angina pectoris, reocclusion and restenosis after coronary intervention, peripheral arterial occlusive disease (PAOD), renal vein thrombosis, transient ischemic attack (TIA), pulmonary thromboembolism, diffuse intravascular coagulation, thromboembolic disorder caused by medical device (e.g., catheter), severe systemic inflammatory response syndrome, metastatic cancer, infectious disease, organ failure (e.g., renal failure), toxicity caused by the administration of therapeutic protein in the body, multiple trauma, ischemia-reperfusion injury, local fibrin deposition, adult alveolar proteinosis, thromboembolic event (VTE) before and after joint replacement (TKA) surgery, coronary heart disease, thromboembolism after myocardial infarction, stroke in patient with non-valvular atrial fibrillation, thrombosis and thromboembolism in chronic kidney disease, thrombosis and thromboembolism in patients undergoing hemodialysis and patients undergoing extracorporeal membrane oxygenation, deep vein thrombosis (DVT), or pulmonary embolism (PE).

In another aspect, the present invention provides a method of preventing and/or treating a disease or disorder associated with coagulation or thromboembolism in a subject. In another aspect, the present invention provides a method for delaying the occurrence of a disease or disorder associated with coagulation or thromboembolism in a subject. In another aspect, the present invention provides a method for reducing or inhibiting the recurrence of a disease or disorder associated with coagulation or thromboembolism in a subject. The methods described above comprise administering an effective amount of the antibody or antigen-binding fragment thereof, vector, host cell, multispecific antibody, conjugate, or pharmaceutical composition of the present invention to a subject in need thereof.

When the host cell of the present invention is used in the methods described above, the host cell comprises the isolated nucleic acid molecule or vector as described above.

In another aspect, the above methods further comprise administering a second therapy to the subject, wherein the second therapy is selected from the group consisting of antiplatelet drug, anticoagulant drug, and thrombolytic drug.

In certain preferred embodiments, the second therapy is selected from aspirin, clopidogrel, prasugrel, ticagrelor, abciximab, eptifibatide, vorapaxar, unfractionated heparin, heparin, low molecular weight heparin, warfarin, fondaparinux, edoxaban, betrixaban, rivaroxaban, apixaban, dabigatran etexilate, argatroban, bivalirudin, streptokinase, urokinase, alteplase, prourokinase, and any combination thereof.

In certain preferred embodiments, the antibody or antigen-binding fragment thereof, isolated nucleic acid molecule, vector, host cell, multispecific antibody, conjugate, or pharmaceutical composition of the present invention involves in a disease or disorder associated with coagulation or thromboembolism that is selected from the group consisting of: thrombosis, thrombotic stroke, atrial fibrillation, stroke prevention associated with atrial fibrillation (SPAF), deep vein thrombosis, venous thromboembolism, acute coronary syndrome (ACS), ischemic stroke, acute limb ischemia, chronic thromboembolism pulmonary hypertension, systemic embolism, myocardial infarction (MI), acute myocardial infarction (AMI), stable angina pectoris, unstable angina pectoris, reocclusion and restenosis after coronary intervention, peripheral arterial occlusive disease (PAOD), renal vein thrombosis, transient ischemic attack (TIA), pulmonary thromboembolism, diffuse intravascular coagulation, thromboembolic disorder caused by medical device (e.g., catheter), severe systemic inflammatory response syndrome, metastatic cancer, infectious disease, organ failure (e.g., renal failure), toxicity caused by the administration of therapeutic protein in the body, multiple trauma, ischemia-reperfusion injury, local fibrin deposition, adult alveolar proteinosis, thromboembolic event (VTE) before and after joint replacement (TKA) surgery, coronary heart disease, thromboembolism after myocardial infarction, stroke in patients with non-valvular atrial fibrillation, thrombosis and thromboembolism in chronic kidney disease, thrombosis and thromboembolism in patients undergoing hemodialysis and patients undergoing extracorporeal membrane oxygenation, deep vein thrombosis (DVT) or pulmonary embolism (PE).

The antibody or antigen-binding fragment thereof according to the present invention, and the pharmaceutical composition of the present invention can be formulated into any dosage form known in the medical field, for example, tablets, pills, suspensions, emulsions, solutions, gels, capsules, powders, granules, elixirs, lozenges, suppositories, injections (including solutions for injection, sterile powders for injection and concentrated solutions for injection), inhalants, sprays, etc. The preferred dosage form depends on the intended mode of administration and therapeutic use. The pharmaceutical composition of the present invention should be sterile and stable under the conditions of production and storage. A preferred dosage form is injection. Such injection may be a sterile injection solution. For example, a sterile injection solution can be prepared by the following method: incorporating a necessary dose of the recombinant protein of the present invention in an appropriate solvent, and optionally, simultaneously incorporating other desired ingredients (including but not limited to, pH adjustment agent, surfactant, adjuvant, ionic strength enhancer, isotonic agent, preservative, diluent, or any combination thereof), followed by filtration and sterilization. In addition, the sterile injection solution can be prepared as a sterile lyophilized powder (e.g., by vacuum drying or freeze drying) for storage and use. Such sterile lyophilized powder can be dispersed in a suitable carrier, such as sterile pyrogen-free water, before use.

In addition, the antibody or antigen-binding fragment thereof according to the present invention may be present in a pharmaceutical composition in a unit dosage form for ease administration.

The antibody or antigen-binding fragment thereof, and the pharmaceutical composition of the present invention can be administered by any suitable method known in the art, including but not limited to oral, buccal, sublingual, ocular, topical, parenteral, rectal, intrathecal, intra-cisterna, in the groin, intravesical, local (such as powder, ointment or drops), or nasal route. However, for many therapeutic applications, the preferred route/mode of administration is parenteral administration (e.g., intravenous injection, subcutaneous injection, intraperitoneal injection, intramuscular injection). The skilled person should understand that the route and/or mode of administration will vary according to the intended purpose. In a preferred embodiment, the antibody or antigen-binding fragment thereof, or the pharmaceutical composition of the present invention is administered by intravenous infusion or injection.

The pharmaceutical composition of the present invention may comprise a "therapeutically effective amount" or "prophylactically effective amount" of the antibody or antigen-binding fragment thereof, isolated nucleic acid molecule, vector, host cell, multispecific antibody or conjugate of the present invention. "Prophylactically effective amount" refers to an amount sufficient to prevent, stop, or delay the occurrence of a disease. "Therapeutically effective amount" refers to an amount sufficient to cure or at least partially stop the disease and complication thereof in a patient who has already suffered from the disease. The therapeutically effective amount of the antibody or antigen-binding fragment thereof according to the present invention may vary according to the following factors: the severity of the disease to be treated, the overall state of the patient's own immune system, the patient's general conditions such as age, weight and gender, administration mode of medicine, other therapies administered at the same time, and so on.

In the present invention, the dosage regimen can be adjusted to obtain the best desired response (e.g., therapeutic or preventive response). For example, it can be administered in a single dose, can be administered multiple times over a period of time, or the dose can be reduced or increased proportionally according to the urgency of the treatment situation.

The typical non-limiting range of the therapeutically or prophylactically effective amount of the recombinant protein of the present invention is 0.02 to 100 mg/kg, such as 0.1 to 100 mg/kg, 0.1 to 50 mg/kg, or 1 to 50 mg/kg. It should be noted that the dosage may vary depending on the type and severity of the symptoms to be treated. In addition, those skilled in the art understand that for any particular patient, the specific dosage regimen should be adjusted over time according to the needs of the patient and the professional evaluation of the doctor; the dosage range given here is for illustrative purposes only, and does not limit the use or scope of the pharmaceutical composition of the present invention.

In the present invention, the subject may be a mammal, such as a human.

Detection Method and Kit

The antibody or antigen-binding fragment thereof according to the present invention can specifically bind to FXI and/or FXIa (e.g., human FXI and/or human FXIa), and thus can be used to detect the presence or level of FXI and/or FXIa in a sample.

Therefore, in another aspect, the present invention provides a kit, which comprises the antibody or antigen-binding fragment thereof according to the present invention. In certain preferred embodiments, the antibody or antigen-binding fragment thereof according to the present invention bears a detectable label. In a preferred embodiment, the kit further comprises a second antibody, which specifically recognizes the antibody or antigen-binding fragment thereof according to the present invention. Preferably, the second antibody further comprises a detectable label.

In the present invention, the detectable label may be any substance that can be detected by fluorescence, spectroscopy, photochemical, biochemical, immunological, electrical, optical or chemical means. It is particularly preferred that such a label can be applied to immunological detection (e.g., enzyme-linked immunoassay, radioimmunoassay, fluorescence immunoassay, chemiluminescence immunoassay, etc.). Such labels are well known in the art and include but not limited to enzyme (e.g., horseradish peroxidase, alkaline phosphatase, β-galactosidase, urease, glucose oxidase, etc.), radionuclide (e.g., $^3$H, $^{125}$I, $^{35}$S, $^{14}$C or $^{32}$P), fluorescent dye (e.g., fluorescein isothiocyanate (FITC), fluorescein, tetramethylrhodamine isothiocyanate (TRITC), phycoerythrin (PE), Texas red, rhodamine, quantum dots or cyanine dye derivatives (e.g. Cy7, Alexa 750)), acridine ester compounds, magnetic beads (e.g. Dynabeads®), calorimetric label such as colloidal gold or colored glass or plastic (e.g., polystyrene, polypropylene, latex, etc.) beads, and biotin for binding an avidin (e.g., streptavidin) modified by the above-mentioned labels. The patents teaching the usage of these labels include, but are not limited to, U.S. Pat. Nos. 3,817,837; 3,850,752; 3,939,350; 3,996,345; 4,277,437; 4,275,149; and 4,366,241 (all incorporated herein by reference). The detectable labels as described above can be detected by methods known in the art. For example, the radioactive label can be detected using photographic film or a scintillation calculator, and the fluorescent label can be detected using a photodetector to detect the emitted light. The enzyme label is generally detected by providing a substrate to the enzyme and detecting a reaction product produced by the action of the enzyme on the substrate, and the calorimetric label is detected by simple visualization of the colored label. In some embodiments, the detectable label as described above can be linked to the antibody or antigen-binding fragment thereof according to the present invention through a linker of different lengths so as to reduce potential steric hindrance.

In another aspect, the present invention provides a method for detecting the presence or level of FXI and/or FXIa (e.g., human FXI and/or human FXIa) in a sample, which comprises a step of using the antibody or antigen-binding fragment thereof according to the present invention. In a preferred embodiment, the antibody or antigen-binding fragment thereof according to the present invention also bears a detectable label. In another preferred embodiment, the method further comprises using a reagent bearing a detectable label to detect the antibody or antigen-binding fragment thereof according to the present invention. The method can be used for diagnostic purpose, or for non-diagnostic purpose (e.g., the sample is a cell sample, not a sample from a patient).

In another aspect, the present invention provides a method for detecting the presence or level of FXI and/or FXIa (e.g., human FXI and/or human FXIa) in a sample, the method comprising contacting the antibody or antigen-binding fragment thereof according to the present invention with the sample under a condition allowing the formation of a complex between the antibody or antigen-binding fragment thereof or conjugate and FXI and/or FXIa, and detecting the formation of the complex.

In another aspect, there is provided a use of the antibody or antigen-binding fragment thereof according to the present invention in manufacture of a kit for detecting the presence or level of FXI and/or FXIa (e.g., human FXI and/or human FXIa) in a sample. In another aspect, the present invention provides a diagnostic or therapeutic kit, which comprises one or more of the following substances that the present invention can provide: the antibody or antigen-binding fragment thereof, isolated nucleic acid molecule, vector, host cell, multispecific antibody, conjugate, or pharmaceutical composition. The diagnostic or therapeutic kit also comprises an instruction for use.

The antibody or antigen-binding fragment of the present invention has high binding affinity to FXI and/or FXIa, and has extremely strong specificity. Therefore, the antibody or antigen-binding fragment of the present invention is suitable for prevention and/or treatment of a disease or disorder associated with coagulation or thromboembolism. The humanized antibody of the present invention retains the functions and properties of the parental murine antibody. Moreover, the humanized antibody of the present invention has a high degree of humanization, so that it can be safely administered to a human subject without triggering an immunogenic response. In addition, the antibody or antigen-binding fragment of the present invention has no or very little risk of bleeding. Therefore, the antibody or antigen-binding fragment of the present invention has great clinical value.

Definition of Acronyms and Terms
  CDR complementarity determining region in immunoglobulin variable region antibody framework region: amino acid residues other than CDR residues in antibody variable region
  VH antibody heavy chain variable region
  VL antibody light chain variable region
  IgG immunoglobulin G
  Kabat the immunoglobulin alignment and numbering system proposed by Elvin A. Kabat (see, for example, Kabat et al., Sequences of Proteins of Immunological Interest, 5th Ed. Public Health Service, National Institutes of Health, Bethesda, Md., 1991).
  Chothia the immunoglobulin numbering system proposed by Chothia et al., which is a classic rule for identifying the boundaries of CDR regions based on the location of the structural loop region (see, for example, Chothia & Lesk (1987) J. Mol. Biol. 196: 901-917; Chothia (1989) Nature 342: 878-883).
  AbM The definition of AbM CDR comes from Martin's related research (Martin A C R, Cheetham J C, Rees A R (1989) Modelling antibody hypervariable loops: A combined algorithm. Proc Natl Acad Sci USA 86:9268-9272), this definition method integrates the partial definitions of Kabat and Chothia
  IMGT A numbering system based on the international ImMunoGeneTics information system® (IMGT) initiated by Lefranc et al., See, Lefranc et al., Dev. Comparat. Immunol. 27:55-77, 2003
  mAb monoclonal antibody
  EC50 concentration at which 50% efficacy or binding is produced
  IC50 concentration at which 50% inhibition is produced
  ELISA enzyme-linked immunosorbent assay
  PCR polymerase chain reaction
  HRP horseradish peroxidase
  KD equilibrium dissociation constant
  Ka association rate constant
  Kd dissociation rate constant
  ADCC antibody-dependent cytotoxicity
  CDC complement-dependent cytotoxicity
  FACS fluorescence-activated cell sorting
  CDR-H1 complementarity determining region 1 in immunoglobulin heavy chain variable region
  CDR-H2 complementarity determining region 2 in immunoglobulin heavy chain variable region
  CDR-H3 complementarity determining region 3 in immunoglobulin heavy chain variable region
  CDR-L1 complementarity determining region 1 in immunoglobulin light chain variable region
  CDR-L2 complementarity determining region 2 in immunoglobulin light chain variable region
  CDR-L3 complementarity determining region 3 in immunoglobulin light chain variable region
  APTT activated partial thromboplastin time
  CFA complete Freund's adjuvant
  EC50 half maximum effect concentration
  FACS flow cytometry technology
  IC50 half maximum inhibitory concentration
  IFA incomplete Freund's adjuvant
  MFI mean fluorescence intensity
  FXI human coagulation Factor XI
  FXIa activated human coagulation Factor XI
  RLU relative light unit In the present invention, unless otherwise specified, the scientific and technical terms used herein have the meanings commonly understood by those skilled in the art. In addition, the laboratory procedures of cell culture, biochemistry, nucleic acid chemistry, immunology, etc. used herein are all routine procedures widely used in the corresponding fields. In addition, in order to better understand the present invention, definitions and explanations of related terms are provided below.

As used herein, the terms "FXI protein", "FXI antigen" and "FXI" are used interchangeably and refer to coagulation factor XI protein of various species. The terms "FXIa protein", "FXIa antigen" and "FXIa" are used interchangeably and refer to activated factor XI protein of various species. The terms "FXI" and "FXIa" (and similar terms) comprise mutants and variants of natural FXI and FXIa proteins respectively, and the mutants and variants have the substantially same amino acid sequence as the natural primary structure (amino acid sequence) as described in the present invention.

In the context, the terms "coagulation and coagulation cascade", "coagulation cascade model" and similar terms are well known, referring to a process in which a coagulation pathway leads to the production of thrombin by a proteolytic cascade, which then converts soluble fibrinogen into fibrin that forms a clot. Various enzymes of this pathway are present in the plasma in the form of zymogen (inactive form), and when activated they undergo proteolytic cleavage to release active coagulation factors. The process of thrombin production can be divided into three stages: internal and external pathways, and final common pathway.

As used herein, the term "antibody" refers to an immunoglobulin molecule usually composed of two pairs of polypeptide chains (each pair has a light chain (LC) and a heavy chain (HC)). Antibody light chains can be classified into κ (kappa) and λ (lambda) light chains. Heavy chains can be classified into μ, δ, γ, α or ε heavy chains, and the isotypes of antibody are therefore defined as IgM, IgD, IgG, IgA and IgE, respectively. Within the light and heavy chains, the variable and constant regions are connected by a "J" region of about 12 or more amino acids, and the heavy chain also includes a "D" region of about 3 or more amino acids. Each heavy chain is composed of a heavy chain variable region (VH) and a heavy chain constant region (CH). The heavy chain constant region is composed of 3 domains (CH1, CH2 and CH3). Each light chain is composed of a light chain variable region (VL) and a light chain constant region (CL). The light chain constant region consists of one domain CL. The constant domains are not directly involved in the binding of antibodies and antigens, but exhibit a variety of effector functions, such as mediating the binding of immunoglobulins to host tissues or factors, including various cells (for example, effector cells) of immune system and the first component (C1q) of classical complement system. The VH and VL regions can also be subdivided into hypervariable regions (called complementarity determining regions (CDR)), interspersed with more conservative regions (called framework regions (FR)). Each VH and VL consists of 3 CDRs and 4 FRs arranged in the following order: FR1, CDR1, FR2, CDR2, FR3, CDR3, FR4 from the amino terminus to the carboxy terminus. The variable regions (VH and VL) of each heavy chain/light chain pair form antigen binding sites respectively. The assignment of amino acids in each region or domain may follow the numbering system such as IMGT, Kabat, Chothia or AbM.

Herein, unless the context clearly dictates otherwise, when the term "antibody" is referred to, it includes not only an intact antibody but also antigen-binding fragments of the antibody.

As used herein, the term "complementarity determining region" or "CDR" refers to the amino acid residues in the variable region of an antibody that are responsible for antigen binding. The precise boundaries of these amino acid residues can be defined according to various numbering systems known in the art, for example, according to the definitions in the Kabat numbering system (Kabat et al., Sequences of Proteins of Immunological Interest, 5th Ed. Public Health Service, National Institutes of Health, Bethesda, Md., 1991), Chothia numbering system (Chothia & Lesk (1987) J. Mol. Biol. 196: 901-917; Chothia et al. (1989) Nature 342: 878-883), IMGT numbering system (Lefranc et al., Dev. Comparat. Immunol. 27: 55-77, 2003), or AbM numbering system (Martin A C R, Cheetham J C, Rees A R, Proc Natl Acad Sci USA 86: 9268-9272, 1989). For a given antibody, those skilled in the art can easily identify the CDRs defined by each numbering system. Moreover, the correspondence between different numbering systems is well known to those skilled in the art (e.g., see Lefranc et al., Dev. Comparat. Immunol. 27: 55-77, 2003).

As used herein, the term "framework region" or "FR" residues refers to those amino acid residues in the variable region of an antibody other than the CDR residues as defined above.

As used herein, the term "germline antibody gene" is an immunoglobulin sequence encoded by non-lymphocytes, which has not undergone a process that can lead to genetic rearrangement and maturation for expression of a particular immunoglobulin. One advantage provided by various embodiments of the present invention is derived from the recognition that a germline antibody gene retains more important amino acid sequence structures characterizing individual animal species than a mature antibody gene. Therefore, when applied therapeutically to this species, it is less recognized as a foreign substance by this species.

The term "antibody" is not limited by any specific method for producing antibodies. For example, it comprises recombinant antibody, monoclonal antibody, and polyclonal antibody. The antibody may be antibody of different isotypes, for example, IgG (e.g., IgG1, IgG2, IgG3 or IgG4 subtype), IgA1, IgA2, IgD, IgE or IgM antibody.

As used herein, the term "antigen-binding fragment" of an antibody refers to a polypeptide that is a full-length or partial fragment of the antibody, such as a polypeptide that is a fragment of a full-length antibody, which retains the ability to specifically bind to the same antigen to which the full-length antibody binds, and/or competes with the full-length antibody for specific binding to the antigen, which is also referred to as the "antigen-binding portion". See generally, Fundamental Immunology, Ch. 7 (Paul, W., ed., 2nd edition, Raven Press, NY (1989), which is incorporated herein by reference in its entirety for all purposes. The antigen-binding fragment of antibody can be produced by recombinant DNA technology or by enzymatic or chemical cleavage of an intact antibody. Non-limiting examples of antigen-binding fragment include Fab, Fab', F(ab')$_2$, Fd, Fv, dAb and complementarity determining region (CDR) fragment, single-chain antibody (e.g., scFv), chimeric antibody, diabody, linear antibody, nanobody (its technology is from Domantis), domain antibody (its technology is from Ablynx), and polypeptide of small fragment sufficient to have the specific antigen-binding ability of a full-length antibody. The engineered antibody variants are reviewed in Holliger et al., 2005; Nat Biotechnol, 23: 1126-1136.

As used herein, the term "full-length antibody" refers to an antibody composed of two "full-length heavy chains" or "heavy chains" and two "full-length light chains" or "light chains", wherein the "full-length heavy chain" or "heavy chain" refers to a polypeptide chain that consists of a heavy chain variable region (VH), a heavy chain constant region CH1 domain, a hinge region (HR), a heavy chain constant region CH2 domain, and a heavy chain constant region CH3 domain in the N-terminal to C-terminal direction; and, when the full-length antibody is of the IgE isotype, it optionally also comprises a heavy chain constant region CH4 domain. Preferably, the "full-length heavy chain" is a polypeptide chain composed of VH, CH1, HR, CH2 and CH3 in the N-terminal to C-terminal direction. The "full-length light chain" or "light chain" is a polypeptide chain composed of a light chain variable region (VL) and a light chain constant region (CL) in the N-terminal to C-terminal direction. The two pairs of full-length antibody chains are connected by a disulfide bond between the CL and CH1 and a disulfide bond between the HR of the two full-length heavy chains. The full-length antibody of the present invention can be from a single species, such as a human; it can also be a chimeric antibody or a humanized antibody. The full-length antibody of the present invention comprises two antigen binding sites formed by a pair of VH and VL respectively, and the two antigen binding sites specifically recognize/bind the same antigen.

As used herein, the term "Fd fragment" refers to an antibody fragment composed of VH and CH1 domains; the term "dAb fragment" refers to an antibody fragment composed of VH domains (Ward et al., Nature 341:544 546 (1989)); the term "Fab fragment" refers to an antibody fragment composed of VL, VH, CL and CH1 domains; the term "F(ab')$_2$ fragment" refers to an antibody fragment comprising two Fab fragments connected by a disulfide bridge of the hinge region; the term "Fab' fragment" refers to a fragment obtained by reducing the disulfide bond connecting the two heavy chain fragments in F(ab')$_2$ fragment, consisting of an intact light chain and a heavy chain Fd fragment (consisting of VH and CH1 domains).

As used herein, the term "Fv fragment" refers to an antibody fragment composed of the VL and VH domains of a single arm of antibody. Fv fragment is generally considered to be the smallest antibody fragment that can form a complete antigen binding site. It is generally believed that six CDRs can confer antigen binding specificity to antibody. However, even a variable region (e.g., a Fd fragment, which contains only three antigen-specific CDRs) can recognize and bind an antigen, although its affinity may be lower than that of the complete binding site.

As used herein, the term "Fc fragment" refers to an antibody fragment formed with the second and third constant regions of first heavy chain and the second and third constant regions of second heavy chain of an antibody that are bound through a disulfide bond. The Fc fragment of antibody has many different functions, but does not participate in antigen binding.

As used herein, the term "scFv" refers to a single polypeptide chain comprising VL and VH domains, wherein the VL and VH are connected by a linker (see, for example, Bird et al., Science 242:423-426 (1988); Huston et al., Proc. Natl. Acad. Sci. USA 85:5879-5883 (1988); and Pluckthun, The Pharmacology of Monoclonal Antibodies, Volume 113, edited by Roseburg and Moore, Springer-Verlag, New York, pp. 269-315 (1994)). Such scFv molecule may have a general structure: $NH_2$-VL-linker-VH-COOH or $NH_2$-VH-linker-VL-COOH. A suitable linker of prior art consists of a repeated GGGGS amino acid sequence or variants thereof. For example, a linker having amino acid sequence (GGGGS)$_4$ can be used, but variants thereof can also be used (Holliger et al. (1993), Proc. Natl. Acad. Sci. USA 90: 6444-6448). Other linkers that can be used in the present invention are described by Alfthan et al. (1995), Protein Eng. 8:725-731, Choi et al. (2001), Eur. J. Immunol. 31: 94-106, Hu et al. (1996), Cancer Res. 56:3055-3061, Kipriyanov et al. (1999), J. Mol. Biol. 293:41-56 and Roovers et al. (2001), Cancer Immunol. In some cases, there may also be a disulfide bond between the VH and VL of scFv. As used herein, the term "di-scFv" refers to an antibody fragment formed by linking two scFvs.

As used herein, the term "diabody" refers to that its VH and VL domains are expressed on a single polypeptide chain, but the linker used is too short to allow the pairing between the two domains of the same chain, so that the domains are forced to pair with the complementary domains of another chain and create two antigen binding sites (see, for example, Holliger P. et al., Proc. Natl. Acad. Sci. USA 90: 6444-6448 (1993), and Poljak R J et al., Structure 2:1121-1123 (1994)).

Each of the aforementioned antibody fragments maintains the ability to specifically bind to the same antigen to which the full-length antibody binds, and/or compete with the full-length antibody for specific binding to the antigen.

As used herein, the term "multispecific antibody" refers to an antibody with multiple different antigen binding specificities, including, for example, bispecific antibody, trispecific antibody, and tetraspecific antibody. "Bispecific antibody" refers to an antibody with two different antigen binding specificities, which is formed by conjugating of a first antibody (or a fragment thereof) and a second antibody (or a fragment thereof) or antibody mimetics through a coupling arm, and the coupling methods include but are not limited to chemical reaction, gene fusion, protein fusion, polypeptide fusion and enzymatic reaction. Trispecific antibody is an antibody with three different antigen binding specificities, and tetraspecific antibody is an antibody with four different antigen binding specificities.

As used herein, "antibody mimetics" refers to substances that specifically bind to an antigen as an antibody does, but do not have the structure of antibody. They are usually artificial peptides or proteins with a molar mass of about 3 to 20 kDa, such as ankyrin repeat protein (DARPin®) and fynomer. The designed ankyrin repeat protein (DARPin®) is linked to IgG antibody, scFv-Fc antibody fragment or a combination thereof, as in described CN104341529A. The anti-IL-17a fynomer binds to anti-IL-6R antibody, as described in WO2015141862A1.

As used herein, "immunoglobulin" or "Ig" can refer to a type of protein that functions as an antibody. The antibodies expressed by B cells are sometimes called antigen receptors. The five members included in this class of proteins are IgA, IgG, IgM, IgD, and IgE, wherein IgG is the most common circulating antibody, which is the most effective immunoglobulin in agglutination, complement fixation and other antibody responses, and is important in defense against bacteria and viruses.

In this context, the antigen-binding fragment (e.g., the above-mentioned antibody fragment) of antibody can be obtained from a given antibody (e.g., the antibody provided by the present invention) using a conventional technique known to those skilled in the art (e.g., recombinant DNA technology or enzymatic or chemical fragmentation methods), and can be screened for specificity in the same manner by which intact antibodies are screened.

As used herein, the terms "monoclonal antibody" and "mAb" have the same meaning and are used interchangeably, which refer to an antibody or a fragment of an antibody derived from a group of highly homologous antibody molecules, that is, a group of identical antibody molecules except for natural mutations that may occur spontaneously. The monoclonal antibody has high specificity for a single epitope on antigen. Polyclonal antibodies are mentioned relative to the monoclonal antibody, and usually comprise at least two or more different antibodies, and these different antibodies usually recognize different epitopes on the antigen. In addition, the modifier "monoclonal" merely indicates the character of the antibody as being obtained from a highly homogeneous population of antibodies, and is not to be construed as requiring production of the antibody by any particular method.

The monoclonal antibody of the present invention can be prepared by a variety of techniques, such as hybridoma technology (see, for example, Kohler et al. Nature, 256:495, 1975), recombinant DNA technology (see, for example, U.S. Pat. No. 4,816,567), or phage antibody library technology (see, for example, Clackson et al. Nature352:624-628, 1991, or Marks et al. J. Mol. Biol. 222:581-597, 1991).

For example, monoclonal antibodies can be prepared as follows. The mice or other suitable host animals are first immunized with immunogen (with addition of an adjuvant if necessary). The method of injection of immunogen or adjuvant is usually multi-point subcutaneous injection or intraperitoneal injection Immunogen can be pre-coupled to certain known proteins, such as serum albumin or soybean trypsin inhibitors, to enhance the immunogenicity of the antigen in the host. The adjuvant may be Freund's adjuvant or MPL-TDM or the like. After the animal is immunized, the body will produce lymphocytes that secrete antibodies that specifically bind to the immunogen. In addition, lymphocytes can also be obtained by in vitro immunization. The lymphocytes of interest are collected and fused with myeloma cells using a suitable fusing agent, such as PEG, to obtain hybridoma cells (Goding, Monoclonal Antibodies: Principles and Practice, pp. 59-103, Academic Press, 1996). The hybridoma cells prepared above may be inoculated into a suitable culture medium which preferably contains one or more substances capable of inhibiting the growth of unfused, parental myeloma cells. For example, for parental myeloma cells lacking hypoxanthine guanine phosphotransferase (HGPRT or HPRT), the addition of hypoxanthine, aminopterin, and thymine (HAT medium) to the culture medium will inhibit growth of HGPRT-defective cells. Preferred myeloma cells should have a high fusion rate, stable antibody secretion capacity, and sensitivity to HAT culture medium. Among them, murine myeloma is preferred for myeloma cells, such as MOP-21 or MC-11 mouse tumor-derived strains (THE Salk Institute Cell Distribution Center, San Diego, Calif. USA), and SP-2/0 or X63-Ag8-653 cell line (American Type Culture Collection, Rockville, Md. USA). In addition, studies have also reported the use of human myeloma and human-murine heterologous myeloma cell lines to prepare human monoclonal antibodies (Kozbor, J. Immunol., 133: 3001 (1984); Brodeur et al., Monoclonal Antibody Production Techniques and Applications, pp 51-63, Marcel Dekker, Inc., New York, 1987). The culture medium for growing hybridoma cells is used to detect the production of monoclonal antibodies against specific antigens. Methods for determining the binding specificity of monoclonal antibodies produced by hybridoma cells include, for example, immunoprecipitation or in vitro binding assays such as radioimmunoassay (RIA), enzyme-linked immunosorbent assay (ELISA). For example, the affinity of the monoclonal antibody can be determined using the Scatchard assay described by Munson et al., Anal. Biochem. 107: 220 (1980). After determining the specificity, affinity, and reactivity of the antibody produced by the hybridoma, the cell strain of interest can be subcloned by the standard limiting dilution method described in Goding, Monoclonal Antibodies: Principles and Practice, pp. 59-103, Academic Press, 1996. A suitable culture medium may be DMEM or RPMI-1640 or the like. In addition, hybridoma cells can also be grown in animals in the form of ascites tumors. Utilizing traditional immunoglobulin purification methods, such as protein A agarose gel, hydroxyapatite chromatography, gel electrophoresis, dialysis or affinity chromatography, the monoclonal antibodies secreted by the subcloned cells can be isolated from the cell culture medium, ascites or serum.

Monoclonal antibodies can also be obtained by genetic engineering recombinant techniques. A DNA molecule encoding the heavy chain and light chain genes of a monoclonal antibody can be isolated from a hybridoma cell by PCR amplification using a nucleic acid primer that specifically binds to the monoclonal antibody heavy chain and light chain genes. The obtained DNA molecule is inserted into an expression vector, and then transfected into a host cell (such as *E. coli* cells, COS cells, CHO cells, or other myeloma cells that do not produce immunoglobulin), and cultured under appropriate conditions, thereby obtaining the desired recombinant antibody.

Antibodies can be purified by known techniques, such as affinity chromatography using protein A or protein G. A specific antigen (a target molecule recognized by an antibody) or its epitope can be immobilized on a column, and the immunospecific antibody can be purified by immunoaffinity chromatography. The purification of immunoglobulins may refer to, for example, D. Wilkinson (The Scientist, published by The Scientist, Inc., Philadelphia Pa., Vol. 14, No. 8 (Apr. 17, 2000), pp. 25-28).

As used herein, the term "murine antibody" refers to an antibody that is prepared by fusing B cells of immunized mice with myeloma cells, selecting murine hybrid fusion cells that can proliferate indefinitely and secrete the antibody, followed by screening, antibody preparation and antibody purification; or an antibody that is secreted by plasma cells which is formed by differentiation and proliferation of B cells after antigen invades the mouse body.

As used herein, the term "Chimeric antibody" refers to an antibody in which a portion of the light or/and heavy chain thereof is derived from one antibody (which may be derived from a specific species or belong to a certain specific antibody class or subclass), and another portion of the light chain or/and heavy chain is derived from another antibody (which may be derived from the same or different species or belong to the same or different antibody class or subclass), nonetheless, it still retains binding activity to the antigen of interest (U.S. Pat. No. 4,816,567 to Cabilly et al.; Proc. Natl. Acad. Sci. USA, 81:6851 6855 (1984)). For example, the term "chimeric antibody" can include an antibody (e.g., a human-murine chimeric antibody) wherein the heavy and light chain variable regions of the antibody are derived from a first antibody (e.g., a murine antibody), while the heavy chain and light chain constant regions of the antibody are derived from a second antibody (e.g., a human antibody).

As used herein, the term "humanized antibody" refers to a genetically engineered non-human antibody whose amino acid sequence has been modified to increase homology to the sequence of a human antibody. Generally, all or part of the CDR regions of a humanized antibody are derived from a non-human antibody (donor antibody), and all or part of the non-CDR regions (e.g., variable region FRs and/or constant region) are derived from a human immunoglobulin (receptor antibody). Humanized antibodies typically retain the desired properties of the donor antibody, including, but not limited to, antigen specificity, affinity, reactivity, ability to increase immune cell activity, ability to enhance an immune response, and the like. A donor antibody can be an antibody from mouse, rat, rabbit, or non-human primate (e.g., cynomolgus) having desirable properties (e.g., antigen specificity, affinity, reactivity, ability to increase immune cell activity and/or enhance immune response).

Humanized antibody can not only retain the expected properties of non-human donor antibody (e.g., murine antibody), but also effectively reduce the immunogenicity of non-human donor antibody (e.g., murine antibody) in a human subject, and thus is particularly advantageous. However, due to the matching problem between the CDR of donor antibody and the FR of receptor antibody, the expected properties of humanized antibody (e.g., antigen specificity, affinity, reactivity, ability to improve immune cell activity, and/or ability to enhance immune response) are generally lower than that of the non-human donor antibody (e.g., murine antibody).

Therefore, although researchers in the field have carried out in-depth research on the humanization of antibodies and have made some progresses (see, for example, Jones et al., Nature, 321:522 525 (1986); Reichmann et al., Nature, 332: 323 329 (1988); Presta, Curr. Op. Struct. Biol., 2:593 596 (1992); and Clark, Immunol. Today 21: 397 402 (2000)), the prior art does not provide detailed guidance on how to fully humanize donor antibody so that the humanized antibody produced not only has the highest degree of humanization, but also retains the expected properties of the donor antibody as much as possible. Technicians need to perform exploration, investigation and modification for a specific donor antibody, and pay a lot of creative work to obtain a humanized antibody that not only has a high degree of humanization (for example, a humanization degree of at least 75%, at least 80%, at least 85%, at least 90%, at least 91%, at least 92%, at least 93%, at least 94%, at least 95%, at least 96%, at least 97%, at least 98%, at least 99%), but also retains the expected properties of the specific donor antibody.

In the present invention, in order to make the humanized antibody retain the properties (including, for example, antigen specificity, affinity, reactivity, ability to improve immune cell activity and/or ability to enhance immune response) of the donor antibody as much as possible, the framework region (FR) of the humanized antibody of the present invention may comprise both the amino acid residues of human receptor antibody and the amino acid residues of corresponding non-human donor antibody.

The chimeric antibody or humanized antibody of the present invention can be prepared based on the sequence of the murine monoclonal antibody prepared above. The DNA encoding the heavy and light chains can be obtained from the target murine hybridoma and engineered using standard molecular biology techniques to contain non-mouse (e.g., human) immunoglobulin sequences.

To prepare a chimeric antibody, a variable region of murine immunoglobulin can be linked to a constant region of human immunoglobulin using a method known in the art (see, for example, U.S. Pat. No. 4,816,567 to Cabilly et al.). For example, a DNA encoding VH is operably linked to another DNA molecule encoding heavy chain constant region so as to obtain a full-length heavy chain gene. The sequence of human heavy chain constant region gene is known in the art (see, for example, Kabat, EA et al. (1991) Sequences of Proteins of Immunological Interest, Fifth Edition, U.S. Department of Health and Human Services, NIH Publication No. 91-3242), a DNA fragment containing these regions can be obtained by standard PCR amplification. The heavy chain constant region may be an IgG1, IgG2, IgG3, IgG4, IgA, IgE, IgM or IgD constant region, but is generally preferably an IgG1 or IgG4 constant region. For example, a DNA encoding VL is operably linked to another DNA molecule encoding light chain constant region CL so as to obtain a full-length light chain gene (as well as a Fab light chain gene). The sequence of human light chain constant region gene is known in the art (see, for example, Kabat, EA et al. (1991) Sequences of Proteins of Immunological Interest, Fifth Edition, US Department of Health and Human Services, NIH Publication No. 91-3242), a DNA fragment containing these regions can be obtained by standard PCR amplification. The light chain constant region may be a κ or λ constant region, but is generally preferably a κ constant region.

To prepare a humanized antibody, murine CDR regions can be grafted onto a human framework sequence by using any methods known in the art (see U.S. Pat. No. 5,225,539 to Winter; U.S. Pat. Nos. 5,530,101, 5,585,089, 5,693,762, and 6,180,370 to Queen et al.; And Lo, Benny, K C, editor, in Antibody Engineering: Methods and Protocols, volume 248, Humana Press, New Jersey, 2004). Alternatively, a transgenic animal can also be used, which is capable of producing a complete human antibody library without producing an endogenous immunoglobulin after immunization. For example, it has been reported that the homozygous deletion of the antibody heavy chain joining region (JH) gene in chimeric and germ-line mutant mice results in complete inhibition of endogenous antibody production, and transfer of the human germ-line immunoglobulin gene array in such germ-line mutant mice will result in the production of human antibodies upon antigen challenge (see, for example, Jakobovits et al., 1993, Proc. Natl. Acad. Sci. USA 90: 2551; Jakobovits et al., 1993, Nature 362: 255-258; Bruggermann et al., 1993, Year in Immunology 7: 33; and Duchosal et al., 1992, Nature 355: 258). Non-limiting examples of the above-mentioned transgenic animal include HuMAb mice (Medarex, Inc.) which comprises human immunoglobulin gene miniloci encoding unrearranged human heavy chains (μ and γ) and κ light chain immunoglobulin sequences, and a targeted mutation that inactivates endogenous μ and κ chain loci (see, for example, Lonberg et al. (1994) Nature 368 (6474): 856-859); or "KM mouse™" which carries a human heavy chain transgene and human light chain transchromosome (see: patent application WO02/43478). Other methods of humanizing antibodies include phage display technology (Hoogenboom et al., 1991, J. Mol. Biol. 227: 381; Marks et al., J. Mol. Biol. 1991, 222: 581-597; Vaughan et al., 1996, Nature Biotech 14: 309).

As used herein, the term "humanization degree" refers to an index used to evaluate the number of non-human amino acid residues in a humanized antibody. The humanization degree of a humanized antibody can be assessed, for example, by predicting the homology of the variable region sequence to the human V domain with the DomainGapAlign of IMGT website.

As used herein, "homologous antibody" refers to a variant of an antibody, in which the amino acid sequences in the heavy and light chain variable regions contained therein are homologous to the amino acid sequence of the antibody or antigen-binding fragment thereof provided herein, and the variant retains the desired functional properties of the antibody against FXI and/or FXIa of the present invention.

Methods of sequence alignment for comparison are well known in the art. Various procedures and alignment algorithms are described in: Smith T F and Waterman M S, Adv. Appl. Math., 2:482, 1981; Higgins D G and Sharp P M, CABIOS5:151, 1989. Altschul S F et al., Nature Genet., 6:119, 1994 provides detailed ideas for sequence alignment and homology calculations.

As used herein, the term "specific binding" refers to a non-random binding reaction between two molecules, such as a reaction between an antibody and an antigen to which it is directed. The strength or affinity of a specific binding interaction can be expressed in term of the equilibrium dissociation constant (KD) or half-maximum effect concentration (EC50) of the interaction.

The specific binding properties between two molecules can be determined using methods known in the art. One method involves measuring the rate of formation and dissociation of the antigen binding site/antigen complex. Both the "binding rate constant" (ka or kon) and the "dissociation rate constant" (kdis or koff) can be calculated from the concentration and the actual rate of association and dissociation (see Malmqvist M, Nature, 1993, 361: 186-187). The ratio of kdis/kon is equal to the dissociation constant $K_D$ (see Davies et al, Annual Rev Biochem, 1990; 59: 439-473). The $K_D$, kon and kdis values can be measured in any effective way. In certain embodiments, the dissociation constant can be measured using bioluminescence interferometry (e.g., the ForteBio Octet method). In addition, the dissociation constant can be measured by surface plasmon resonance techniques (for example, Biacore) or Kinexa.

As used herein, the term "vector" refers to a nucleic acid vehicle into which a polynucleotide can be inserted. When a vector enables the expression of a protein encoded by an inserted polynucleotide, the vector is referred to as an expression vector. A vector can be introduced into a host cell by transformation, transduction or transfection, so that the genetic material elements carried by the vector can be expressed in the host cell. Vectors are well known to those skilled in the art and include, but are not limited to: plasmids; phagemids; cosmids; artificial chromosomes, such as yeast artificial chromosomes (YAC), bacterial artificial chromosomes (BAC) or P1-derived artificial chromosomes (PAC); bacteriophages such as 2 phage or M13 phage and animal viruses. Animal viruses that can be used as vectors include, but are not limited to, retroviruses (including lentiviruses), adenoviruses, adeno-associated viruses, herpes viruses (e.g., herpes simplex virus), poxviruses, baculoviruses, papillomaviruses, papovavirus (e.g., SV40). A vector may comprise a variety of elements that control expression, including, but not limited to, promoter sequence, transcription initiation sequence, enhancer sequence, selection element, and reporter gene. In addition, the vector may comprise a replication initiation site.

Expression and cloning vectors contain a nucleic acid sequence that enables the vectors to replicate in one or more selected host cells. Generally, in cloning vectors, this sequence is one that enables the vector to replicate independently of the host chromosomal DNA, and includes an origin of replication or an autonomously replicating sequence. The term "expression vector" as used herein refers to a vector containing a recombinant polynucleotide, which comprises an expression control sequence operatively linked to the nucleotide sequence to be expressed. The expression vector contains sufficient cis-acting elements for expression; other elements for expression can be provided by host cells or in vitro expression systems. Expression vectors include all those known in the art, such as cosmids, plasmids (e.g., naked or contained in liposomes), and viruses (e.g., lentivirus, retrovirus, adenovirus, and adeno-associated virus).

As used herein, the term "host cell" refers to a cell into which a vector can be introduced, which includes, but is not limited to, prokaryotic cell such as *E. coli* or *Bacillus subtilis*, fungal cells such as yeast cells or *aspergillus*, insect cells such as S2 *drosophila* cells or Sf9, or animal cells such as fibroblast cells, CHO cells, COS cells, NSO cells, HeLa cells, BHK cells, HEK 293 cells, or human cells.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" means an amino acid substitution that does not adversely affect or alter the expected properties of a protein/polypeptide comprising an amino acid sequence, and the antibody variant obtained by conservative substitution retains the biological activity of its original sequence, such as specifically binding to FXI or FXIa. For example, conservative substitutions can be introduced by standard techniques known in the art, such as site-directed mutagenesis and PCR-mediated mutagenesis. Conservative amino acid substitutions include substitutions wherein an amino acid residue is substituted with another amino acid residue having a similar side chain, for example, a residue physically or functionally similar (e.g., having similar size, shape, charge, chemical properties, including ability of forming a covalent bond or a hydrogen bond, etc.) to the corresponding amino acid residue. A family of amino acid residues having similar side chains has been defined in the art. These families include amino acids having basic side chains (e.g., lysine, arginine, and histidine), acidic side chains (e.g., aspartic acid, glutamic acid), uncharged polar side chains (e.g., glycine, asparagine, glutamine, serine, threonine, tyrosine, cysteine, tryptophan), non-polar side chains (e.g. alanine, valine, leucine, isoleucine, valine, phenylalanine, methionine), beta branch side chains (e.g., threonine, valine, isoleucine) and aromatic side chains (e.g., tyrosine, phenylalanine, tryptophan, histidine). Therefore, it is preferred to replace the corresponding amino acid residue with another amino acid residue from the same side chain family Methods for identifying conservative substitutions of amino acids are well known in the art (see, for example, Brummell et al, Biochem. 32: 1180-1187 (1993); Kobayashi et al., Protein Eng. 12(10): 879-884 (1999); and Burks et al. Proc. Natl Acad. Set USA 94: 412-417 (1997), which is incorporated herein by reference).

The twenty conventional amino acids involved herein are expressed in routine manners. See, for example, Immunology-A Synthesis (2nd Edition, E. S. Golub and D. R. Gren, Eds., Sinauer Associates, Sunderland, Mass. (1991)), which is incorporated herein by reference. In the present disclosure, the terms "polypeptide" and "protein" have the same meaning and are used interchangeably. Also in the present disclosure, amino acids are generally represented by single letter and three letter abbreviations as known in the art. For example, alanine can be represented by A or Ala.

As used herein, the term "pharmaceutically acceptable carrier and/or excipient" as used herein refers to a carrier and/or excipient that is pharmacologically and/or physiologically compatible with the subject and the active ingredient, which is well known in the art (see, for example, Remington's Pharmaceutical Sciences. Edited by Gennaro AR, 19th ed. Pennsylvania: Mack Publishing Company, 1995) and includes, but is not limited to, pH adjusting agents, surfactants, adjuvants, ionic strength enhancers, diluents, agents that maintain osmotic pressure, agents that delay absorption, preservatives. For example, pH adjusting agents include, but are not limited to, phosphate buffers. Surfactants include, but are not limited to, cationic, anionic or nonionic surfactants such as Tween®-80. Ionic strength enhancers include, but are not limited to, sodium chloride. Preservatives include, but are not limited to, various antibacterial and antifungal agents, such as parabens, chlorobutanol, phenol, sorbic acid, and the like. Agents that maintain osmotic pressure include, but are not limited to, sugars, NaCl and the like. Agents that delay absorption include, but are not limited to, monostearate and gelatin. Diluents include, but are not limited to, water, aqueous buffers (such as buffered saline), alcohols and polyols (such as glycerin), and the like. Preservatives include, but are not limited to, various antibacterial and antifungal agents, such as thimerosal, 2-phenoxyethanol, parabens, chlorobutanol, phenol, sorbic acid, and the like. Stabilizers have the meaning commonly understood by those skilled in the art which can stabilize the desired activity of the active ingredient in the drug, including but not limited to sodium glutamate, gelatin, SPGA, sugars (e.g., sorbitol, mannitol, starch, sucrose, lactose, dextran, or glucose), amino acids (such as glutamic acid, glycine), proteins (such as dried whey, albumin or casein) or degradation products thereof (such as lactalbumin hydrolysate).

As used herein, the term "prevention" refers to a method performed to prevent or delay the occurrence of a disease or disorder or symptom (e.g., a disease or disorder associated with coagulation or thromboembolism) in a subject. As used herein, the term "treatment" refers to a method performed to obtain a beneficial or desired clinical result. For the purposes of the present invention, the beneficial or desired clinical result includes, but is not limited to, alleviating symptom, reducing the scope of disease, stabilizing (i.e., no longer exacerbating) the state of disease, delaying or slowing the development of disease, improving or alleviating the status of disease, and alleviating a symptom (either in part or in whole), alleviating or improving prognosis, reducing or suppressing disease recurrence, whether detectable or undetectable. In addition, the term "treatment" can also refer to prolonging survival time as compared to the expected survival time (if not receiving treatment).

As used herein, the term "subject" refers to a mammal, such as a primate mammal, such as a human. In certain embodiments, the subject (e.g., a human) suffers from a disease or disorder associated with coagulation or thromboembolism, or is at risk of suffering from the aforementioned diseases.

As used herein, the term "effective amount" refers to an amount sufficient to obtain or at least partially obtain the desired effect. For example, an effective amount for preventing a disease (e.g., a disease or disorder associated with coagulation or thromboembolism) refers to an amount sufficient to prevent, stop, or delay the occurrence of a disease (e.g., a disease or disorder associated with coagulation or thromboembolism); a therapeutically effective amount refers to an amount sufficient to cure or at least partially prevent a disease and its complications in a patient who has already suffered from the disease. It is completely within the abilities of those skilled in the art to determine such an effective amount. For example, the effective amount for therapeutic use will depend on the severity of the disease to be treated, the overall state of the patient's own immune system, the patient's general conditions such as age, weight and gender, the route of administering drug, and other therapies that are simultaneously administered and so on.

As used herein, the term "effector function" refers to those biological activities attributable to the Fc region of an antibody (Fc region of a natural sequence or an amino acid sequence variant), which varies as the isotype of an antibody. Examples of antibody effector functions include, but are not limited to, Fc receptor binding affinity, antibody-dependent cell-mediated cytotoxicity (ADCC), complement dependent cytotoxicity(CDC), antibody-dependent cellular phagocytosis (ADCP), downregulation of cell surface receptors (e.g., B cell receptors), B cell activation, cytokine secretion, half-life/clearance of antibodies and antigen-antibody complexes, and the like. Methods for altering the effector function of an antibody are known in the art, for example by introducing a mutation in the Fc region.

As used herein, the term "antibody-dependent cell-mediated cytotoxicity (ADCC)" refers to a form of cytotoxicity, in which cytotoxic effector cells specifically bind to the target cells to which the antigen is attached, through the binding of immunoglobulin to an Fc receptor (FcR) presented on cytotoxic cells (e.g., natural killer (NK) cells, neutrophils or macrophages), and then kills the target cells by secreting cytotoxins. Methods for detecting ADCC activity of an antibody are known in the art and can be evaluated, for example, by measuring the binding activity between an antibody to be tested and an Fc receptor (e.g., CD16a).

As used herein, the term "complement dependent cytotoxicity (CDC)" refers to a form of cytotoxicity in which the complement cascade is activated by the binding of complement component Cq to Fc of an antibody. Methods for detecting the CDC activity of an antibody are known in the art and can be evaluated, for example, by measuring the binding activity between an antibody to be tested and an Fc receptor (e.g., C1q).

As used herein, the term "FXI and/or FXIa-mediated" refers to the fact that FXI and/or FXIa mediate the endogenous coagulation pathway by directly or indirectly activating coagulation factor IX (also known as FIX), coagulation factor X (FX) and/or thrombin and/or by binding to platelet receptor.

As used herein, the term "disease or disorder associated with coagulation or thromboembolism" or similar terms refers to a disease or disorder caused by abnormal activation or non-natural inactivation of the coagulation pathway (e.g., in the absence of therapeutic means). Such diseases or disorders include (but are not limited to): thrombosis, thrombotic stroke, atrial fibrillation, stroke prevention associated with atrial fibrillation (SPAF), deep vein thrombosis, venous thromboembolism, acute coronary syndrome (ACS), ischemic stroke, acute limb ischemia, chronic thromboembolism pulmonary hypertension, systemic embolism, myocardial infarction (MI), acute myocardial infarction (AMI), stable angina pectoris, unstable angina pectoris, reocclusion and restenosis after coronary intervention, peripheral arterial occlusive disease (PAOD), renal vein thrombosis, transient ischemic attack (TIA), pulmonary thromboembolism, diffuse intravascular coagulation, thromboembolic disorder caused by medical device (e.g., catheter), severe systemic inflammatory response syndrome, metastatic cancer, infectious disease, organ failure (e.g., renal failure), toxicity caused by the administration of therapeutic protein in the body, multiple trauma, ischemia-reperfusion injury, local fibrin deposition, adult alveolar proteinosis, thromboembolic event (VTE) before and after joint replacement (TKA) surgery, coronary heart disease, thromboembolism after myocardial infarction, stroke in patient with non-valvular atrial fibrillation, thrombosis and thromboembolism in chronic kidney disease, thrombosis and thromboembolism in patients undergoing hemodialysis and patients undergoing extracorporeal membrane oxygenation, deep vein thrombosis (DVT), or pulmonary embolism (PE).

Catheter-induced thromboembolic disorders include the formation of thromboembolism in catheter (e.g., the use of Hickman catheters in tumor patients, and the use of extracorporeal membrane oxygenation (ECMO) may cause clots).

As used herein, the expression "prevention and/or treatment of a disease or disorder associated with coagulation or thromboembolism" may refer to using the antibody against FXI and/or FXIa or antigen-binding fragment thereof according to the present invention for prevention or treatment of one or more diseases or disorders as follows:

thromboembolism in an individual suspected or confirmed to have arrhythmia, such as sudden, persistent or permanent auricular fibrillation or atrial fibrillation;

stroke prevention in atrial fibrillation (SPAF), with a subgroup of AF patients undergoing percutaneous coronary intervention (PCI);

treatment of acute venous thromboembolic event (VTE) and prevention of prolonged secondary VTE in patients with high bleeding risk;

cerebral and cardiovascular events in the secondary prevention after transient ischemic attack (TIA) or non-disabling stroke and in the prevention of thromboembolic events in heart failure complicated by sinus rhythm;

clot formation and thromboembolism in left atrium of individuals undergoing cardioversion for arrhythmia;

thrombosis before, during and after the resection procedure for arrhythmia;

venous thrombosis, which includes (but does not exclude) treatment and secondary prevention of deep or superficial venous thrombosis in the lower or upper part, abdominal and thoracic vein thrombosis, sinus thrombosis and jugular vein thrombosis;

thrombus on any artificial surface in venous catheter or pacemaker lead;

pulmonary embolism in patients with or without venous thrombosis;

chronic thromboembolic pulmonary hypertension (CTEPH);

arterial thrombus on ruptured atherosclerotic plaque, thrombus on intra-arterial assistive devices or catheters, and thrombus in apparently normal arteries, such diseases including (but not limited to) acute coronary syndrome, ST elevation myocardial infarction, non-ST elevation myocardial infarction, unstable angina, stent thrombosis, thrombus on any artificial surface in the arterial system, and thrombus in the pulmonary artery of individuals with or without pulmonary hypertension;

thrombosis and thromboembolism in patients undergoing percutaneous coronary intervention (PCI);

psychogenic and cryptogenic stroke;

thrombosis in patients with invasive and non-invasive cancer malignancies;

thrombus on indwelling catheter;

thrombosis and thromboembolism in patients with severe diseases;

cardiac thrombosis and thromboembolism, including (but not exclusively) cardiac thrombosis after myocardial infarction, and cardiac thrombosis associated with conditions such as cardiac aneurysms, myocardial fibrosis, cardiac enlargement and dysfunction, myocarditis and artificial surfaces in heart;

thromboembolism in valvular heart disease patients with or without atrial fibrillation;

thromboembolism on valve mechanical or biological aids;

thromboembolism in patients with natural or artificial heart patches, arterial or venous catheters after heart repair of simple or complex heart malformations;

venous thrombosis and thromboembolism after knee replacement surgery, hip replacement surgery and orthopedic surgery, chest or abdominal surgery;

arterial or venous thrombosis after neurosurgery including intracranial and spinal cord intervention;

congenital or acquired thrombosis tendency, including (but not exclusively) coagulation factor V Leiden mutation, prothrombin mutation, deficiency of antithrombin III, protein C and protein S, coagulation factor XIII mutation, family afibrinogenemia, congenital plasminogen deficiency, increased coagulation factor XI content, sickle cell disease, antiphospholipid syndrome, autoimmune disease, chronic bowel disease, nephrotic syndrome, hemolytic uremia, myelodysplastic disease, disseminated intravascular coagulation, paroxysmal nocturnal hemoglobinuria, and heparin-induced thrombocytopenia;

thrombosis and thromboembolism in chronic kidney disease; and thrombosis and thromboembolism in patients undergoing hemodialysis and patients undergoing extracorporeal membrane oxygenation.

As used herein, the term "pharmaceutically acceptable" means that when a molecular itself, molecular fragment or composition is suitably administered to an animal or a human, it does not produce an adverse, allergic or other untoward reaction. Specific examples of some substances which can be used as a pharmaceutically acceptable carrier or a component thereof include sugars such as lactose, starch, cellulose and derivatives thereof, vegetable oils, gelatin, polyols such as propylene glycol, alginic acid and the like.

As used herein, combination therapy comprises using the antibody against FXI and/or FXIa or antigen-binding fragment thereof of the present invention in combination with one or more of additional active therapeutic agents (e.g., chemotherapeutic agents) or other preventive or therapeutic modes (e.g., antiplatelet drugs, anticoagulant drugs, thrombolytic drugs) for second therapy.

An exemplary antiplatelet drug for the second therapy is selected from aspirin, clopidogrel, prasugrel, ticagrelor, abciximab, eptifibatide, vorapaxar or any combination thereof.

An exemplary anticoagulant drug for the second therapy is selected from unfractionated heparin, heparin, low molecular weight heparin, warfarin, fondaparinux, edoxaban, betrixaban, rivaroxaban, apixaban, dabigatran etexilate, argatroban, bivalirudin or any combination thereof.

An exemplary thrombolytic drug for the second therapy is selected from streptokinase, urokinase, alteplase or prourokinase.

In this type of combination therapy, various active agents often have different complementary action mechanisms, and the combination therapy may result in a synergistic effect. The combination therapy may allow the reduction of dosage of one or more of the agents so as to reduce or eliminate adverse effects associated with one or more of the agents. Such type of combination therapy may have a synergistically therapeutic or preventive effect on potential diseases, disorders or conditions.

As used herein, "combination" includes therapies that can be administered separately, such as therapies separately formulated for separate administration (e.g., which may be provided in one kit), and therapies that can be administered together as a single formulation (i.e., "co-formulation"). In certain embodiments, the antibody against FXI and/or FXIa or antigen-binding fragment thereof according to the present invention can be administered sequentially. In other embodiments, the antibody against FXI and/or FXIa or antigen-binding fragment thereof can be administered simultaneously. The antibody against FXI and/or FXIa antibody or antigen-binding fragment thereof according to the present invention can be used in any combination with at least one other (active) agent.

As used herein, the term "about" refers to plus or minus 10% of the value stated in the context.

Since Chinese grammar have not a singular and plural rule as in English, "one or more" may be added before a noun when translating this disclosure into English.

The embodiments of the present invention will be described in detail below in conjunction with the accompanying drawings and examples. However, those skilled in the art will understand that the following drawings and examples are only used to illustrate the present invention, but not to limit the scope of the present invention. According to the accompanying drawings and the following detailed description of the preferred embodiments, the various objects and advantageous aspects of the present invention will become implementable for those skilled in the art.

SEQUENCE INFORMATION

Figure 1:
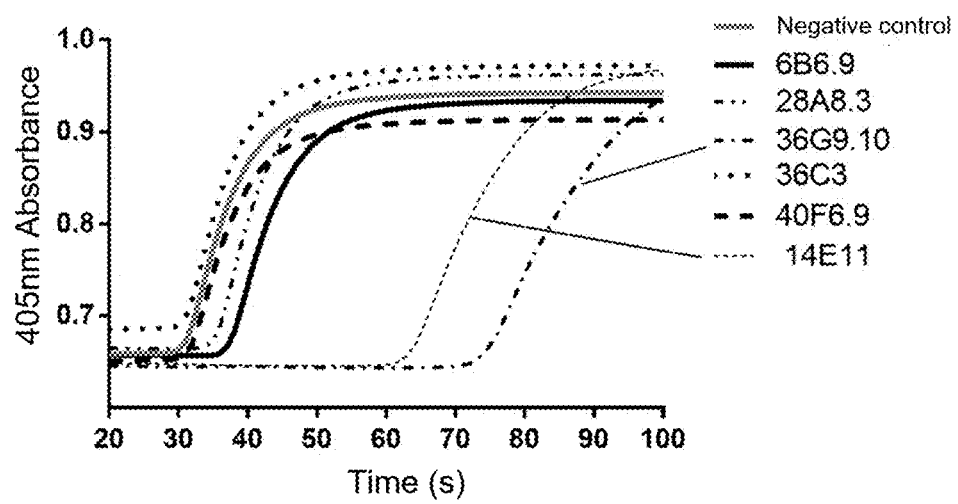
FIG. 1 shows the detection of APTT activity in hybridoma supernatant.

The information of the sequences involved in the present invention is described in the following table:

| SEQ ID NO | Description |
|---|---|
| 1 | Murine antibody 36G9.10 heavy chain variable region |
| 2 | Murine antibody 36G9.10 light chain variable region |
| 3 | IMGT 36G9.10 CDR-H1 |
| 4 | IMGT 36G9.10 CDR-H2 |
| 5 | IMGT 36G9.10 CDR-H3 |
| 6 | IMGT 36G9.10 CDR-L1 |
| 7 | IMGT 36G9.10 CDR-L2 |
| 8 | IMGT 36G9.10 CDR-L3 |
| 9 | AbM 36G9.10 CDR-H1 |
| 10 | AbM 36G9.10 CDR-H2 |
| 11 | AbM 36G9.10 CDR-H3 |
| 12 | AbM 36G9.10 CDR-L1 |
| 13 | AbM 36G9.10 CDR-L2 |
| 14 | AbM 36G9.10 CDR-L3 |
| 15 | Humanized antibody 36G9.10hz73/36G9.10hz74 heavy chain variable region |
| 16 | Humanized antibody 36G9.10hz43 heavy chain variable region |
| 17 | Humanized antibody 36G9.10hz92/36G9.10hz93 heavy chain variable region |
| 18 | Humanized antibody 36G9.10hz43/36G9.10hz73/36G9.10hz93 light chain variable region |
| 19 | Humanized antibody 36G9.10hz92 light chain variable region |
| 20 | Humanized antibody 36G9.10hz74 light chain variable region |
| 21 | Human IgG1 heavy chain constant region (N297A mutant) |
| 22 | Human κ light chain constant region |
| 23 | Humanized antibody 36G9.10hz73 heavy chain variable region nucleotide sequence |
| 24 | Humanized antibody 36G9.10hz73 light chain variable region nucleotide sequence |

| SEQ ID NO | Description |
|---|---|
| 25 | Humanized antibody 36G9.10hz73 heavy chain full length nucleotide sequence |
| 26 | Humanized antibody 36G9.10hz73 light chain full length nucleotide sequence |
| 27 | Murine antibody 36G9.10 heavy chain variable region nucleotide sequence |
| 28 | Murine antibody 36G9.10 light chain variable region nucleotide sequence |
| 29 | Murine antibody 7B2 heavy chain variable region |
| 30 | Murine antibody 7B2 light chain variable region |
| 31 | Humanized antibody 7B2hz11 heavy chain variable region sequence |
| 32 | Humanized antibody 7B2hz11 light chain variable region sequence |
| 33 | IMGT 7B2 CDR-H1 |
| 34 | IMGT 7B2 CDR-H2 |
| 35 | IMGT 7B2 CDR-H3 |
| 36 | IMGT 7B2 CDR-L1 |
| 37 | IMGT 7B2 CDR-L2 |
| 38 | IMGT 7B2 CDR-L3 |
| 39 | AbM 7B2 CDR-H1 |
| 40 | AbM 7B2 CDR-H2 |
| 41 | AbM 7B2 CDR-H3 |
| 42 | AbM 7B2 CDR-L1 |
| 43 | AbM 7B2 CDR-L2 |
| 44 | AbM 7B2 CDR-L3 |
| 45 | AbM 36G9.10hz73/36G9.10hz74 CDR-H2 |
| 46 | AbM 36G9.10hz43 CDR-H2 |
| 47 | AbM 7B2hz11 CDR-H2 |

EXAMPLES

The present invention will now be described with reference to the following examples which are intended to illustrate the present invention rather than limit the scope of the present invention.

Unless otherwise specified, the molecular biology experimental methods and immunoassay methods used in the present invention basically refer to J. Sambrook et al., Molecular Cloning: Laboratory Manual, 2nd Edition, Cold Spring Harbor Laboratory Press, 1989, and F. M. Ausubel et al., Short Protocols in Molecular Biology, 3rd Edition, John Wiley & Sons, Inc., 1995. Those skilled in the art know that the examples describe the present invention by way of illustration, and are not intended to limit the scope sought to be protected by the present invention.

Example 1

Preparation of Murine Anti-Human FXI/FXIa Monoclonal Antibody

The murine anti-human FXI/FXIa monoclonal antibody was obtained by using protein to immunize wild-type Balb/c mice. Each Balb/c mouse was injected subcutaneously with 25 µg of human FXIa (manufacturer: Haematologic Technologies, catalog number HCXI-0150) and 25 µg of human FXI (manufacturer: Haematologic Technologies, catalog number HCXI-0160) emulsified with CFA (complete Freund's adjuvant, manufacturer: Sigma, catalog number F5506) for the first immunization, and booster immunization was carried out once every two weeks, in which emulsion prepared with IFA (incomplete Freund's adjuvant, manufacturer: Sigma, catalog number: F5881) was used in the booster immunization. After immunization for three times, the serum titer was measured by ELISA. Booster immunization was performed 3 to 5 days before the fusion, and mice with higher titer were selected for intraperitoneal immunization with 10 µg of FXIa and 10 µg of FXI. The standard fusion process was adopted to fuse mouse spleen cells and Sp2/0-Ag14 (ATCC, Cat #CRL-1581) mouse myeloma cells in the mode of PEG fusion, and then HAT (manufacturer: Sigma, catalog number: H0262-10VL) was used for stressed screening, and ELISA screening was performed 14 days later. The specific method for ELISA screening comprised: 100 µL/well of 0.5 µg/mL biotin-labeled FXI (manufacturer: Haematologic Technologies, catalog number: HCXI-0150-B) was coated on an ELISA plate (manufacturer: Thermo Fisher Sci., catalog number: 5129) at room temperature for 1 hour. 200 µL of washing buffer (1X TBS comprising 0.5% Tween®-20) was used to perform washing for 3 times, 100 µL of hybridoma supernatant was added, and incubated at 37° C. for 1 hour. 200 µL of washing buffer was used to perform washing for 3 times, and 100 µL of Streptavidin-HRP (Pierce, Cat #21130) diluted in a ratio of 1:8000 was added and incubated at 37° C. for 1 hour. 200 µL of washing buffer was used to perform washing for 3 times, 100 µL of TMB (purchased from Thermo Fisher Sci., Cat #TMBW-1000-01) was added and allowed to develop for 10 minutes in the dark, and then 100 µL of stop solution (purchased from Thermo Fisher Sci., Cat #13361-100-10)was added, and reading was performed at 450 nm by a microplate reader.

The supernatants of 24,000 hybridoma clones were screened by ELISA, and 100 hybridoma clones capable of recognizing biotin-labeled FXI were obtained and transferred to 24-well plates. After 7 to 10 days, the hybridoma supernatants were tested by the APTT assay. The best 22 clones were subcloned by limiting dilution method to obtain monoclonal hybridomas. The monoclonal hybridomas were tested for their anticoagulant activity by the APTT assay by the activated partial thromboplastin time (APTT) kit (Activated Partial Thromboplastin Time Kit, manufacturer: Thermo Fisher Sci, catalog number 100402). The specific steps were as follows: 100 µL of normal human plasma (purchased from Innovative Research, Cat #IPLA-N) was added to a preheated test tube, then 100 µL of APTT reagent (purchased from Thermo Fisher Sci. Cat #100402TS) and 100 µL of the sample to be tested were added and mixed well, incubated at 37° C. for 5 minutes, then 100 µL of calcium chloride (purchased from Thermo Fisher Sci. Cat #100304, 20 mM) was added, the OD405 reading was measured, and the clotting time was calculated by curve fitting, in which Sp2/0-Ag14 cell supernatant was used as a negative control. 14E11 was used as a positive control antibody (prepared with reference to Aronora patent U.S. Pat. No. 8,388,959B2). The fold change shown in the APTT assay results was the ratio of the clotting time measured in the sample added with the experimental antibody to the clotting time measured in the control sample without the antibody. The fold change with a value of 1 or less indicated that the clotting time was not delayed or accelerated, while the fold change with a value of more than 1 indicated that the clotting time was prolonged.

As shown in FIG. 1, a total of 5 subclonal hybridoma supernatants were tested by APTT, in which 36G9.10 showed a prolonged APTT time, demonstrating a significant anticoagulant function, and could be used for further analysis, while the other clones 6B6.9, 28A8.3, 36C3 and 40F6.9 showed no significant difference in clotting time as compared to the negative control. Through the same screening method, hybridoma 7B2 with prolonged APTT time was obtained for further analysis.

The monoclonal hybridomas 36G9.10 and 7B2 were subjected to expanding culture without serum to 100-150 mL. The supernatants were purified by Protein G, and the purified murine antibodies were detected by HPLC-SEC, and their purity were all greater than 97%. The purified murine antibodies could be used for further function verification.

Example 2

Function Identification of Murine Anti-Human FXI/FXIa Monoclonal Antibody 2.1 Detection of the Function of Murine Anti-Human FXI/FXIa Antibody to Prolong Coagulation Using the APTT detection method in Example 1, under the conditions that antibodies were diluted to having a concentration of 2.00, 1.00, 0.50 and 0.25 µg/mL, 36G9.10 was compared to the positive control antibodies BAY-1213790 (prepared with reference to M007-H04 in Bayer patent WO2013167669) and 14E11, and PBS buffer was used as the negative control.

Figure 2A:
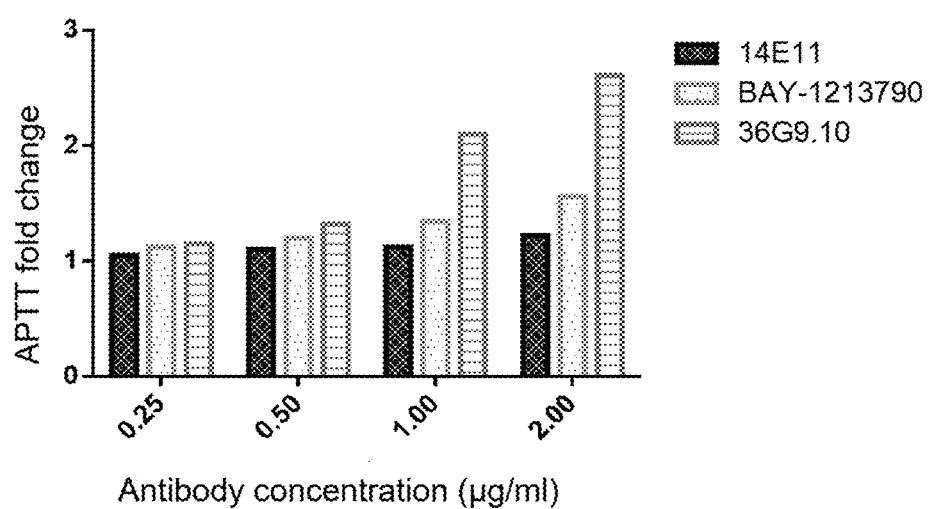
FIGS. 2A to 2B show the detection of clotting time of murine anti-human FXI/FIXa monoclonal antibody by APTT method.
Figure 2B:
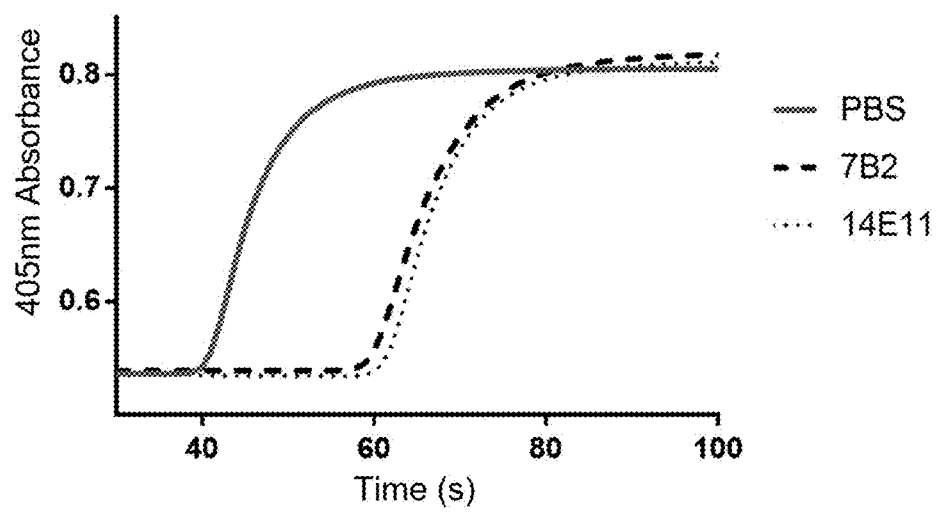

As shown in FIG. 2A, the candidate murine antibody 36G9.10 showed a significantly prolonged clotting time at each concentration as compared to the control antibodies BAY-1213790 and 14E11. Under the condition of antibody concentration of 5 µg/mL, 7B2 was compared with the positive control antibody 14E11, and PBS buffer was used as the negative control. The results were shown in FIG. 2B. The candidate murine antibody 7B2 showed a significantly prolonged clotting time as compared to PBS, and showed a prolonged clotting time equivalent to that of the positive control antibody 14E11.

2.2 Detection of the Activity of Murine Anti-Human FXI/FXIa Antibody to Inhibit FXIa from Catalyzing the Production of FXa and the Anticoagulant Function Thereof BIOPHEN™ Factor XIa kit (Hyphen BioMed, catalog number 220412) was used in the detection according to the kit instructions, and the release of para-nitroaniline (pNA) product was measured under OD405 nm to further confirm the activity of anti-FXI/FXIa antibody to inhibit FXIa from catalyzing the production of FXa. All antibodies had a detection concentration of 0.25 µg/mL. The stronger the function of anti-FXI/FXIa antibody blocking FXI/FXIa activity, the lower the OD405 nm signal value of the pNA product.

Figure 3:
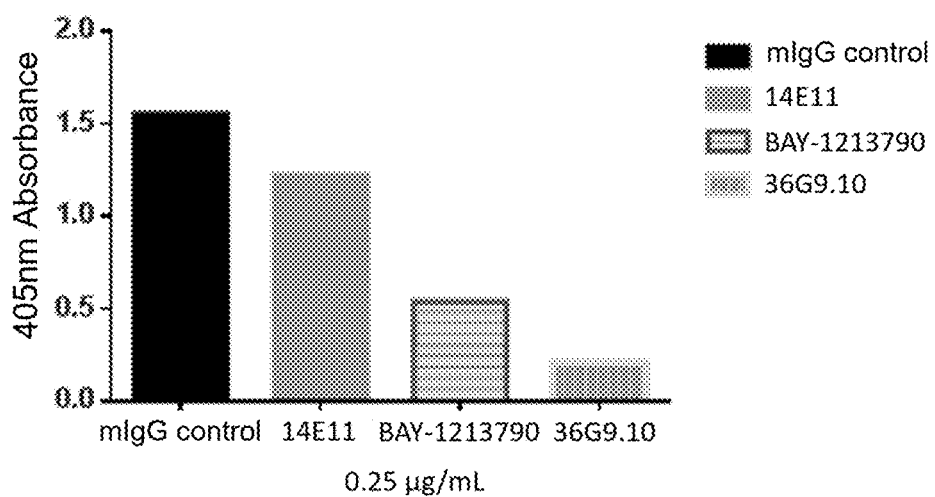
FIG. 3 shows the detection of anticoagulant function of murine anti-human FXI/FXIa monoclonal antibody by BIO-PHEN™ method.

The results were shown in FIG. 3. The 36G9.10 murine antibody showed a significantly stronger anticoagulant function than the control antibodies BAY-1213790 and 14E11.

2.3 Affinity Test of Murine Anti-Human FXI/FXIa Monoclonal Antibody

Octet ForteBio® was widely used in the detection of antibody-antigen dynamic affinity, and it was used to determine the dynamic affinity of the candidate murine antibody 36G9.10 and the control antibodies BAY1213790 and 14E11 to FXIa. The specific experimental steps were as follows: the streptavidin biosensors was first bound with the biotin-labeled antibody to be tested to reach a response signal value of 0.8 nm, then bound with FXIa protein (3.2, 1.6, 0.8, 0.4, 0.2, 0.1, 0.05, and 0 µg/mL) for 5 minutes, then dissociation was performed for 7 minutes, and the bivalent analysis model was used for all fitting analysis.

As shown in Table 1, the 36G9.10 showed a faster binding rate than those of the control antibodies 14E11 and BAY-1213790 (as shown by the Kon values), a slower dissociation rate than that of BAY-1213790 (as shown by the Kdis values), and an affinity stronger by 1.7 and 2.5 times than those of the control antibodies 14E11 and BAY-1213790, respectively.

TABLE 1

| Determination of dynamic affinity of murine anti-FXI/FXIa antibody to FXIa | | | | |
|---|---|---|---|---|
| Antibody name | KD (M) | Kon (1/Ms) | Kdis (1/s) | $R^2$ |
| 14E11 | 8.03E−10 | 7.65E+05 | 6.14E−04 | 0.9889 |
| BAY-1213790 | 1.19E−09 | 9.18E+05 | 1.09E−03 | 0.9786 |
| 36G9.10 | 4.80E−10 | 1.50E+06 | 7.20E−04 | 0.9831 |

2.4 Murine Anti-Human FXI/FXIa Antibody Specifically Blocks the Biological Activities of FXI and FXIa In order to confirm that the murine antibody 36G9.10 specifically blocked the biological activities of FXI and FXIa, human plasma lacking FXI (purchased from Innovative Research, catalog number: 50-643-396) was used, and APTT clotting time was determined by adding FXI (0.2, 0.4, 0.8 µg/mL), FXIa (0.2, 0.4, 0.8 µg/mL), FXI (0.4 µg/mL) and 36G9.10 (0.4 µg/mL), FXIa (0.4 µg/mL) and 36G9.10 (0.4 µg/mL).

Figure 4:
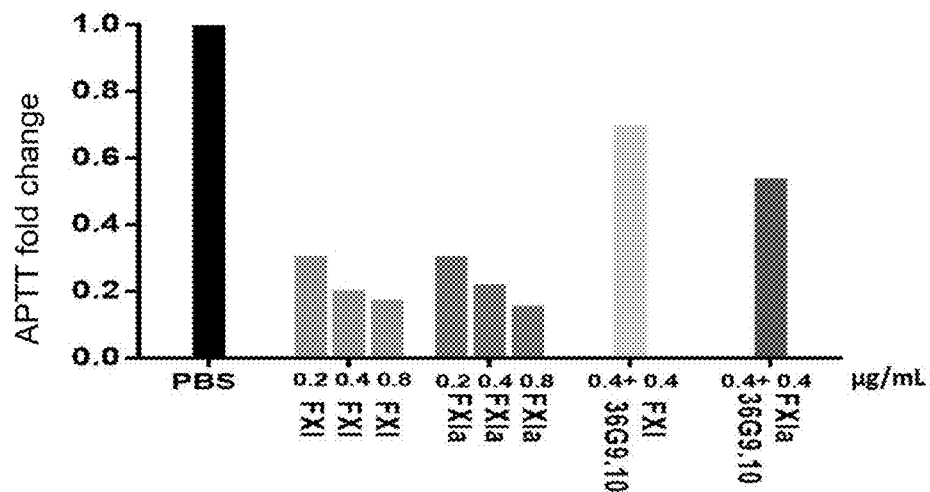
FIG. 4 shows the biological activity of murine anti-human FXI/FXIa monoclonal antibody to specifically block FXI and FXIa.

The results were shown in FIG. 4. The addition of FXI or FXIa could significantly shorten the clotting time of human plasma lacking FXI, and showed a dose-dependent relationship. When 36G9.10 murine antibody was added, FXI and FXIa showed a significantly prolonged clotting time, indicating that the murine antibody 36G9.10 specifically inhibited the biological activities of FXI and FXIa.

Example 3

Subtype Identification and Variable Region Amplification of Murine Anti-Human FXI/FXIa Antibody In order to identify the antibody subtypes of the candidate hybridoma clones, Pierce Rapid Isotyping kit (purchased from Thermo Fisher Sci. Cat #26179) was used to identify the antibody subtypes of the candidate clones 36G9.10 and 7B2. The identification results showed that the candidate clones had a heavy chain of IgG1 subtype, and a light chain of Kappa subtype.

The hybridoma cells were cultured to have a number of about 8000, the cells were lysed and subjected to the synthesis of first strand cDNA by using a cDNA reverse transcription kit (purchased from Thermo Fisher Sci. Cat #18080-200). Special primers were used to amplify VH and VK genes from cDNA by PCR, and the PCR products were purified by DNA purification kit (purchased from Qiagen, Cat#28104) and ligated to TOPO vector (purchased from Thermo Fisher Sci. Cat #K457540). Approximately 12 clones were picked for each ligation reaction and sequenced. The sequences were analyzed by Vector NTI 11.5 (purchased from Thermo Fisher Sci.) and Sequencer 5.4.6 (purchased from Genecodes), and the variable region sequences and CDR sequences of the murine anti-FXI/FXIa antibodies were obtained as shown in the sequence listing, in which the 36G9.10 murine antibody had a heavy chain variable region as shown in SEQ ID NO: 1, and a light chain variable region as shown in SEQ ID NO: 2; the 7B2 murine antibody had a heavy chain variable region as shown in SEQ ID NO: 29, and a light chain variable region as shown in SEQ ID NO: 30. Further, the chimeric antibodies 36G9.10-hz00 and 7B2-hz00 were constructed respectively for 36G9.10 and 7B2, which were obtained by grafting the heavy chain variable region sequence of 36G9.10 or 7B2 to the mutant human IgG1 heavy chain constant region (N297A mutant) (SEQ ID NO: 21), and grafting the light chain variable region sequence of 36G9.10 or 7B2 to the human Kappa light chain constant region (SEQ ID NO: 22).

Example 4

Humanization of Anti-Human FXI/FXIa Murine Antibody

The murine antibodies 36G9.10 and 7B2 were humanized by the humanization method of CDR grafting. In short, the humanization involves the following steps: the amino acid sequences of murine monoclonal antibody was compared with the amino acid sequence of human germline antibody to find a sequence with high homology and superior physical and chemical properties, which was used as a human germline framework sequence; analyzing and investigating HLA-DR affinity to select a human germline framework sequence with low affinity; then the six CDRs of the murine antibody were grafted into the selected heavy chain and light chain framework sequences.

Specifically, the heavy chain and light chain CDR regions of the murine antibodies 36G9.10 and 7B2 were respectively grafted into the corresponding humanized template FR. The heavy chain humanization templates for 36G9.10 were human germline gene sequence IGHV1-2*02 (see IMGT accession number X62106) and IGHV1-69-2*01 (see IMGT accession number KF698734), and the light chain humanization templates were human germline gene sequence IGKV1-33*01 (see IMGT accession number M64856) and IGKV1-16*01 (see IMGT accession number J00248). The heavy chain humanization template for 7B2 was human germline gene sequence IGHV1-69-2*01 (see IMGT accession number KF698734), and the light chain humanization template was human germline gene sequence IGKV1-39*01 (see IMGT accession number X59315).

Furthermore, by using computer simulation technology, the variable region and surrounding framework amino acid sequence thereof were analyzed by molecular docking so as to investigate its spatial binding form. By calculating the electrostatic force, van der Waals force, hydrophobicity and entropy value, the key amino acids in the amino acid sequence of the murine antibody that could interact with coagulation factor XIa and maintain the spatial structure were analyzed, and these murine amino acids were retained in the grafted antibody. That was, a series of back mutations were made to the FR region amino acid residues of the humanized template so that the humanized antibody retained the antigen-binding ability of the murine antibody as much as possible.

According to the above method, a total of 5 humanized antibodies were constructed on the basis of the CDRs of the murine antibody 36G9.10, where were named as 36G9.10-hz43, 36G9.10-hz73, 36G9.10-hz74, 36G9.10-hz92, 36G9.10-hz93, respectively; wherein the heavy chain constant region of each antibody was human IgG1 heavy chain constant region (N297A mutant) (SEQ ID NO: 21). Based on the CDRs of the murine antibody 7B2, the humanized antibody 7B2-hz11 was constructed, wherein the heavy chain constant region was mutant human IgG1 heavy chain constant regions (N297A mutant) (SEQ ID NO: 21). The light chain constant region sequence of the antibodies 36G9.10-hz73, 36G9.10-hz74, 36G9.10-hz43, 36G9.10-hz92, 36G9.10-hz93 and 7B2hz11 was SEQ ID NO: 22, none of which had ADCC and CDC effects.

The amino acid sequences of the variable and constant regions of the humanized antibodies were shown in Table 2.

TABLE 2

Amino acid sequences of variable and constant regions of humanized anti-human FXI/FXIa antibodies

| Name | Heavy chain variable region (SEQ ID NO:) | Light chain variable region (SEQ ID NO:) | Heavy chain constant region (SEQ ID NO:) | Light chain constant region (SEQ ID NO:) |
|---|---|---|---|---|
| 36G9.10-hz43 | 16 | 18 | 21 | 22 |
| 36G9.10-hz73 | 15 | 18 | | |
| 36G9.10-hz74 | 15 | 20 | | |
| 36G9.10-hz92 | 17 | 19 | | |
| 36G9.10-hz93 | 17 | 18 | | |
| 7B2-hz11 | 31 | 32 | | |

Example 5

Affinity Determination of Anti-Human FXI/FXIa Antibody

Octet Fortebio® was used for the affinity determination of chimeric and humanized antibodies. The main steps for the determination were as follows: firstly the chimeric and humanized antibodies (having a concentration of 0.3 µg/mL) were immobilized to AHC (anti-human-Fc) sensor, then FXI was subjected to 1:2 gradient dilution with an initial concentration of 3.2 µg/mL, and the association and dissociation rates of the chimeric and humanized antibodies were determined. The data obtained were analyzed by Octet data analysis software.

The results were shown in Table 3, which indicated that the chimeric antibody 36G9.10-hz00 and the humanized antibodies 36G9.10-hz43, 36G9.10-hz73, 36G9.10-hz74, 36G9.10-hz92, 36G9.10-hz93 all had an affinity KD stronger than that of the positive control BAY-1213790.

TABLE 3

Determination of the dynamic affinity of humanized anti-human FXI/FXIa antibodies to human FXI

| Antibody | Kinetic data | | |
|---|---|---|---|
|  | KD (M) | kon(1/Ms) | kdis(1/s) |
| BAY-1213790 | 3.74E−10 | 9.10E+05 | 3.40E−04 |
| 36G9.10-hz00 | 3.66E−12 | 6.52E+06 | 2.39E−05 |
| 36G9.10-hz43 | 4.41E−11 | 5.77E+06 | 2.55E−04 |
| 36G9.10-hz73 | 1.03E−11 | 6.31E+06 | 6.51E−05 |
| 36G9.10-hz74 | 7.98E−12 | 6.47E+06 | 5.16E−05 |
| 36G9.10-hz92 | 1.52E−11 | 5.07E+06 | 7.69E−05 |
| 36G9.10-hz93 | 8.81E−12 | 6.06E+06 | 5.34E−05 |

Example 6

Figure 5:
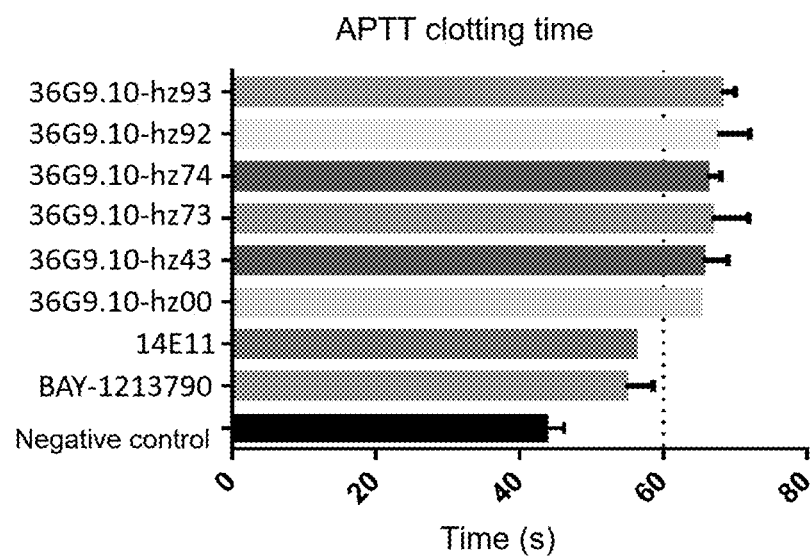
FIG. 5 shows the APTT anticoagulant activity test of humanized anti-human FXI/FXIa antibody.

Determination of APTT Anticoagulant Activity, Inhibition of the Activity of FXIa to Catalyze the Production of FXa and Anticoagulant Function of Chimeric and Humanized Anti-Human FXI/FXIa Antibodies The anticoagulant activity of the humanized antibodies was detected using the APTT Coagulation Test Kit, and the specific detection method was shown in Example 1. The results were shown in FIG. 5. The mean value and standard deviation were calculated by performing the determination for 4 times. The chimeric antibody 36G9.10-hz00 and the humanized antibodies 36G9.10-hz43, 36G9.10-hz73, 36G9.10-hz74, 36G9.10-hz92, 36G9.10-hz93 all showed a prolonged clotting time greater than those of the positive control antibodies 14E11 and BAY-1213790.

Using BIOPHEN™ Factor XIa kit (purchased from Aniara Cat #220412), the anticoagulant activity of the humanized antibodies was detected, and the specific method was shown in Example 2.

Figure 6:
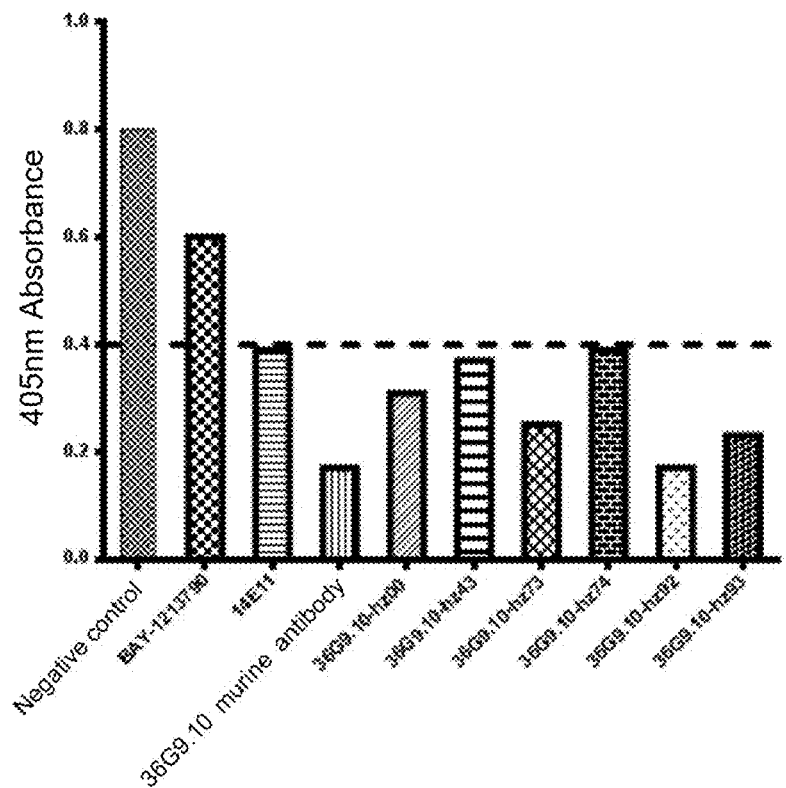
FIG. 6 shows the detection of anticoagulant function of humanized anti-human FXI/FXIa monoclonal antibody by BIOPHEN™ method.

The detection results were shown in FIG. 6, in which the chimeric antibody 36G9.10-hz00, the humanized antibodies 36G9.10-hz43, 36G9.10-hz73, 36G9.10-hz74, 36G9.10-hz92, 36G9.10-hz93, the antibodies 14E11 and BAY-1213790 all could effectively reduce the production of FXa, and the antibodies 36G9.10-hz43, 36G9.10-hz73, 36G9.10-hz92, 36G9.10-hz93 could more effectively reduce the production of FXa as compared to the control antibodies 14E11 and BAY-1213790, indicating that they had superior anticoagulant activity.

Example 7

Determination of Affinity of Humanized Anti-Human FXI/FXIa Antibody to FXI/FXIa

ELISA method was used to detect the affinity of 36G9.10-hz73 to human FXIa. The specific steps were as follows: FXIa antigen (Haematologic Technologies, HCXIA-160) was diluted to 1 μg/mL with CBS coating solution (0.32 g of Na$_2$CO$_3$, 0.59 g of NaHCO$_3$ were dissolved in deionized water, and diluted to 200 ml), and the coating of FXIa antigen at 100 μL/well was performed overnight at 4° C.; the liquid in the well was discarded on the next day, and washing was performed once with 300 μL of PBS; 100 μL of PBS (comprising 2% BSA, BOVOGEN, BSAS 1.0) was added, and subjected to blocking at 37° C. for 2 hours; PBS (comprising 2% BSA) was used to dilute antibodies 36G9.10-hz73 and BAY-1213790 (starting at 10 μg/mL, 4-fold dilution, 12 concentration points), 100 μL thereof was added to the corresponding well, and incubated at 37° C. for 2 hours; washing was performed with 300 μL of PBST for 3 times; HRP-labeled goat-anti-human secondary antibody (purchased from Jackson, 109-035-00) was subjected to 1:10000 dilution with PBS (comprising 2% BSA), and 100 μL thereof was added to the corresponding well, and incubated at 37° C. for 1 hour; washing was performed with 300 μL of PBST for 5 times; 100 μL of TMB color developing solution (purchased from BioPanda, TMB-S-004) was added to the corresponding well, and allowed to develop color at room temperature for 20 minutes; the color development was stopped with the addition of 50 μL of 2N H$_2$SO$_4$, and reading at OD450 nm was performed by using microplate reader (purchased from MD, SpectraMax M2) and the results were imported into Graphpad Prism for curve fitting.

Figure 7A:
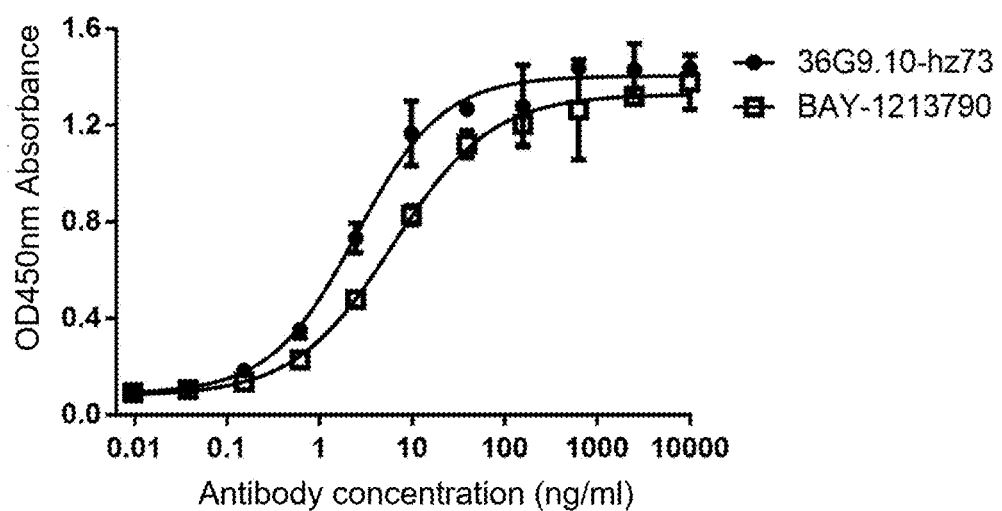
FIG. 7A shows the detection of affinity of humanized anti-human FXI/FXIa antibody to FXIa by ELISA.

The experimental results were shown in FIG. 7A, in which the affinity EC50 of 36G9.10-hz73 to FXIa was 2.488 ng/mL, and the affinity EC50 of BAY-1213790 to FXIa was 6.163 ng/mL, indicating that 36G9.10-hz73 was better than BAY-1213790.

ELISA method was used to detect the affinity of 36G9.10-hz73 to human FXI, in which FXI antigen (obtained by cloning PMD-F11 plasmid purchased from Sino Biological into PLVX-IRES-PURO vector and transfecting into 293F cell for expression) was diluted with CBS coating solution to 1 μg/mL, and the coating at 100 μL per well was performed overnight at 4° C. The remaining steps were as shown in the previous sections, except that the antibody had an initial concentration of 0.37 μg/mL, with 3-fold dilution and 9 concentration points.

Figure 7B:
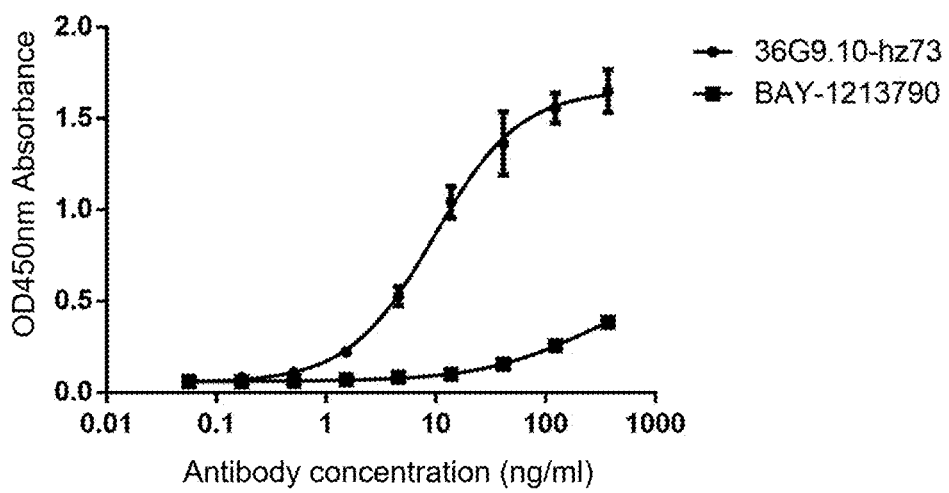
FIG. 7B shows the detection of affinity of humanized anti-human FXI/FXIa antibody to FXI by ELISA.

The experimental results were shown in FIG. 7B, in which the affinity EC50 of 36G9.10-hz73 to FXI was 9.68 ng/mL, and BAY-1213790 did not bind to FXI, indicating that 36G9.10-hz73 could neutralize FXI and FXIa at the same time and exert better anticoagulant function.

Example 8

Detection of Anti-Human FXI/FXIa Antibody Competing with Control Antibody for Binding to FXIa In order to determine whether 36G9.10-hz73, BAY-1213790 and 14E11 recognize the same epitope of FXIa, a competitive ELISA method was used for detection. The specific steps were as follows: FXIa antigen was diluted to 1 μg/mL with CBS coating solution, and the coating of FXIa antigen at 100 μL per well was performed at 4° C. overnight; the liquid in the well was discarded on the next day, and the washing was performed with 300 μL of PBS; 100 μL of PBS (comprising 2% BSA) was added and subjected to blocking at 37° C. for 2 hours; the biotin-labeled 36G9.10-hz73 antibody was diluted with PBS (comprising 2% BSA) to 10 ng/mL, and this was used as a mother solution to dilute the antibodies BAY-1213790 and 14E11 to 10 μg/mL, 100 μL thereof was added into the corresponding well, 10 μg/mL 36G9.10-hz73 antibody was used as a positive control, 10 ng/mL biotin-labeled 36G9.10-hz73 antibody was used as a negative control, a blank control was also set, and they were all incubated at 37° C. for 2 hours; the washing was performed with 300 μL of PBST for 3 times; HRP-Streptavidin secondary antibody (purchased from Proteintech, SA00001-0) was subjected to dilution at a ratio of 1: 3000 with PBS (comprising 2% BSA), 100 μL thereof was added to the corresponding well, and incubated at 37° C. for 1 hour; washing was performed with 300 μL of PBST for 5 times; 100 4, of TMB color developing solution (purchased from BioPanda, TMB-S-004) was added to the corresponding well and allowed to develop color at room temperature for 20 minutes; the color development was stopped with the addition of 50 μL of 2N $H_2SO_4$, and the reading at OD450 nm was performed by a microplate reader (purchased from MD, SpectraMax M2) and the results were imported into Graphpad Prism for plotting.

Figure 8:
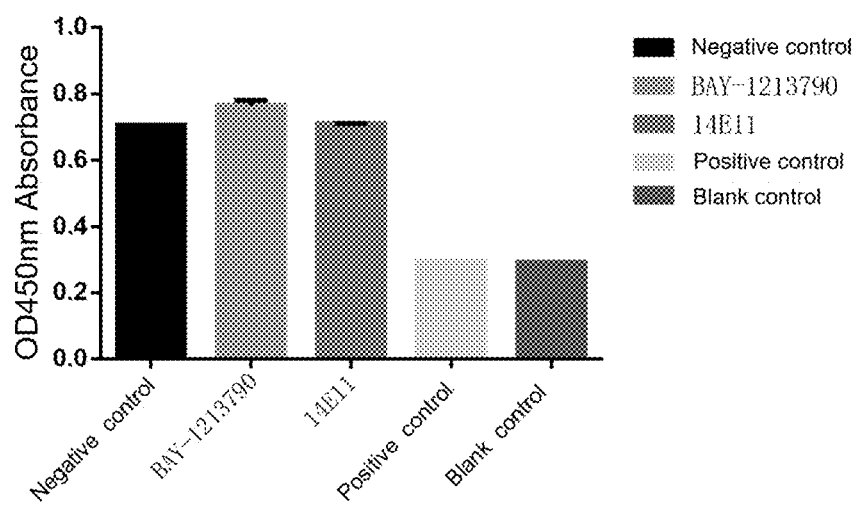
FIG. 8 shows the detection of humanized anti-human FXI/FXIa antibody competing with the control antibody BAY-1213790 for binding to FXIa.

The experimental results were shown in FIG. 8, in which BAY-1213790 and 14E11 did not compete with 36G9.10-hz73 for binding to FXIa, indicating that the former two and 36G9.10-hz73 bound to different epitopes of FXIa.

Example 9

Inhibition of the Catalytic Effect of FXIa on Substrate by Anti-Human FXI/FXIa Antibody In 1988, Shun-ichiro KAWABATA et al. screened out several FXIa-specific fluorescently labeled substrates for sensitive detection of human FIXa enzyme activity in vitro (see Eur. J. Biochem. 172, 17-25 (1988), for details). Therefore, by detecting the catalytic cleavage of the specific fluorescent substrate (1-1575, Bachem) by human FXIa, the activity of human FXIa and the effective neutralization of FXIa by the humanized anti-human FXI/FXIa antibody were determined. The specific steps were as follows: human FXIa was diluted to 1 nM with a buffer comprising 50 mM Tris/HCl, 100 mM NaCl, 5 mM $CaCl_2$ and 0.1% BSA, and this was used as a mother solution to serially dilute the antibodies 36G9.10-hz73 and BAY-1213790, with an initiative concentration of 20 μg/mL, 4-fold dilution, 14 concentration points; 10 μL of the diluted antibody was added to each well of a 384-well plate (purchased from Coring, 4514), and incubated at 37° C. for 1 hour; after incubation, 10 μL of fluorescent substrate 1-1575 with a concentration of 2 μM was added into each well, mixed and immediately measured by a microplate reader to continuously read the fluorescence values at 360/465 nm, which were imported into Graphpad Prism for curve fitting.

The experimental results were shown in Table 4, in which the antibody 36G9.10-hz73 could effectively inhibit the catalytic effect of FXIa on the fluorescent substrate, and had IC50 of 26.215 ng/mL, and BAY-1213790 had IC50 of 69.96 ng/mL, indicating that 36G9.10-hz73 was better than BAY-1213790.

TABLE 4

Inhibition of the catalytic effect of FXIa on fluorescent substrate by humanized anti-human FXI/FXIa antibody

| Antibody name | IC50 value (ng/mL) |
| --- | --- |
| 36G9.10-hz73 | 26.215 ± 3.365 (n = 2) |
| BAY-1213790 | 69.96 ± 7.44 (n = 2) |

Example 10

Detection of Anticoagulant Activity of Anti-Human FXI/FXIa Antibody by Measuring Activated Partial Thromboplastin Time (APTT)

After APTT reagent was added to anticoagulated plasma, the endogenous coagulation pathway was activated to activate XI to XIa, and an antibody targeting FXIa could inhibit the activity of FXIa, thereby prolonging APTT. Therefore, the determination of APTT was used to detect the anticoagulant activity of humanized anti-human FXI/FXIa antibody. The specific steps were as follows: venous blood from human, monkey, dog, rabbit and rat were collected respectively, 2 to 3 samples were taken for each species, 4 tubes of blood were taken for each sample (1.8 ml per tube), subjected to anticoagulation using 3.2% sodium citrate and centrifugation at 2500×g, 4° C. for 10 minutes, then the resultant plasma was taken and stored at 4° C. for later use (all plasma of each sample were combined); the antibody to be tested was diluted with physiological saline, starting at 1500 μg/mL, 3 concentration points, and used as a 10× mother solution of the antibody to be tested; at high concentration, the sample detection system was 150 μl, in which 135 μl of plasma was taken and added with 15 μl of the mother solution of the antibody to be tested (i.e., the mother solution of the antibody to be tested was diluted by 10 times), and then a fully-automated blood coagulation analyzer (purchased from Sysmex CA1500) was used to detect APTT; at low concentration, the sample detection system was 75 μl, in which 67.5 μl of plasma was taken and added with 7.5 μl of the mother solution of the antibody to be tested (i.e., the mother solution of the antibody to be tested was diluted by 10 times), and then APTT was detected with the fully-automated blood coagulation analyzer.

Figure 9A:
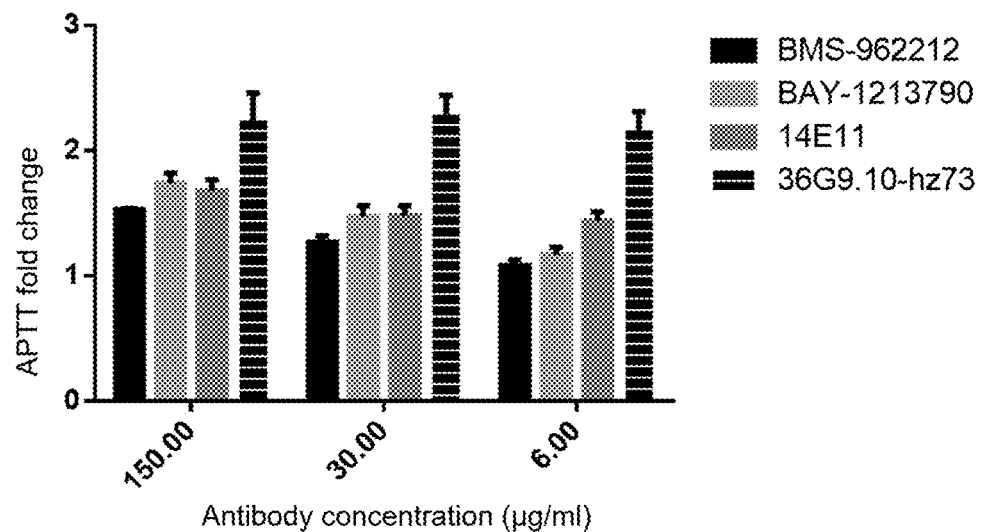
FIG. 9A shows the detection of anticoagulant activity of humanized anti-human FXI/FXIa antibody in human blood by measuring activated partial thromboplastin time (APTT)
Figure 9B:
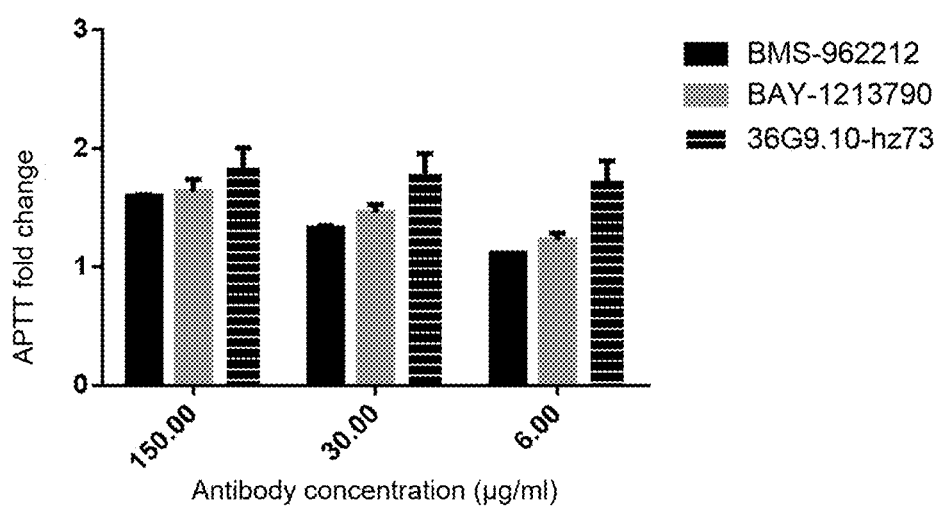
FIG. 9B shows the detection of anticoagulant activity of humanized anti-human FXI/FXIa antibody in monkey blood by measuring activated partial thromboplastin time (APTT)
Figure 9C:
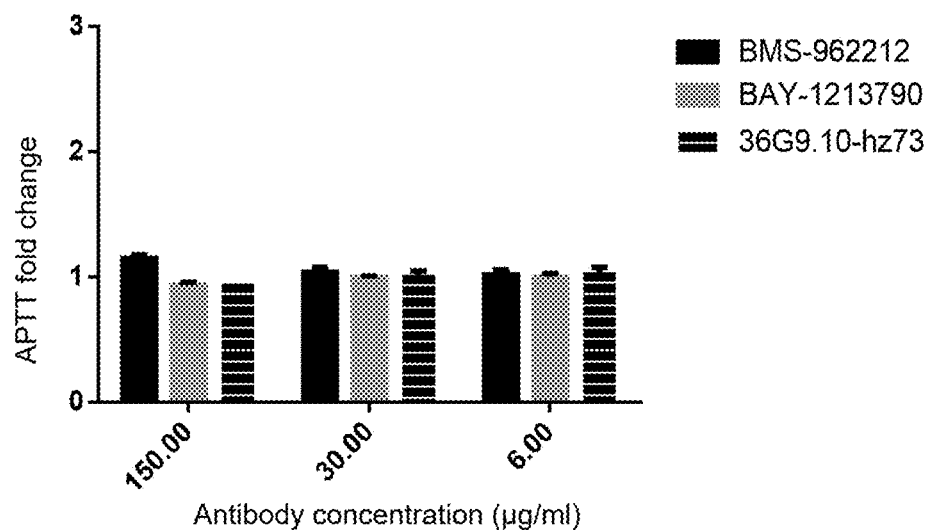
FIG. 9C shows the detection of anticoagulant activity of humanized anti-human FXI/FXIa antibody in dog blood by measuring activated partial thromboplastin time (APTT)
Figure 9D:
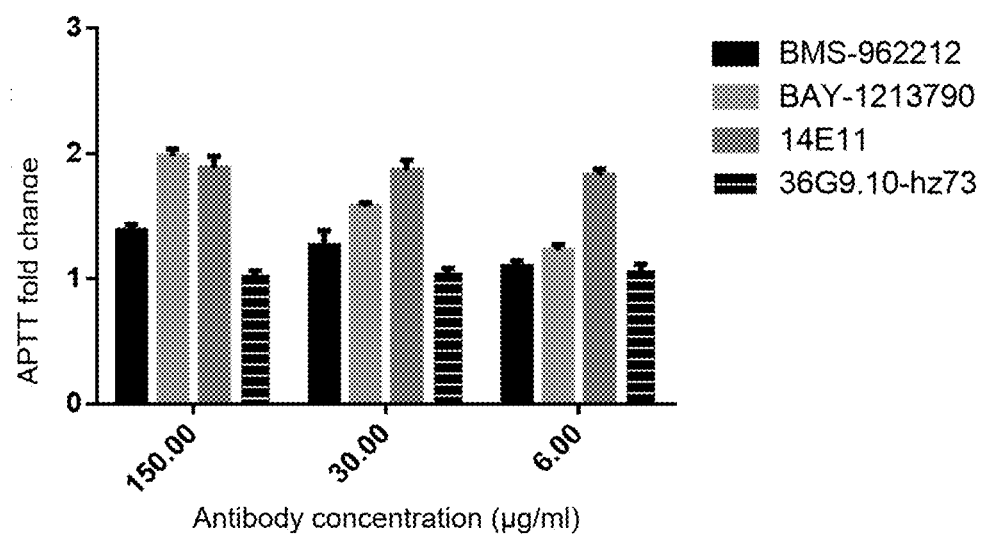
FIG. 9D shows the detection of anticoagulant activity of humanized anti-human FXI/FXIa antibody in rabbit blood by measuring activated partial thromboplastin time (APTT)
Figure 9E:
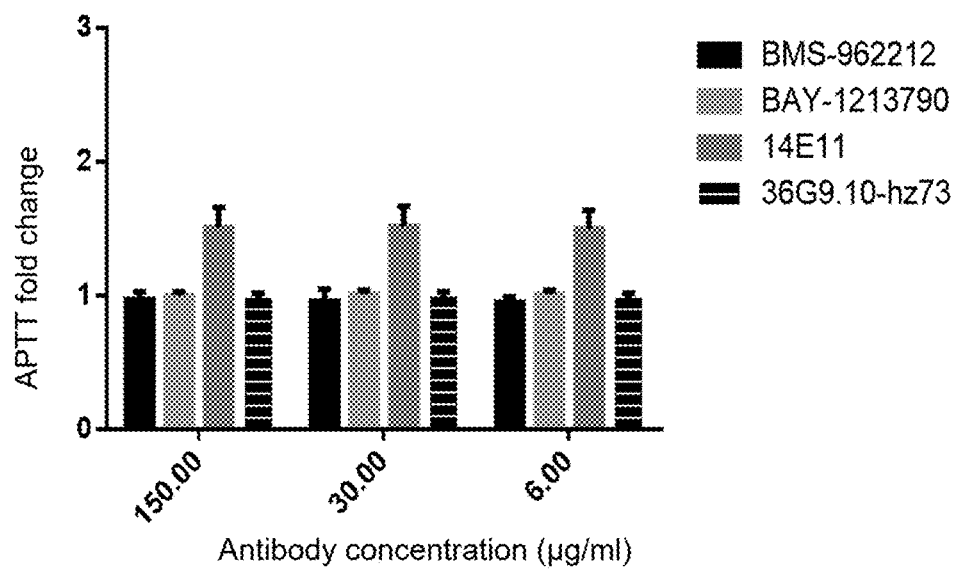
FIG. 9E shows the detection of anticoagulant activity of humanized anti-human FXI/FXIa antibody in rat blood by measuring activated partial thromboplastin time (APTT)

The results of the experiment were shown in FIG. 9A, in which all of the 4 tested antibodies 36G9.10-hz73, BAY-1213790, BMS-962212 (prepared by referring to J Med Chem. 2017 Dec. 14; 60(23): 9703-9723. doi: 10.1021/acs.jmedchem.7b01171. Epub 2017 Nov. 17) and 14E11 showed a prolonged APTT in human plasma, the 36G9.10-hz73 showed the best effect with a prolonged APTT by 2.2 times at 6 μg/mL, which was better than those of the other three. As shown in FIGS. 9B to 9E, 36G9.10-hz73 only prolonged APTT clotting time in monkey plasma, while BAY-1213790 prolonged APTT clotting time in plasma of monkey and rabbit, and 14E11 prolonged APTT clotting time in plasma of monkey, rabbit and rat, indicating that 36G9.10-hz73 was different from BAY-1213790 and 14E11 in term of species cross, so that it was speculated that 36G9.10-hz73 bound to an epitope of FXI/FXIa different from those to which BAY-1213790 and 14E11 bound.

The prothrombin time (PT) test mainly reflected the condition of the exogenous coagulation system. The fold change shown in the PT test results was a ratio of the clotting time measured in the sample added with the experimental antibody to the clotting time measured in the control sample without the antibody. The fold change with a value of 1 or less indicated that the clotting time was not delayed or accelerated, while the fold change with a value of more than 1 indicated that the clotting time was prolonged.

Using the same treatment method as above, the effects of 36G9.10-hz73, BAY-1213790, BMS-962212 and 14E11 on PT were detected with the fully-automated blood coagulation analyzer. The detection results were shown in Table 5, in which all samples did not prolong the PT (in terms of fold change) in the plasma of 5 species as compared with PBS control even at the concentration of 150 μg/mL (1 μM), indicating that they had no effect on exogenous coagulation, and did not increase the risk of bleeding.

TABLE 5

Detection of PT activity of humanized anti-human FXI/FXIa antibody

| Antibody name | Human | Monkey | Dog | Rabbit | Rat |
|---|---|---|---|---|---|
| 36G9.10-hz73 | 0.96 ± 0.04 | 1.00 ± 0.01 | 1.03 ± 0.01 | 0.99 ± 0.01 | 0.99 ± 0.01 |
| BAY-1213790 | 0.95 ± 0.05 | 1.00 ± 0.01 | 1.02 ± 0.01 | 0.99 ± 0.01 | 0.99 ± 0.01 |
| 14E11 | 0.95 ± 0.05 | / | / | 1.00 ± 0.01 | 1.00 ± 0.01 |
| BMS-962212 | 0.97 ± 0.06 | 0.99 ± 0.01 | 1.01 ± 0.01 | 1.00 ± 0.00 | 1.00 ± 0.01 |

Example 11

Detection of Accelerated Stability of Anti-Human FXI/FXIa Antibody

The antibody 36G9.10-hz73 was diluted with 20mM His-HCl (hydrochloric acid-histidine buffer) (comprising 0.03% Tween®-20, pH5.5) to a concentration of 11.5 mg/mL, and allowed to stand at 40° C. and 25° C. for 14 days and 28 days, respectively, then the APTT detection method in Example 4 was used to detect the anticoagulant activity of the sample after acceleration, and the purity of the antibody after acceleration was detected by SEC.

Figure 10:
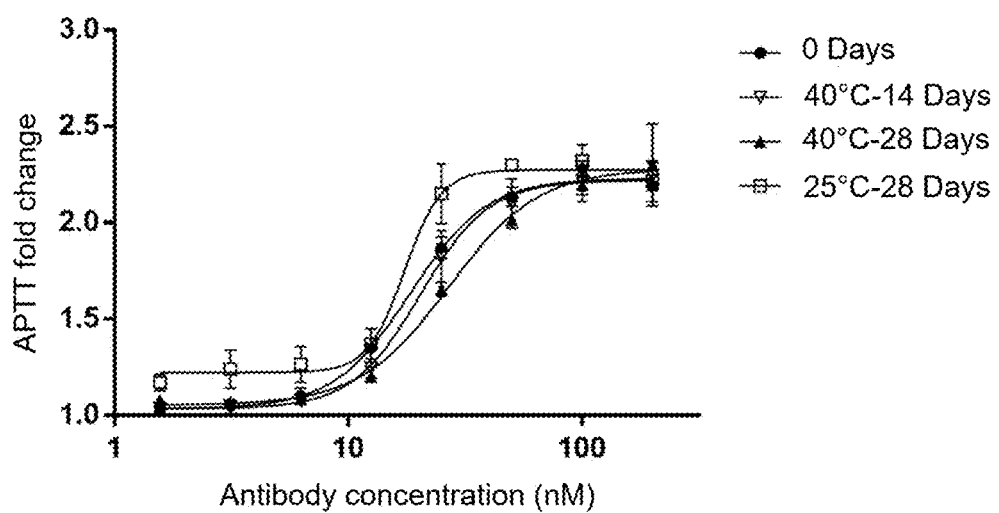
FIG. 10 shows the accelerated stability test of humanized anti-human FXI/FXIa antibody.

The experimental results were shown in FIG. 10 and Table 6, in which the antibody 36G9.10-hz73 stood at 40° C. and 25° C. for 14 days and 28 days showed no significant change in anticoagulant activity and purity.

TABLE 6

Detection of accelerated stability of humanized anti-human FXI/FXIa antibody

| Conditions of placement | Purity by SEC detection (%) | APTT detection (EC50, nM) |
|---|---|---|
| 0 days | 99.4 | 18.36 |
| 25° C.-28 days | 99.8 | 17.36 |
| 40° C.-14 days | 97.9 | 20.33 |
| 40° C.-28 days | 94.4 | 26.89 |

Example 12

Detection of Pharmacokinetics (PK) and Pharmacodynamics (PD) of Anti-Human FXI/FXIa Antibody In order to detect the PK and PD of 36G9.10-hz73 in vivo, different doses of antibody 36G9.10-hz73 was administered to cynomolgus monkeys by a single intravenous injection (IV) or subcutaneous injection (SC), and blood samples were taken at different time points to detect PK and APTT activity. The specific administration groups and dosages were shown in Table 7, in which the volume of one single intravenous injection or subcutaneous administration was 2 mL/kg, the intravenous injection site was the veins of the limbs, and the subcutaneous injection site was the back of the neck.

TABLE 7

Dosage regimen of humanized anti-human FXI/FXIa antibody for detection of PK and PD

| Group | Dose (mg/kg) | Administration mode | Number of animals | Gender of animals |
|---|---|---|---|---|
| 1 | 1 | Intravenous injection | 2 | 1 male + 1 female |
| 2 | 3 | Intravenous injection | 3 | 1 male + 2 female |
| 3 | 3 | Subcutaneous injection | 3 | 2 male + 1 female |

After completing the blood collection at all time points, the antibody 36G9.10-hz73 was used as the standard, and the antibody concentration standard curve was drawn using the ELISA method in Example 7, and the blood concentration of the antibody 36G9.10-hz73 at each time point was determined by using the standard curve under the same conditions, and finally the measured blood concentrations were imported into Graphpad Prism for curve fitting, and the PK of 36G9.10-hz73 in cynomolgus monkey was calculated.

At the same time, immediately after each blood sampling, the method in Example 10 was used to detect APTT, and finally the data at all time points were imported into Graphpad Prism for curve fitting, and the PD of 36G9.10-hz73 in cynomolgus monkey was calculated.

The PK test results were shown in Table 8, in which the intravenous injection of 3 mg/kg 36G9.10-hz73 antibody showed a half-life of 290.15 hours in cynomolgus monkeys, and the subcutaneous injection of 3 mg/kg 36G9.10-hz73 antibody showed a half-life of 188.02 hours in cynomolgus monkeys. The subcutaneous injection of 3 mg/kg 36G9.10-hz73 antibody showed a bioavailability of 94%±2% (n=2).

TABLE 8

Determination of PK of humanized anti-human FXI/FXIa antibody

| Administration mode | Half-life (hours) | AUC (0-t, h*μg/mL) |
|---|---|---|
| Intravenous injection-1 mg/kg | 355.37 | 3997.79 |
| Intravenous injection-3 mg/kg | 290.15 | 5035.86 |
| Subcutaneous injection-3 mg/kg | 188.02 | 9581.64 |

Figure 11A:
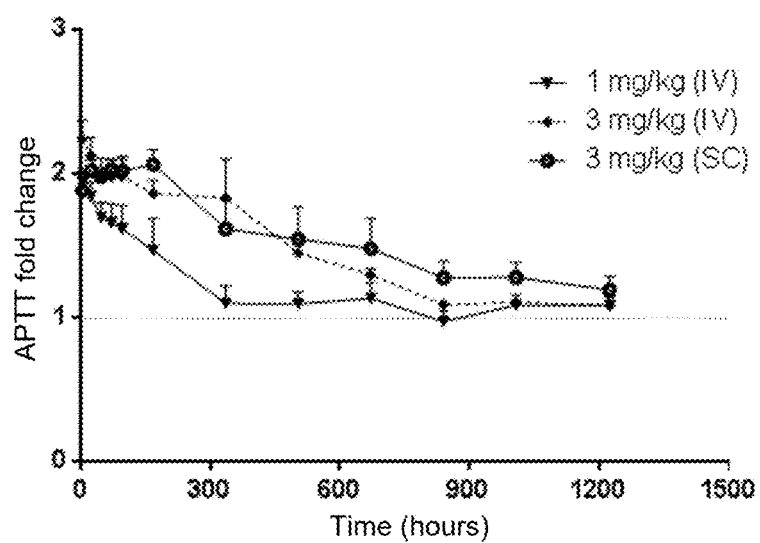
FIG. 11A shows the in vivo pharmacodynamics (PD) detection of APTT activity of humanized anti-human FXI/FXIa antibody in cynomolgus monkeys.
Figure 11B:
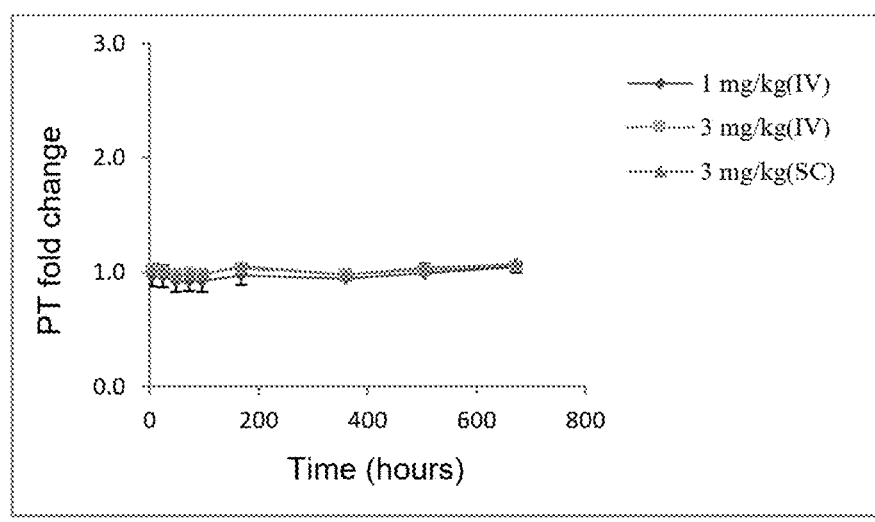
FIG. 11B shows the in vivo pharmacodynamic (PD) detection of PT activity of humanized anti-human FXI/FXIa antibody in cynomolgus monkeys.

The PD detection results showed that 36G9.10-hz73 can be used for intravenous injection and subcutaneous administration to achieve a good effect of prolonging APTT. As shown in FIG. 11A, the dose-effect relationship between the two intravenous injection dose groups was clearly shown, the 3 mg/kg subcutaneous injection group showed a slightly better effect on prolonging APTT than the intravenous injection group, having an effect of prolonging APTT by about 1.3 times at 1008 hours; as shown in FIG. 11B, the three dose groups did not prolong PT, indicating that they had no effect on exogenous coagulation. Therefore, the 36G9.10-hz73 antibody had the potential clinical advantage of not causing the risk of bleeding.

Although the specific embodiments of the present invention have been described in detail, those skilled in the art will understand that various modifications and changes can be made to the details according to all the teachings that have been disclosed, and these changes are within the protection scope of the present invention. All of the present invention is given by the appended claims and any equivalents thereof.

What is claimed is:

1. An antibody or antigen-binding fragment thereof capable of specifically binding to FXI and/or FXIa, wherein the antibody or antigen-binding fragment thereof comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8; wherein the six CDRs are defined by the IMGT numbering system;

(b) a VH comprising a CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35; and a VL comprising a CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38; wherein the six CDRs are defined by the IMGT numbering system;

(c) a VH comprising a CDR-H1 comprising the amino acid sequence of SEQ ID NO: 9, a CDR-H2 comprising the amino acid sequence of any one of SEQ ID NOs: 45, 46, and 10, and a CDR-H3 comprising the amino acid sequence of SEQ ID NO: 11; and a VL comprising a CDR-L1 comprising the amino acid sequence of SEQ ID NO: 12, a CDR-L2 comprising the amino acid sequence of SEQ ID NO: 13, and a CDR-L3 comprising the amino acid sequence of SEQ ID NO: 14; wherein the six CDRs are defined by the AbM numbering system; or (d) a VH comprising a CDR-H1 comprising the amino acid sequence of SEQ ID NO: 39, a CDR-H2 comprising the amino acid sequence of SEQ ID NO: 40 or 47, and a CDR-H3 comprising the amino acid sequence of SEQ ID NO: 41; and a VL comprising a CDR-L1 comprising the amino acid sequence of SEQ ID NO: 42, a CDR-L2 comprising the amino acid sequence of SEQ ID NO: 43, and a CDR-L3 comprising the amino acid sequence of SEQ ID NO: 44; wherein the six CDRs are defined by the AbM numbering system.

2. The antibody or antigen-binding fragment thereof of claim 1, wherein the antibody or antigen-binding fragment thereof comprises:

(a) a VH comprising the amino acid sequence of SEQ ID NO: 15, or a variant thereof having at least about 85% sequence identity to SEQ ID NO: 15; and a VL comprising the amino acid sequence of SEQ ID NO: 18, or a variant thereof having at least about 85% sequence identity to SEQ ID NO: 18;

(b) a VH comprising the amino acid sequence of SEQ ID NO: 1, or a variant thereof having at least about 85% sequence identity to SEQ ID NO: 1; and a VL comprising the amino acid sequence of SEQ ID NO: 2, or a variant thereof having at least about 85% sequence identity to SEQ ID NO: 2;

(c) a VH comprising the amino acid sequence of SEQ ID NO: 15, or a variant thereof having at least about 85% sequence identity to SEQ ID NO: 15; and a VL comprising the amino acid sequence of SEQ ID NO: 20, or a variant thereof having at least about 85% sequence identity to SEQ ID NO: 20;

(d) a VH comprising the amino acid sequence of SEQ ID NO: 16, or a variant thereof having at least about 85% sequence identity to SEQ ID NO: 16; and a VL comprising the amino acid sequence of SEQ ID NO: 18, or a variant thereof having at least about 85% sequence identity to SEQ ID NO: 18;

(e) a VH comprising the amino acid sequence of SEQ ID NO: 17, or a variant thereof having at least about 85% sequence identity to SEQ ID NO: 17; and a VL comprising the amino acid sequence of SEQ ID NO: 19, or a variant thereof having at least about 85% sequence identity to SEQ ID NO: 19;

(f) a VH comprising the amino acid sequence of SEQ ID NO: 17, or a variant thereof having at least about 85% sequence identity to SEQ ID NO: 17; and a VL comprising the amino acid sequence of SEQ ID NO: 18, or a variant thereof having at least about 85% sequence identity to SEQ ID NO: 18;

(g) a VH comprising the amino acid sequence of SEQ ID NO: 29, or a variant thereof having at least about 85% sequence identity to SEQ ID NO: 29; and a VL comprising the amino acid sequence of SEQ ID NO: 30, or a variant thereof having at least about 85% sequence identity to SEQ ID NO: 30; or (h) a VH comprising the amino acid sequence of SEQ ID NO: 31, or a variant thereof having at least about 85% sequence identity to SEQ ID NO: 31; and a VL comprising the amino acid sequence of SEQ ID NO: 32, or a variant thereof having at least about 85% sequence identity to SEQ ID NO: 32.

3. The antibody or antigen-binding fragment thereof of claim 1, wherein the antibody or antigen-binding fragment thereof is murine, chimeric, or humanized.

4. The antibody or antigen-binding fragment thereof of claim 1, wherein the antibody or antigen-binding fragment thereof is a full-length antibody.

5. The antibody or antigen-binding fragment thereof of claim 4, wherein the full-length antibody comprises a heavy chain constant region comprising the amino acid sequence of SEQ ID NO: 21, and a light chain constant region comprising the amino acid sequence of SEQ ID NO: 22.

6. The antibody or antigen-binding fragment thereof of claim 5, wherein the full-length antibody comprises:

(a) a VH comprising the amino acid sequence of SEQ ID NO: 15, and a VL comprising the amino acid sequence of SEQ ID NO: 18;

(b) a VH comprising the amino acid sequence of SEQ ID NO: 15, and VL comprising the amino acid sequence of SEQ ID NO: 20;

(c) a VH comprising the amino acid sequence of SEQ ID NO: 16, and a VL comprising the amino acid sequence of SEQ ID NO: 18;

(d) a VH comprising the amino acid sequence of SEQ ID NO: 17, and a VL comprising the amino acid sequence of SEQ ID NO: 19;

(e) a VH comprising the amino acid sequence of SEQ ID NO: 17, and a VL comprising the amino acid sequence of SEQ ID NO: 18; or (f) a VH comprising the amino acid sequence of SEQ ID NO: 31, and a VL comprising the amino acid sequence of SEQ ID NO: 32.

7. The antibody or antigen-binding fragment thereof of claim 1, wherein the antibody or antigen-binding fragment thereof is selected from the group consisting of a full-length antibody, an scFv, a Fab, a Fab', a F(ab')$_2$, an Fv fragment, a disulfide-ligated Fv(dsFv), and a diabody.

8. The antibody or antigen-binding fragment thereof of claim 1, wherein the antibody or antigen-binding fragment thereof is labeled.

9. The antibody or antigen-binding fragment thereof of claim 1, wherein the antibody or antigen-binding fragment thereof has at least one of the following characteristics:

(a) binding to FXI and/or FXIa with a $K_D$ of less than about 100 nM;

(b) binding to FXI and/or FXIa with an $EC_{50}$ of less than about 500 nM;

(c) the binding of the antibody or antigen-binding fragment thereof to FXI and/or FXIa inhibits or blocks the binding of FXI and/or FXIa to a substrate;

(d) the binding of the antibody or antigen-binding fragment thereof to FXI and/or FXIa inhibits or blocks the catalytic effect of FXI and/or FXIa on a substrate;

(e) the binding of the antibody or antigen-binding fragment thereof to FXI and/or FXIa does not affect exogenous coagulation;

(f) the antibody or antigen-binding fragment thereof has reduced ADCC and/or CDC activity;

(g) the antibody or antigen-binding fragment thereof does not have ADCC and/or CDC activity;

or (h) any combination of (a) to (g).

10. An isolated nucleic acid molecule, which encodes the antibody or antigen-binding fragment thereof of claim 1.

11. The isolated nucleic acid molecule of claim 10, comprising:

(1) a nucleic acid molecule encoding an antibody heavy chain variable region, and/or a nucleic acid molecule encoding an antibody light chain variable region, wherein the nucleic acid molecule encoding the antibody heavy chain variable region has a nucleotide sequence selected from the group consisting of:

(1a) the nucleotide sequence of SEQ ID NO: 23 or 27, (1b) a sequence that is at least about 85% identical to the nucleotide sequence described in (1a), and (1c) a sequence that does not differ from the nucleotide sequence described in (1a) by more than 3, 6, 15, 30, or 45 nucleotides;

and/or the nucleic acid molecule encoding the antibody light chain variable region has a nucleotide sequence selected from the group consisting of:

(1d) the nucleotide sequence of SEQ ID NO: 24 or 28, (1e) a sequence that is at least about 85% identical to the nucleotide sequence described in (1d), and (1f) a sequence that does not differ from the nucleotide sequence described in (1d) by more than 3, 6, 15, 30, or 45 nucleotides;
or
(2) a nucleic acid molecule of SEQ ID NO: 23, and/or a nucleic acid molecule of SEQ ID NO: 24;
or
(3) a nucleic acid molecule of SEQ ID NO: 27, and/or a nucleic acid molecule of SEQ ID NO: 28;
or
(4) a nucleic acid molecule encoding an antibody heavy chain, and/or a nucleic acid molecule encoding an antibody light chain, wherein
the nucleic acid molecule encoding the antibody heavy chain has a nucleotide sequence selected from the group consisting of:
(4a) the nucleotide sequence of SEQ ID NO: 25,
(4b) a sequence that is at least about 85% identical to the nucleotide sequence described in (4a), and
(4c) a sequence that does not differ from the nucleotide sequence described in (4a) by more than 3, 6, 15, 30, or 45 nucleotides;
and/or
the nucleic acid molecule encoding the antibody light chain has a sequence selected from the group consisting of:
(4d) the nucleotide sequence of SEQ ID NO: 26,
(4e) a sequence that is at least about 85% identical to the nucleotide sequence described in (4d), and
(4f) a sequence that does not differ from the nucleotide sequence described in (4d) by more than 3, 6, 15, 30, or 45 nucleotides;
or
(5) a nucleic acid molecule of SEQ ID NO: 25, and/or a nucleic acid molecule of SEQ ID NO: 26.

12. A vector comprising the isolated nucleic acid molecule of claim 10.

13. A host cell comprising the isolated nucleic acid molecule of claim 10, or a vector comprising the isolated nucleic acid molecule.

14. A method for preparing the antibody or antigen-binding fragment thereof of claim 1, which comprises culturing a host cell comprising an isolated nucleic acid molecule encoding the antibody or antigen binding fragment thereof under conditions that allow the expression of the antibody or antigen-binding fragment thereof, and recovering the antibody or antigen-binding fragment thereof from the culture of the cultured host cell.

15. A multispecific antibody comprising 1) the antibody or antigen-binding fragment thereof of claims 1, and 2) a second antibody or antigen-binding fragment thereof, or an antibody mimetic, that specifically binds to a second antigen.

16. A conjugate comprising the antibody or antigen-binding fragment thereof of claim 1, and a conjugate moiety, wherein the conjugate moiety is a detectable label or a therapeutic agent.

17. A pharmaceutical composition, which comprises: (i) a pharmaceutically acceptable carrier and/or an excipient, and (ii) any one of the following:
(a) the antibody or antigen-binding fragment thereof of claim 1,
(b) an isolated nucleic acid molecule encoding the antibody or antigen-binding fragment thereof,
(c) a vector comprising an isolated nucleic acid molecule encoding the antibody or antigen-binding fragment thereof,
(d) a host cell comprising an isolated nucleic acid molecule encoding the antibody or antigen-binding fragment thereof,
(e) a multispecific antibody comprising (1) the antibody or antigen-binding fragment thereof, and (2) another antibody or antigen-binding fragment thereof, or an antibody mimetic, or
(f) a conjugate comprising the antibody or antigen-binding fragment thereof and a conjugate moiety.

18. The pharmaceutical composition of claim 17, wherein the pharmaceutical composition comprises the antibody or antigen-binding fragment thereof in an effective dose that is sufficient to cause at least one of the following biological activities in a subject:
(a) inhibiting or blocking the binding of FXI and/or FXIa to a substrate;
(b) inhibiting or blocking the activation of FXI and/or FXIa-mediated endogenous coagulation pathway;
(c) inhibiting or blocking the activity of FXI and/or FXIa in thrombosis;
(d) prolonging FXI and/or FXIa-mediated clotting time;
(e) inhibiting thrombosis;
(f) preventing and/or treating a disease or disorder associated with coagulation or thromboembolism mediated by FXI and/or FXIa; or
(g) any combination of (a) to (f).

19. The pharmaceutical composition of claim 17, further comprising a second antibody or antigen-binding fragment thereof, or a nucleic acid encoding the second antibody or antigen-binding fragment thereof, wherein the second antibody or antigen-binding fragment thereof:
(a) is another antibody or antigen-binding fragment thereof capable of recognizing a different epitope of FXI or FXIa;
(b) is an antibody or antigen-binding fragment thereof capable of specifically binding to a receptor or ligand selected from the group consisting of: thrombin, antiplasmin, Factor XII, Factor VIII, Factor VII, Factor X, Factor IX, Factor II, tissue Factor, P-selectin and ligand thereof, and L-selectin and ligand thereof; or
(c) any combination of the above antibodies or antigen-binding fragments thereof.

20. A kit comprising an instruction for use and one of the following:
(a) the antibody or antigen-binding fragment thereof of claim 1;
(b) a vector comprising an isolated nucleic acid molecule encoding the antibody or antigen-binding fragment thereof;
(c) a host cell comprising an isolated nucleic acid molecule encoding the antibody or antigen-binding fragment thereof;
(d) a multispecific antibody comprising (1) the antibody or antigen-binding fragment thereof, and (2) another antibody or antigen-binding fragment thereof, or an antibody mimetic;
(e) a conjugate comprising the antibody or antigen-binding fragment thereof, and a conjugate moiety; or
(f) a pharmaceutical composition comprising (1) the antibody or antigen-binding fragment thereof, the vector, the host cell, the multispecific antibody, or the conjugate, and (2) a pharmaceutically acceptable carrier and/or an excipient.

21. A method for (i) preventing and/or treating a disease or disorder associated with coagulation or thromboembolism, (ii) delaying the occurrence of a disease or disorder associated with coagulation or thromboembolism, and/or (iii) reducing or inhibiting the recurrence of a disease or disorder associated with coagulation or thromboembolism, wherein the method comprises administering to a subject in need thereof an effective amount of one of the following:
  (a) the antibody or antigen-binding fragment thereof of claim 1;
  (b) an isolated nucleic acid molecule encoding the antibody or antigen-binding fragment thereof;
  (c) a vector comprising an isolated nucleic acid molecule encoding the antibody or antigen-binding fragment thereof;
  (d) a host cell comprising an isolated nucleic acid molecule encoding the antibody or antigen-binding fragment thereof;
  (e) a multispecific antibody comprising (1) the antibody or antigen-binding fragment thereof; and (2) another antibody or antigen-binding fragment thereof, or an antibody mimetic;
  (f) a conjugate comprising the antibody or antigen-binding fragment thereof, and a conjugate moiety; or
  (g) a pharmaceutical composition comprising (1) the antibody or antigen-binding fragment thereof, the vector, the host cell, the multispecific antibody, or the conjugate, and (2) a pharmaceutically acceptable carrier and/or an excipient.

22. The method of claim 21, wherein the method further comprises administering a second therapy to the subject, and the second therapy comprises administering one or more additional drugs,
  (a) wherein the one or more additional drugs are selected from the group consisting of antiplatelet drugs, anticoagulant drugs, and thrombolytic drugs; or
  (b) wherein the one or more additional drugs are selected from the group consisting of aspirin, clopidogrel, prasugrel, ticagrelor, abciximab, eptifibatide, vorapaxar, unfractionated heparin, heparin, low molecular weight heparin, warfarin, fondaparinux, edoxaban, betrixaban, rivaroxaban, apixaban, dabigatran etexilate, argatroban, bivalirudin, streptokinase, urokinase, alteplase, prourokinase, and any combination thereof.

23. The method of claim 21, wherein the disease or disorder associated with coagulation or thromboembolism is selected from the group consisting of: thrombosis, thrombotic stroke, atrial fibrillation, stroke prevention associated with atrial fibrillation (SPAF), deep vein thrombosis, venous thromboembolism, acute coronary syndrome (ACS), ischemic stroke, acute limb ischemia, chronic thromboembolism pulmonary hypertension, systemic embolism, myocardial infarction (MI), acute myocardial infarction (AMI), stable angina pectoris, unstable angina pectoris, reocclusion and restenosis after coronary intervention, peripheral arterial occlusive disease (PAOD), renal vein thrombosis, transient ischemic attack (TIA), pulmonary thromboembolism, diffuse intravascular coagulation, thromboembolic disorder caused by medical device, ischemia-reperfusion injury, local fibrin deposition, thromboembolic event (VTE) before and after joint replacement (TKA) surgery, coronary heart disease, thromboembolism after myocardial infarction, a stroke in a patient with non-valvular atrial fibrillation, thrombosis and thromboembolism in chronic kidney disease, thrombosis and thromboembolism in a patient undergoing hemodialysis and a patient undergoing extracorporeal membrane oxygenation, deep vein thrombosis (DVT), and pulmonary embolism (PE).

24. A method for detecting the presence or level of FXI and/or FXIa in a sample, comprising contacting the sample with the antibody or antigen-binding fragment thereof of claim 1, or a conjugate comprising the antibody or antigen-binding fragment thereof and a conjugate moiety, under a condition that allows the formation of a complex, and detecting the formation of the complex.

25. The antibody or antigen-binding fragment thereof of claim 4, wherein the full-length antibody comprises 1) a heavy chain constant region comprising the amino acid sequence of SEQ ID NO: 21, or a variant thereof having up to 20 amino acids variations as compared to SEQ ID NO: 21; and/or 2) a light chain constant region comprising the amino acid sequence of SEQ ID NO: 22, or a variant thereof having up to 20 amino acids variations as compared to SEQ ID NO: 22.

26. The antibody or antigen-binding fragment thereof of claim 4, wherein the full-length antibody comprises: (i) a heavy chain constant region of IgG1, IgG2, IgG3, or IgG4; and/or (ii) a κ light chain constant region.

27. The antibody or antigen-binding fragment thereof of claim 8, wherein the label is selected from the group consisting of a radionuclide, a fluorescent dye, a luminescent substance, and a biotin.

* * * * *